US007265131B2

(12) United States Patent
Johnson et al.

(10) Patent No.: US 7,265,131 B2
(45) Date of Patent: Sep. 4, 2007

(54) ISOQUINOLINONE DERIVATIVES AND THEIR USE AS THERAPEUTIC AGENTS

(75) Inventors: Alan T Johnson, Poway, CA (US); Satoru Kaneko, Yokohama (JP); Raju Mohan, Encinitas, CA (US); Kozo Oda, Saitama (JP); Edwin J Schweiger, San Diego, CA (US)

(73) Assignee: Exelixis, Inc., South San Francisco, CA (US)

( * ) Notice: Subject to any disclaimer, the term of this patent is extended or adjusted under 35 U.S.C. 154(b) by 194 days.

(21) Appl. No.: 10/738,964

(22) Filed: Dec. 17, 2003

(65) Prior Publication Data

US 2004/0204447 A1    Oct. 14, 2004

Related U.S. Application Data

(60) Provisional application No. 60/435,851, filed on Dec. 20, 2002.

(51) Int. Cl.
*C07D 217/22* (2006.01)
*A61K 31/47* (2006.01)

(52) U.S. Cl. .................................... 514/309; 546/141
(58) Field of Classification Search ............... 546/141; 514/309
See application file for complete search history.

(56) References Cited

U.S. PATENT DOCUMENTS

| | | | | |
|---|---|---|---|---|
| 3,452,027 | A * | 6/1969 | Myles et al. ................. | 546/141 |
| 4,198,512 | A | 4/1980 | Kubo et al. .................. | 546/142 |
| 5,260,316 | A | 11/1993 | Van Duzer et al. .......... | 514/309 |
| 5,334,600 | A | 8/1994 | Van Duzer et al. .......... | 514/309 |
| 5,350,761 | A | 9/1994 | Van Duzer et al. .......... | 514/373 |
| 5,607,898 | A | 3/1997 | Nakamura et al. ........... | 504/282 |
| 5,607,967 | A | 3/1997 | Friedman et al. ............ | 514/461 |
| 5,665,733 | A | 9/1997 | Servin et al. ................ | 514/309 |
| 5,747,661 | A | 5/1998 | Evans et al. ................. | 536/24.1 |
| 5,945,380 | A | 8/1999 | Gallenkamp et al. ........ | 504/252 |
| 6,184,215 | B1 | 2/2001 | Elias et al. .................. | 514/182 |
| 6,187,814 | B1 | 2/2001 | Elias et al. .................. | 514/531 |
| 6,316,503 | B1 | 11/2001 | Li et al. ...................... | 514/604 |
| 2003/0073614 | A1 | 4/2003 | Schulman et al. ........... | 514/2 |

FOREIGN PATENT DOCUMENTS

| | | |
|---|---|---|
| EP | 424929 A1 | 5/1991 |
| EP | 591937 B1 | 4/1996 |
| EP | 526402 B1 | 1/1998 |
| EP | 845460 A1 | 6/1998 |
| EP | 999208 A1 | 5/2000 |
| WO | WO97/43263 | 11/1997 |
| WO | WO98/00423 | 1/1998 |
| WO | WO98/28268 | 7/1998 |
| WO | WO99/32485 | 7/1999 |
| WO | WO 00/17334 | 3/2000 |
| WO | WO 00/37077 | 6/2000 |
| WO | WO 00/57915 | 10/2000 |
| WO | WO 00/66611 | 11/2000 |
| WO | WO 00/78972 | 12/2000 |
| WO | WO 01/15676 | 3/2001 |
| WO | WO 01/60818 | 8/2001 |
| WO | WO 01/77067 | 10/2001 |
| WO | WO 01/82917 | 11/2001 |
| WO | WO 02/11708 | 2/2002 |
| WO | WO 02/062764 | 8/2002 |
| WO | WO 03/076418 | 9/2003 |

OTHER PUBLICATIONS

Connors et al, Can. J. Chem, vol. 74, pp. 221-226, 1994.*
Aicart et al, Journal of Heterocyclic Chemistry, vol. 22, pp. 921-925, 1985.*
Couture et al, Synthesis, vol. 7, pp. 576-578, Jul. 1986.*
Couture et al, Journal of Organic Chemistry, vol. 56, No. 16, pp. 4977-4980, 1991.*
GenBank Database, Accession No. BC012646, Jun. 29, 2004. Available from www.ncbi.nlm.nih.gov/entrez/.
GenBank Database, Accession No. NM_002957, Jun. 14, 2005. Available from www.ncbi.nlm.nih.gov/entrez/.
GenBank Database, Accession No. NM_005123, Jul. 19, 2005. Available from www.ncbi.nlm.nih.gov/entrez/.
GenBank Database, Accession No. NM_009473, Jul. 4, 2005. Available from www.ncbi.nlm.nih.gov/entrez/.
GenBank Database, Accession No. NM_031626, Apr. 20, 2005. Available from www.ncbi.nlm.nih.gov/entrez/.
GenBank Database, Accession No. NM_031627, Apr. 20, 2005. Available from www.ncbi.nlm.nih.gov/entrez/.
GenBank Database, Accession No. U07132, Jan. 29, 1995. Available from www.ncbi.nlm.nih.gov/entrez/.
GenBank Database, Accession No. U10375, Jul. 22, 1994. Available from www.ncbi.nlm.nih.gov/entrez/.
GenBank Database, Accession No. U18374, Jun. 21, 1995. Available from www.ncbi.nlm.nih.gov/entrez/.
GenBank Database, Accession No. U22662, Jan. 27, 1996. Available from www.ncbi.nlm.nih.gov/entrez/.
GenBank Database, Accession No. X57638, Apr. 18, 2005. Available from www.ncbi.nlm.nih.gov/entrez/.

(Continued)

*Primary Examiner*—Zinna N. Davis
(74) *Attorney, Agent, or Firm*—McDonnell Boehnen Hulbert & Berghoff LLP

(57) ABSTRACT

Compounds of formula (I):

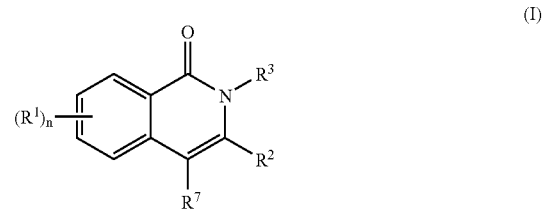

wherein n, $R^1$, $R^2$, $R^3$ and $R^7$ are disclosed herein, are useful in treating disease-states associated with nuclear receptor activity. Pharmaceutical compositions comprising and methods of using said compounds are also disclosed herein.

27 Claims, No Drawings

OTHER PUBLICATIONS

GenBank Database, Accession No. XM_042579, Feb. 6, 2002. Available from www.ncbi.nlm.nih.gov/entrez/.

GenBank Database, Accession No. XM_053680, May 8, 2002. Available from www.ncbi.nlm.nih.gov/entrez/.

Akakura and Yamamoto, "Methylalumoxane as a Highly Lewis Acidic Reagent for Organic Synthesis," *Synlett* (3): 277-278, Mar. 1997.

Baumgarth, M. et al., "(2-Methyl-5-(methylsulfonyl)benzoyl) guanidine Na+/H+ Antiporter Inhibitors," *Journal of Medicinal Chemistry 40*(13): 2017-2034, Jun. 20, 1997.

Beugelmans and Bois-Choussy, "A Common and General Access to Berberine and Benzo [c] Phenathridine Alkaloids," *Tetrahedron 48*(38): 8285-8294, 1992.

Cheon, S.H. et al., "Sturucture-Activity Relationship Studies of Isoquinolinone Type Anticancer Agent," *Arch. Pharm. Res. 24*(4): 276-280, 2001.

Chiasson, J-L. et al., "The efficacy of Acarbose in the Treatment of Patients with Non-Insulin-dependent Diabetes Mellitus," *Annals of Internal Medicine 121*(12): 928-935, Dec. 15, 1994.

Comins and Brown, "Ortho Metalation by α-Amino Alkoxides," *The Journal of Organic Chemistry 49*(6): 1078-1083, Mar. 23, 1984.

Coniff and Krol, "Acarbose: A Review of US Clinical Experience," *Clinical Theapeutics 19*(1): 16-26, Jan.-Feb. 1997.

Coniff, R.F. etal., "Multicenter, Placebo-Controlled Trial Comparing Acarbose (BAY g 5421) With Pacebo, Tolbutamide, and Tolbutamide-Plus-Acarbose in Non-Insulin-Dependent Diabetes Mellitus," *The American Journal of Medicine 98*: 443-451, May 1995.

Couture, A. et al., "A New Synthetic Route to 2-Methyl-3-(Aryl or Alkyl)-1-Oxo-1,2-Dihydroisoquinolines via an Intramolecular Wittig Reacation," *Tetrahedron 48*(19): 3857-3866, 1992.

Couture, A. et al., "Fluoride ion-induced cyclization of o-[bis(trimethysilyl)methyl]-N-acylbenzamide derivatives. New efficient synthesis of 2,3,-differentially substituted 1(2H)-isoquinolones," *Journal of the Chemical Society, Perkin Transactions 1*: 469-476, 1997.

Couture, A. et al., "Intramolecular Peterson olefination of ortho-trimethylsilylmethyl-N-acyl-N-alkylbenzamides. A new route to 2-alkyl-1(2H)isoquinolones," *Journal of Organometallic Chemistry 440*(1-2): 7-13, Nov. 17, 1992.

Davis, S.E. et al., "The Preparation of Substituted 1(2H)-Isoquinolinones from Dilithiated 2-Methyl-N-Arylbenzamides, 2-Methyl-N-(Arylmethyl)-Benzamide, or 2-Methylbenzoic Acid, 2,2-Dimethylhydrazide," *Synethetic Communications 27*(17): 2961-2969, 1997.

De Wet, J.R. et al., "Firefly Luciferase Gene: Structure and Expression Mammalian Cells," *Molecular and Cellular Biology 7*(2): 725-737, Feb. 1987.

Gaillard, O. et al., "Apolipoprotein E intrathecal synthesis is decreased in multiple sclerosis patients," *Annals of Clinical Biochemistry 33*(Part 2): 148-150, Mar. 1996.

Haffner, S.M., "Management of Dyslipidemia in Adults With Diabetes," *Diabetes Care 21*(1): 160-178, Jan. 1998.

Haimova, M.A. et al., "One-Pot Synthesis of 5,6-Dihydro-8H-dibenzo[a,g]quinolizine-8-ones and Related Isoquinolines; A New Synthesis of Xylopinine," *Synthesis* (10): 845-847, 1980.

Koller, M.U. et al., "The Preparaion of Substituted 1(2H)-Isoquinolones From Polylithiated 2-(2-Methylphenyl) Hydrazainecarboxylic Acid Esters," *Synthetic Communications 26*(9): 1763-1774, 1996.

Kwiterovich, P.O., "State-of-the-Art Update and Review: Clinical Trials of Lipid-Lowering Agents," *The American Journal of Cardiology 82*(12A): 3U-17U, Dec. 17, 1998.

Luckow and Schütz, "CAT constructions with multiple unique restriction sites for the functional analysis of eukaryotic promoters and regulatory elements," *Nucleic Acids Research 15*(13): 5490, 1987.

Mahler and Adler, "Clinical Review 102. Type 2 Diabetes Mellitus: Update on Diagnosis, Pathophysiology, and Treatment," *The Journal of Clinical Endocrinology & Metabolism 84*(4): 1165-1171, 1999.

Mali, R.S. et al., "A Convenient Synthesis of N-Methyl-1(2H)-isoquinolones," *Synthesis* (4): 329-330, Apr. 1982.

Ohta, S. et al., "Synthesis of 3-Substituted Isocoumarins and Related Natural Products," *Chemical & Pharmaceutical Bulletin 41*(6): 1188-1190, 1993.

Oitzl, M.S. et al., "Severe learning deficits in apolipoprotein E-knockout mice in a water maze task," *Brain Research 752*:189-196, 1997.

Peet, D.J. et al., "Cholesterol and Bile Acid Metabolism Are Impaired in Mice Lacking the Nuclear Oxysterol Receptor LXRα," *Cell 93*(5): 693-704, May 29, 1998.

Poirier, J., "Apolipoprotein E in animal models of CNS injury and in Alzheimer's disease," *Trends in Neurosciences 17*(12): 525-530, Dec. 1994.

Roselaar and Daugherty, "Apolipoprotein E-deficient mice have impaired innate immune responses to *Listeria monocytogenes* in vivo," *Journal of Lipid Research 39*:1740-1743, 1998.

Sinal, C.J. et al., "Targeted Disruption of the Nuclear Receptor FXR/BAR Impairs Bile Acid and Lipid Homeostasis," *Cell 102*: 731-744, Sep. 15, 2000.

Treus, M. et al., "A new route to 3-(2-vinylphenyl)-2-methyl-2H-isoquinolin-1-ones and benzo[c]phenathridines: total synthesis of fagaronine," *Tetrahedron Letters 43*: 5323-5325, 2002.

U.K. Prospective Diabetes Study Group, "UKPDS 28: A Randomized Trial of Efficacy of Early Addition of Metformin in Sulfonylurea-Treated Type 2 Diabetes," *Diabetes Care 21*(1): 87-92, Jan. 1998.

Willy, P.J. et al., "LXR, a nuclear receptor that defines a distinct retinoid response pathway," *Genes & Development 9*(9): 1033-1045, May 1, 1995.

\* cited by examiner

ISOQUINOLINONE DERIVATIVES AND THEIR USE AS THERAPEUTIC AGENTS

CROSS REFERENCE TO RELATED APPLICATIONS

This application claims the benefit of U.S. Provisional Patent Application No. 60/435,851, filed Dec. 20, 2002, where this provisional application is incorporated herein by reference in its entirety.

FIELD OF THE INVENTION

This invention is directed to isoquinolinone derivatives and their use as therapeutic agents. In particular, this invention is directed to isoquinolinone derivatives and their use in modulating the activity of orphan nuclear receptors, pharmaceutical compositions containing such derivatives, and methods of using such derivatives in treating disease-states associated with nuclear receptor activity.

BACKGROUND OF THE INVENTION

The average American consumes about 450 mg of cholesterol per day and produces an additional 500 to 1000 mg in the liver and other tissues. Although cholesterol is essential to health, excess serum cholesterol has been implicated in atherosclerosis, heart attack and stroke, and is a leading cause of death in the United States, accounting for approximately 600,000 deaths per year.

Although mammals can endogenously synthesize fats, including cholesterol, their main source is direct absorption from the diet. The liver is able to partially regulate the levels of circulating lipids by modulating the rates of fatty acid uptake, esterification into triglycerides or oxidation, processes that are coordinated at the transcriptional level by a small number of nuclear receptors.

Serum cholesterol levels are also regulated by the rate of transport of this lipid out of the cells into the blood, a process that is mediated with the help of protein carriers called lipoproteins. Two important classes of these protein carriers are low-density lipoproteins (LDL) and high-density lipoproteins (HDL). LDL is responsible for transporting cholesterol from the liver to various tissues and body cells while HDL is largely responsible for transporting excess or unused cholesterol back to the liver where it may be metabolized to bile acids for excretion.

Healthy cholesterol levels for LDL should be lower than 130 mg/dl while HDL should be more than 50 mg/dl. When the body has too much LDL, i.e., above 160 mg/dl, cholesterol starts to accumulate along the interior walls of arteries leading to a buildup of fatty deposits in the coronary arteries and other blood vessels leading to atherosclerosis and atherosclerotic cardiovascular diseases.

Because the diet of most western societies is rich in animal products, the ability to be able to modulate serum cholesterol concentrations in vivo independently of the diet would be particularly useful for preventing coronary heart disease and other disorders associated with the high dietary intake of fat. Accordingly the development of agonists, antagonists, inverse agonists, partial agonists and antagonists, as well as pan agonists and antagonists, for the nuclear receptors involved in regulating the transcription of proteins involved in lipid metabolism and transport would have immediate application in treating disorders associated with alterations in fat metabolism, transport or uptake.

Such nuclear receptors include the peroxisome proliferator activated receptors (PPARα, β/δ and γ) the farnesoid receptor (FXR), the Pregnane X-Receptor (PXR), Constitutive Androstane Receptor (CAR) and the liver X receptors (LXRα and LXRβ). The various alternate names, and representative GenBank Accession numbers for these receptors are shown below.

| Receptor Name and Subtype | Alternative Names | Accession No. |
|---|---|---|
| PPARα (Peroxisome Proliferator Activated Receptor-α NR1C1 | PPARα, | NM_005036 |
| PPARβ(Peroxisome Proliferator Activated Receptor) NR1C2 | PPAR-β PPAR-δ, NUC1, FAAR | XM_004285 |
| PPARγ, Peroxisome Proliferator Activated Receptor-γ NR1C3 | PPARγ, | XM_003059 |
| LXR-β, (Liver X receptor-β) NR1H2 | LXR-β, UR, NER-1, RIP15, OR1 | U07132 |
| LXR-α, (Liver X receptor-α) NR1H3 | LXRA, XR2, RLD1 | U22662 |

| Receptor Name and Subtype | Alternative Names | Accession No. |
|---|---|---|
| FXR (Farnesyl X receptor) NR1H4 | FXR, RIP14, HRR1 | NM_005123 |
| PXR (Pregnane X-Receptor) 2 Isoforms NR1I2 | PXR.1, PXR.2, SXR, ONR1, xOR6, BXR | NM_003889 NM_022002 AF364606 |
| CAR α (Constitutive Androstane Receptor) NR1I3 | CAR1, MB67 | XM_042458 |
| CAR β(Constitutive Androstane Receptor) NR1I4 | mCAR1 (mouse) | |

These receptors bind to hormone response elements as heterodimers with a common partner, the retinoid X receptors (RXRs) (see, e.g., Levin et al., *Nature* (1992), Vol. 355, pp. 359-361 and Heyman et al., *Cell* (1992), Vol. 68, pp. 397-406). The table below lists such RXR receptors.

| Receptor Name and Subtype | Alternative Names | Accession No. |
|---|---|---|
| RXRα, (Retinoid X-Receptor-α) NR2B1 | RXRα | NM_002957 |
| RXRβ(Retinoid X-Receptor-β) NR2B2 | RXRβ, H2RIIBP | XM_042579 |
| RXRγ (Retinoid X-Receptor-γ) NR2B3 | RXRγ | XM_053680 |

The three proteins encoded by the RXR genes are all able to heterodimerize with any of the receptors above, and these heterodimers can be activated by both RXR ligands (i.e., rexinoids) as well as ligands for the partner nuclear receptor.

Role in Lipid Metabolism

Although all the nuclear receptors above play a role in controlling overall lipid metabolism, distinct classes of receptor play defined cell type specific roles in the entire process.

The peroxisome proliferator-activated receptors (PPARs) for example, are fatty acid and eicosanoid inducible nuclear receptors, that are regulated by fatty acid derivatives. The three PPAR isoforms have distinct patterns of expression and function within the body.

PPARα is mostly expressed in brown adipose tissue, liver, kidney, duodenum, heart and skeletal muscle. PPARγ expression, by contrast, is mainly found in brown and white adipose tissues and, to a lesser extent, in the large intestine, the retina and in some parts of the immune system. PPARβ is the most ubiquitously expressed isotype and is found in higher amounts than α and γ in almost all tissues examined, except the adipose tissue.

PPARα participates in the control of fatty acid transport and uptake by stimulating the transcription of genes encoding the fatty acid transport protein (FATP), the fatty acid translocase (FAT/CD36) and the liver cytosolic fatty acid binding protein (L-FABP). The metabolism of triglyceride-rich lipoproteins is modulated by PPARα dependent stimulation of the lipoprotein lipase gene, which facilitates the release of fatty acids from lipoprotein particles, and by the down regulation of apolipoprotein C-III. Furthermore, PPAR α upregulates apolipoproteins A-I and A-II in humans, which leads to an increase in plasma high-density lipoprotein (HDL) cholesterol. Additional PPAR α target genes participate in the mitochondrial fatty acid metabolism, in ketogenesis and in microsomal fatty acid ω-hydroxylation by cytochrome P450 ω-hydroxylases that belong to the CYP4A family.

By comparison, PPARγ plays a major role in regulating adipose tissue differentiation and fat storage, which is a major site for the overall control of lipid homeostasis in the body.

The Farnesoid X Receptor (FXR) is an orphan receptor initially identified from a rat liver cDNA library (Forman, B M, et al., *Cell* 81: 81 687-693 (1995)) that plays a major role in the homeostasis of cholesterol in the body. FXR is most abundantly expressed in the liver, intestine, kidney and adrenal, and is activated by several naturally occurring bile acids including chenodeoxycholic acid (CDCA), deoxycholic acid (DCA), lithocholic acid (LCA), and the taurine and glycine conjugates of these bile acids.

It is now known that FXR functions as a bile acid sensor that participates in the regulation of cholesterol homeostasis by controlling the conversion of cholesterol to bile acids. High bile acid levels suppress the conversion of cholesterol to bile acids by activating FXR that acts to suppress the expression of the cholesterol 7 α-hydrolase gene (Cyp7A) and other enzymes involved in bile acid synthesis. Cyp7A is responsible for the first enzymatic step in the conversion of cholesterol to bile acids and represents the key rate limiting enzymatic step in bile acid synthesis. Cyp7A belongs to the Cytochrome P-450 family of enzymes, and is found exclusively in the liver. FXR is also involved in controlling the synthesis of isoprenoid derivatives (including cholesterol). In the ileum, FXR mediates the expression of the intestinal bile acid binding protein (IBABP) that is involved in the cellular uptake and trafficking of bile acids.

High cholesterol levels also lead to the accumulation of oxidized derivatives of cholesterol, such as 24(S), 25-epoxycholesterol, 22(R)-hydroxycholesterol, and 24(S)-hydroxycholesterol which are activators of the Liver X Receptors (LXRs).

These compounds tend to accumulate in the cell under conditions of elevated cholesterol in the cell and act on LXR to coordinate an increase in the transcription of genes involved in cholesterol transport out of the cell, the synthesis of enzymes involved in the metabolic conversion of cholesterol to bile acids, and an increase in the expression of genes involved in fatty acid synthesis. By promoting the metabolic conversion of cholesterol to bile acids, these LXR agonists also promote the transfer of cholesterol from the periphery to the liver for catabolism and excretion.

In mammals two forms of LXR exist (α and β) with different patterns of expression. LXR α is expressed predominantly in the liver, with lower levels found in kidney, intestine, spleen and adrenal tissue (see, e.g., Willy, et al. (1995) *Gene Dev.* 9(9):1033-1045), while LXR β is ubiquitously expressed.

The LXRs are also regulated by fatty acids, and these metabolites have opposing (antagonistic) effects on LXR transcriptional activity. Thus LXR antagonists, including fatty acids and their derivatives, act to decrease cholesterol transport out of the cell, decrease fatty acid synthesis and the conversion of cholesterol to bile acids by acting to suppress the transcription of genes involved in these pathways.

The target genes regulated by LXR, which effect these changes, are important enzymes involved in sterol metabolism, transport and metabolic diseases. Genes involved in sterol transport for example, including the ATP binding cassette transporters ABCA1, ABCG1, ABCG5 and ABCG8 as well as the cholesterol transport protein apolipoprotein apoE (a component of LDL), have been shown to have direct links to various disease syndromes.

Mutations in sterol transporter ABCA1 give rise to Tangier disease, and result in an almost complete absence of HDL cholesterol and promote accumulation of cholesterol within peripheral tissues. Both the ABCG5 and ABCG8 genes are both linked to human genetic syndromes including sitosterolemia, characterized by perturbed cholesterol transport.

As a component of all lipoprotein fractions, ApoE plays an important role in cholesterol transport. In ApoE knock out mice, the animals rapidly develop hypercholesterolemia and atherosclerosis, even when kept on a low fat diet. In man, mutations in apoE are associated hyperlipidemia and rapid onset of atherosclerosis (see, *Atherosclerosis* (1995), Vol. 112, pp.19-28).

LXRs also regulate fatty acid metabolism by controlling expression of the sterol response element binding protein 1c (SREBP1c), the master transcriptional regulator of fatty acid synthesis, and the enzymes that participate in this metabolic pathway. The ability of LXRs to regulate these enzymes has important consequences for carbohydrate and lipid homeostasis throughout the body.

The regulation of cholesterol transport, metabolism and SREBP1c expression suggests that LXR modulators (either alone, or in combination) have the potential to be useful in the treatment of diseases associated with defects in cholesterol transport, fatty acid metabolism and cholesterol metabolism.

Thus, there is a need for compounds, compositions and methods of selectively modulating the activity of nuclear receptors, including LXRs, FXR, PPARs, PXRs, CARs and orphan nuclear receptors for use in the treatment, prevention, or amelioration of one or more symptoms of numerous disease states.

DESCRIPTION OF THE RELATED ART

The preparation of certain isoquinolinone derivatives is described in Davis, S. E. et al., *Synthetic Communications* (1997), Vol. 27, No. 17, pp. 2961-2969.

The preparation and use of isoquinolyl substituted hydroxylamine derivatives and their use for inhibiting 5-lipoxygenase activity is described in U.S. Pat. No. 5,260,316.

PCT published patent application No. WO 00/66611 discloses steroid derivatives for the treatment of various disorders.

PCT published patent application No. WO 01/77607 discloses methods for synthesizing LXR ligands on a solid support, and combinatorial libraries comprising such compounds.

PCT published patent application No. WO 01/60818 discloses compositions and methods for modulating LXR function.

PCT published patent application No. WO 02/11708 discloses methods of increasing Apo E expression.

PCT published patent application No. WO 01/15676 discloses methods of modulating HDL cholesterol.

PCT published patent application No. WO 00/78972 discloses methods of increasing cholesterol efflux.

U.S. Pat. No. 6,184,215 discloses methods of treating epidermal barrier dysfunction.

U.S. Pat. No. 5,607,967 discloses 5-(tetradecyloxy)-2-furan carboxylic acid (TOFA) and it's use for treating Alzheimer's disease.

U.S. Pat. No. 6,316,503 discloses compositions for modulating LXR function in a cell.

European Patent Application 0 424 929 discloses the preparation of certain isoquinolone derivatives useful in inhibiting HMG-CoA reductase.

SUMMARY OF THE INVENTION

The present invention is directed to isoquinolinone derivatives and their use in treating disease-states associated with nuclear receptor activity.

Accordingly, in one aspect, this invention is directed to compounds of formula

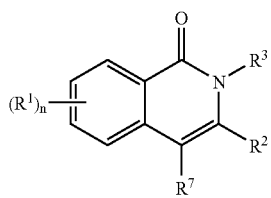

(I)

wherein:
n is 0 to 4;
each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, heteroaryl, cyano, nitro, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$S(O)_tR^4$ (where t is 0 to 2), and —$R^6$—$S(O)_pN(R^4)_2$ (where p is 1 or 2);
$R^2$ is alkynyl optionally substituted with —$Si(R^4)_3$, hydroxyalkyl, optionally substituted aryl, or optionally substituted cycloalkyl,
or $R^2$ is aryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

or $R^2$ is heteroaryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

$R^3$ is alkyl or cycloalkylalkyl optionally substituted with one or more substituents selected from the group consisting of alkyl, alkenyl, cyano, nitro, halo, haloalkyl, haloalkenyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

or $R^3$ is aralkyl wherein the aryl group of the aralkyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

or $R^3$ is heteroarylalkyl wherein the heteroaryl group of the heteroarylakyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$R^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen or aralkyl;

as a single stereoisomer, a mixture of stereoisomers, or as a racemic mixture of stereoisomers; or as a solvate or polymorph; or as a pharmaceutically acceptable salt thereof; with the following provisos:

(a) when n is 0, $R^7$ is hydrogen and $R^3$ is either benzyl or 4-methylbenzyl, $R^2$ can not be 4-chlorophenyl, 4-methoxyphenyl, or 3-chlorophenyl;

(b) when $R^7$ is hydrogen, n is 0 or 1, $R^1$ is chloro, methyl, trifluoromethyl or methoxy, and $R^3$ is methyl, $R^2$ can not be unsubstituted furanyl or thiophenyl optionally substituted by methyl;

(c) when $R^7$ is hydrogen, n is 0, 1 or 2, each $R^1$ is independently halo, trifluoromethyl, an alkyl group of 1 to 3 carbons or $—R^6—OR^4$ where $R^6$ is a direct bond and $R^4$ is an alkyl group of 1 to 3 carbons, and $R^3$ is an alkyl group of 1 to 3 carbons, $R^2$ can not be phenyl optionally substituted by halo, an alkyl group of 1 to 3 carbons or $—R^6—OR^4$ where $R^6$ is a direct bond and $R^4$ is an alkyl group of 1 to 4 carbons;

(d) when $R^7$ is hydrogen, n is 0 or 1, $R^1$ is halo, methyl or methoxy, and $R^3$ is methyl, $R^2$ can not be oxazole.

The following compounds of formula (I) may also be excluded from the scope of this invention:

compounds of formula (I) where n is O, $R^2$ is 4-fluorophenyl, $R^7$ is hydrogen and $R^3$ is selected from the group consisting of methyl, ethyl, n-propyl, n-butyl, n-pentyl, n-heptyl, n-nonyl, $—CH(CH_3)_2$, $—CH_2CH(CH_3)_2$, cyclopropyl, cyclohexyl, $—(CH_2)_2—F$, $—(CH_2)_2C(O)N(CH_3)_2$, $—(CH_2)_2—OCH_3$, $—(CH_2)_2—SCH_3$, 4-fluorophenyl, $—(CH_2)_2$-phenyl, $—(CH_2)_2$-(4-fluoro)phenyl, $—(CH_2)_2$-(3-fluoro)phenyl, $—(CH_2)_2$-(2-fluoro)phenyl, $—(CH_2)_2$-(4-methyl)phenyl, $—(CH_2)_2$-(4-methoxy)phenyl, $—(CH_2)_2$-(2-methoxy)phenyl, $—(CH_2)_2$-(4-chloro)phenyl, $—(CH_2)_2$-(3-trifluoromethyl)phenyl, and $—(CH_2)_3$-phenyl;

compounds of formula (I) where n is O, $R^3$ is $—CH(CH_3)_2$ or n-propyl, $R^7$ is hydrogen and $R^2$ is selected from the group consisting of 4-methylphenyl, 2-methoxy-4-fluorophenyl, 2-fluoro-4-methoxyphenyl, 2-methoxy-5-fluorophenyl, 2-methyl-4-fluorophenyl, and 2,4-difluorophenyl; or compounds of formula (I) where n is 1 or 2, each $R^1$ is independently methyl, fluoro, chloro or methoxy; $R^2$ is 4-fluorophenyl or 2,4-difluorophenyl; $R^7$ is hydrogen and $R^3$ is selected from $—CH(CH_3)_2$ or n-propoyl.

In another aspect, this invention is directed to pharmaceutical compositions comprising a pharmaceutically acceptable excipient and a compound of formula (I) as described above. Such compositions are useful in treating a disease-state in a mammal, wherein the disease-state is alleviated by the modulation of the activity of a nuclear receptor.

In another aspect, this invention is directed to methods of treating a disease-state in a mammal, wherein the disease-state is alleviated by the modulation of the activity of a nuclear receptor and wherein the methods comprise administering to the mammal having the disease-state a therapeutically effective amount of a compound of formula (I) as described above. In one aspect of this method the nuclear receptor is LXR α or LXR β.

In another aspect, this invention is directed to methods of regulation of LXR α or LXR β activity throughout an organism or in a particular tissue wherein the methods comprise administering to the organism a compound of formula (I) as described above. In this context, a selective compound typically exhibits at least a 10-fold difference in $EC_{50}$ or $IC_{50}$ for LXR α compared to LXR β in at least one in vitro or in vivo assay described herein.

In another aspect, this invention is directed to methods of treating, preventing, or ameliorating one or more symptoms or causes of atherosclerosis, wherein the methods comprise administering to the organism a therapeutically effective amount of a compound of formula (I) as described above.

In another aspect, this invention is directed to methods of treating, preventing, or ameliorating one or more symptoms or causes of atherosclerotic cardiovascular diseases, wherein the methods comprise administering to the organism a therapeutically effective amount of a compound of formula (I) as described above.

In another aspect, this invention is directed to methods of treating, preventing, or ameliorating one or more symptoms or causes of hyperlipidemia, wherein the methods comprise administering to the organism a therapeutically effective amount of a compound of formula (I) as described above.

In another aspect, this invention is directed to methods of modulating cholesterol metabolism, catabolism, synthesis, absorption, re-absorption, transport, reverse transport, secretion or excretion wherein the methods comprise administering to the organism a compound of formula (I) as described above.

In another aspect, this invention is directed to the use of a compound of the invention, or a pharmaceutically acceptable derivative thereof, in combination with one or more of the following therapeutic agents, antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A:cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, vitamin C, vitamin E, non-steroidal anti-inflammatory drugs (NSAIDs) (such as prostaglandin synthase inhibitors (e.g., choline magnesium salicylate, salicylsalicyclic acid)), COX-1 or COX-2 inhibitors, corticosteroids, (such as methylprednisone, prednisone, or cortisone), β-blockers, angiotensin II modulators, angiotensin converting enzyme modulators, platelet aggregation inhibitors, fibrinogen receptor modulators, aspirin or fibric acid derivatives, sulfonylureas (such as chlorpropamide, tolbutamide, acetohexamide, tolazamide, glyburide, gliclazide, glynase, glimepiride, and glipizide), biguanides (such as mefformin), thiazolidinediones (such as ciglitazone, pioglitazone, troglitazone, and rosiglitazone), PPARα, PPARβ and PPARγ modulators; dehydroepiandrosterone (also referred to as DHEA or its conjugated sulphate ester, DHEA-$SO_4$), antiglucocorticoids, TNFα inhibitors, α-glucosidase inhibitors (such as acarbose, miglitol, and voglibose), amylin, pramlintide, other insulin secretogogues (such as repaglinide, gliquidone, and nateglinide), insulin, phenylpropanolamine, phentermine, diethylpropion, mazindol, fenfluramine, dexfenfluramine, phentiramine, $β_3$ adrenoceptor modulators; sibutramine, dopamine $D_2$ receptor modulators, gastrointestinal lipase inhibitors (such as orlistat), leptin, neuropeptide Y, enterostatin, cholecytokinin, bombesin, histamine $H_3$ receptor modulators, melanocyte stimulating hormone, corticotrophin releasing factor, galanin and gamma amino butyric acid (GABA).

DETAILED DESCRIPTION OF THE INVENTION

A. Definitions

As used herein the singular forms "a", "and", and "the" include plural referents unless the context clearly dictates otherwise. For example, "a compound" refers to one or more of such compounds, while "the enzyme" includes a particular enzyme as well as other family members and equivalents thereof as known to those skilled in the art.

As used in the specification and appended claims, unless specified to the contrary, the following terms have the meaning indicated.

"Alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (iso-propyl), n-butyl, n-pentyl, 1,1-dimethylethyl (t-butyl), and the like. Unless stated otherwise specifically in the specification, the alkyl radical may be optionally substituted by one or more substituents selected from the group consisting of cyano, nitro, —$OR^4$, —$N(R^4)_2$, —$C(O)R^4$, —$C(O)OR^4$, —$C(O)N(R^4)_2$, —$N(R^4)C(O)OR^5$, —$N(R^4)C(O)R^4$, —$N[S(O)_tR^4]_2$ (where t is 0 to 2), —$N(R^4)(S(O)_tR^4)$ (where t is 0 to 2), —$S(O)_pOR^4$ (where p is 1 to 2), —$S(O)_tR^4$ (where t is 0 to 2), and —$S(O)_pN(R^4)_2$ (where p is 1 to 2) where each $R^4$ and $R^5$ is as defined above in the Summary of the Invention. Unless stated otherwise specifically in the specification, it is understood that for radicals, as defined below, that contain a substituted alkyl group that the substitution can occur on any carbon of the alkyl group.

"Alkenyl" refers to a straight or branched hydrocarbon chain radical consisting solely of carbon and hydrogen atoms, containing at least one double bond, having from two to eight carbon atoms, and which is attached to the rest of the molecule by a single bond or a double bond, e.g., ethenyl, prop-1-enyl, but-1-enyl, pent-1-enyl, penta-1,4-dienyl, and the like. Unless stated otherwise specifically in the specification, the alkenyl radical may be optionally substituted by one or more substituents selected from the group consisting of cyano, nitro, —$OR^4$, —$N(R^4)_2$, —$C(O)R^4$, —$C(O)OR^4$, —$C(O)N(R^4)_2$, —$N(R^4)C(O)OR^5$, —$N(R^4)C(O)R^4$, —$N[S(O)_tR^4]_2$ (where t is 0 to 2), —$N(R^4)(S(O)_tR^4)$ (where t is 0 to 2), —$S(O)_pOR^4$ (where p is 1 to 2), —$S(O)_tR^4$ (where t is 0 to 2), and —$S(O)_pN(R^4)_2$ (where p is 1 to 2) where each $R^4$ and $R^5$ is as defined above in the Summary of the Invention. Unless stated otherwise specifically in the specification, it is understood that for radicals, as defined below, that contain a substituted alkenyl group that the substitution can occur on any carbon of the alkenyl group.

"Aryl" refers to refers to aromatic monocyclic or multicyclic ring system containing from 6 to 19 carbon atoms, where the ring system may be partially or fully saturated. Aryl groups include, but are not limited to groups such as fluorenyl, phenyl and naphthyl. Unless stated otherwise specifically in the specification, the term "aryl" or the prefix "ar-" (such as in "aralkyl") is meant to include aryl radicals optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, —$R^6$—$OR^4$, —$R^6$—$N(R^4)_2$, —$R^6$—$C(O)R^4$, —$R^6$—$C(O)OR^4$ —$R^6$—$C(O)N(R^4)_2$, —$R^6$—$N(R^4)C(O)OR^5$, —$R^6$—$N(R^4)C(O)R^4$, —$R^6$—$N[S(O)_tR^4]_2$ (where t is 0 to 2), —$R^6$—$N(R^4)(S(O)_tR^4)$ (where t is 0 to 2), —$R$—$S(O)_pOR^4$ (where p is 1 to 2), —$R$—$S(O)_tR^4$ (where t is 0 to 2), and —$R_6$—$S(O)_pN(R^4)_2$ (where p is 1 to 2) where each $R^4$, $R^6$ and $R^5$ is as defined above in the Summary of the Invention.

"Aralkyl" refers to a radical of the formula —$R_aR_b$ where $R_a$ is an alkyl radical as defined above and $R_b$ is one or more aryl radicals as defined above, e.g., benzyl, diphenylmethyl and the like. The aryl radical(s) may be optionally substituted as described above.

"Alkylene" and "alkylene chain" refer to a straight or branched divalent hydrocarbon chain consisting solely of carbon and hydrogen, containing no unsaturation and having from one to eight carbon atoms, e.g., methylene, ethylene, propylene, n-butylene, and the like. The alkylene chain may be optionally substituted by one or more substituents selected from the group consisting of halo, cyano, nitro, aryl, cycloalkyl, heterocyclyl, —$OR^4$, —$N(R^4)_2$, —$C(O)R^4$, —$C(O)OR^4$, —$C(O)N(R^4)_2$, —$N(R^4)C(O)OR^5$, —$N(R^4)C(O)R^4$, —$N[S(O)_tR^4]_2$ (where t is 0 to 2), —$N(R^4)(S(O)_tR^4)$ (where t is 0 to 2), —$S(O)_pOR^4$ (where p is 1 to 2), —$S(O)_tR^4$ (where t is 0 to 2), and —$S(O)_pN(R^4)_2$ (where p is 1 to 2) where each $R^4$ and $R^5$ is as defined above in the Summary of the Invention. The alkylene chain may be attached to the rest of the molecule through any two carbons within the chain.

"Cycloalkyl" refers to a stable monovalent monocyclic or bicyclic hydrocarbon radical consisting solely of carbon and hydrogen atoms, having from three to ten carbon atoms, and which is saturated and attached to the rest of the molecule by a single bond, e.g., cyclopropyl, cyclobutyl, cyclopentyl, cyclohexyl, decalinyl and the like. Unless otherwise stated specifically in the specification, the term "cycloalkyl" is meant to include cycloalkyl radicals which are optionally substituted by one or more substituents independently selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, —$R^6$—$OR^4$, —$R^6$—$N(R^4)_2$, —$R^6$—$C(O)R^4$, —$R^6$—$C(O)OR^4$ —$R^6$—$C(O)N(R^4)_2$, —$R^6$—$N(R^4)C(O)OR^5$, —$R^6$—$N(R^4)C(O)R^4$, —$R^6$—$N[S(O)_tR^4]_2$ (where t is 0 to 2), —$R^6$—$N(R^4)(S(O)_tR^4)$ (where t is 0 to 2), —$R^6$—$S(O)_pOR^4$ (where p is 1 to 2), and —$R^6$—$S(O)_tR^4$ (where t is 0 to 2), —$R$—$S(O)_pN(R^4)_2$ (where p is 1 to 2) where each $R^4$, $R^6$ and $R^5$ is as defined above in the Summary of the Invention.

"Cycloalkylalkyl" refers to a radical of the formula —$R_aR_d$ where $R_a$ is an alkyl radical as defined above and $R_d$ is a cycloalkyl radical as defined above. The alkyl radical and the cycloalkyl radical may be optionally substituted as defined above.

"Halo" refers to bromo, chloro, fluoro or iodo.

"Haloalkyl" refers to an alkyl radical, as defined above, that is substituted by one or more halo radicals, as defined above, e.g., trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like.

"Haloalkenyl" refers to an alkenyl radical, as defined above, that is substituted by one or more halo radicals, as defined above, e.g., 2-bromoethenyl, 3-bromoprop-1-enyl, and the like.

"Heterocyclyl" refers to a stable 3- to 18-membered ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized; and the heterocyclyl radical may be partially or fully saturated. For purposes of this invention, the term "heterocyclyl" refers to a ring radical that is not aromatic. Examples of such heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, thiazolidinyl, tetrahydrofuryl, trithianyl, tetrahydropyranyl, thiamorpholinyl, thiamorpholinyl sulfoxide, and thiamorpholinyl sulfone. Unless stated otherwise specifically in the specification, the term "heterocyclyl" is meant to include heterocyclyl radicals as defined above which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, $-R^6-OR^4$, $-R^6-N(R^4)_2$, $-R^6-C(O)R^4$, $-R^6-C(O)OR^4$, $-R^6-C(O)N(R^4)_2$, $-R^6-N(R^4)C(O)OR^5$, $-R^6-N(R^4)C(O)R^4$, $-R^6-N[S(O)_tR^4]_2$ (where t is 0 to 2), $-R^6-N(R^4)(S(O)_tR^4)$ (where t is 0 to 2), $-R^6-S(O)_pOR^4$ (where p is 1 to 2), $-R^6-S(O)_tR^4$ (where t is 0 to 2), and $-R^6-S(O)_pN(R^4)_2$ (where p is 1 to 2) where each $R^4$, $R^6$ and $R^5$ is as defined above in the Summary of the Invention.

"Heterocyclylalkyl" refers to a radical of the formula $-R_aR_e$ where $R_a$ is an alkyl radical as defined above and $R_e$ is a heterocyclyl radical as defined above, and if the heterocyclyl is a nitrogen-containing heterocyclyl, the heterocyclyl may be attached to the alkyl radical at the nitrogen atom. The heterocyclyl radical may be optionally substituted as defined above.

"Heteroaryl" refers to a 3- to 18-membered ring radical which consists of carbon atoms and from one to five heteroatoms selected from the group consisting of nitrogen, oxygen and sulfur. For purposes of this invention, the heterocyclyl radical may be a monocyclic, bicyclic, tricyclic or tetracyclic ring system, which may include fused or bridged ring systems; and the nitrogen, carbon or sulfur atoms in the heterocyclyl radical may be optionally oxidized; the nitrogen atom may be optionally quaternized. For purposes of this invention, "heteroaryl" ring radicals are aromatic. Examples include, but are not limited to, azepinyl, acridinyl, benzimidazolyl, benzthiazolyl, benzindolyl, benzothiadiazolyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzotriazolyl, benzo[4,6]imidazo[1,2-a]pyridinyl, carbazolyl, cinnolinyl, dibenzofuranyl, furanyl, furanonyl, isothiazolyl, imidazolyl, indolyl, indazolyl, isoindolyl, indolinyl, isoindolinyl, indolizinyl, isoxazolyl, naphthyridinyl, oxadiazolyl, 2-oxoazepinyl, oxazolyl, oxiranyl, phenazinyl, phenothiazinyl, phenoxazinyl, phthalazinyl, pteridinyl, purinyl, pyrrolyl, pyrazolyl, pyridinyl, pyrazinyl, pyrimidinyl, pyridazinyl, quinazolinyl, quinoxalinyl, quinolinyl, quinuclidinyl, isoquinolinyl, thiazolyl, thiadiazolyl, triazolyl, tetrazolyl, triazinyl, and thiophenyl. Unless stated otherwise specifically in the specification, the term "heteroaryl" is meant to include heteroaryl radicals as defined above which are optionally substituted by one or more substituents selected from the group consisting of alkyl, alkenyl, halo, haloalkyl, haloalkenyl, cyano, nitro, aryl, aralkyl, cycloalkyl, cycloalkylalkyl, heterocyclyl, heterocyclylalkyl, $-R^6-OR^4$, $-R^6-N(R^4)_2$, $-R^6-C(O)R^4$, $-R^6-C(O)OR^4$, $-R^6-C(O)N(R^4)_2$, $-R^6-N(R^4)C(O)OR^5$, $-R^6-N(R^4)C(O)R^4$, $-R^6-N[S(O)_tR^4]_2$ (where t is 0 to 2), $-R^6-N(R^4)(S(O)_tR^4)$ (where t is 0 to 2), $-R^6-S(O)_pOR^4$ (where p is 1 to 2), $-R^6-S(O)_tR^4$ (where t is 0 to 2), and $-R^6-S(O)_pN(R^4)_2$ (where p is 1 to 2) where each $R^4$, $R^6$ and $R^5$ is as defined above in the Summary of the Invention.

As used herein, compounds which are "commercially available" may be obtained from standard commercial sources including Acros Organics (Pittsburgh, Pa.), Aldrich Chemical (Milwaukee, Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester, Pa.), Crescent Chemical Co. (Hauppauge, N.Y.), Eastman Organic Chemicals, Eastman Kodak Company (Rochester, N.Y.), Fisher Scientific Co. (Pittsburgh, Pa.), Fisons Chemicals (Leicestershire UK), Frontier Scientific (Logan, Utah), ICN Biomedicals, Inc. (Costa Mesa, Calif.), Key Organics (Cornwall U.K.), Lancaster Synthesis (Windham, N.H.), Maybridge Chemical Co. Ltd. (Cornwall U.K.), Parish Chemical Co. (Orem, Utah), Pfaltz & Bauer, Inc. (Waterbury, Conn.), Polyorganix (Houston, Tex.), Pierce Chemical Co. (Rockford, Ill.), Riedel de Haen AG (Hannover, Germany), Spectrum Quality Product, Inc. (New Brunswick, N.J.), TCI America (Portland, Oreg.), Trans World Chemicals, Inc. (Rockville, Md.), and Wako Chemicals U.S.A., Inc. (Richmond, Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modern Synthetic Reactions", 2nd Ed., W. A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C. may be contacted for more details). Chemicals that are known but not commercially available in catalogs may be prepared by custom chemical synthesis houses, where many of the standard chemical supply houses (e.g., those listed above) provide custom synthesis services.

"Prodrugs" is meant to indicate a compound that may be converted under physiological conditions or by solvolysis to a biologically active compound of the invention. Thus, the term "prodrug" refers to a metabolic precursor of a compound of the invention that is pharmaceutically acceptable. A prodrug may be inactive when administered to a subject in need thereof, but is converted in vivo to an active compound of the invention. Prodrugs are typically rapidly transformed in vivo to yield the parent compound of the invention, for example, by hydrolysis in blood. The prodrug compound often offers advantages of solubility, tissue compatibility or delayed release in a mammal (see, Bundgard, H., *Design of Prodrugs* (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers which release the active compound of the invention in vivo when such prodrug is administered to a mammalian subject. Prodrugs of a compound of the invention may be prepared by modifying functional groups present in the compound of the invention in such a way that the modifications are cleaved, either in routine manipulation or in vivo, to the parent compound of the invention. Prodrugs include compounds of the invention wherein a hydroxy, amino or mercapto group is bonded to any group that, when the prodrug of the compound of the invention is administered to a mammalian subject, cleaves to form a free hydroxy, free amino or free mercapto group, respectively. Examples of prodrugs include, but are not limited to, acetate, formate and benzoate derivatives of alcohol and amine functional groups in the compounds of the invention and the like.

"Stable compound" and "stable structure" are meant to indicate a compound that is sufficiently robust to survive isolation to a useful degree of purity from a reaction mixture, and formulation into an efficacious therapeutic agent.

The terms "mammal", "mammalian subject" and "organism" are used herein interchangeably and include humans and domestic animals, such as cats, dogs, swine, cattle, sheep, goats, horses, rabbits, and the like.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals as defined herein and aryl radicals having no substitution.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts.

"Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts which retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

"Pharmaceutically acceptable derivative" refers to pharmaceutically acceptable salts as defined herein and also includes esters, prodrugs, solvates and polymorphs of the compounds of the invention.

"Therapeutically effective amount" refers to that amount of a compound of formula (I) which, when administered to a mammal, preferably a human, is sufficient to effect treatment, as defined below, for a disease-state associated the nuclear receptor activity. The amount of a compound of formula (I) which constitutes a "therapeutically effective amount" will vary depending on the compound, the condition and its severity, and the age of the mammal to be treated, but can be determined routinely by one of ordinary skill in the art having regard to his own knowledge and to this disclosure.

"Modulating" or "modulate" refers to the treating, prevention, suppression, enhancement or induction of a function or condition. For example, the compounds of the present invention can modulate hyperlipidemia by lowering cholesterol in a human, thereby suppressing hyperlipidemia.

"Treating" or "treatment" as used herein covers the treatment of a disease-state associated the nuclear receptor activity as disclosed herein, in a mammal, preferably a human, and includes:

(i) preventing a disease-state associated the nuclear receptor activity from occurring in a mammal, in particular, when such mammal is predisposed to the condition but has not yet been diagnosed as having it;

(ii) inhibiting a disease-state associated the nuclear receptor activity, i.e., arresting its development; or (iii) relieving a disease-state associated the nuclear receptor activity, i.e., causing regression of the condition.

The compounds of formula (I), or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)- isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

The nomenclature used herein for the compounds of formula (I) is a modified form of the I.U.P.A.C. nomenclature system wherein the compounds are named herein as derivatives of the isoquinolinone central moiety. For example, a compound of formula (I) wherein n is 1 and $R^1$ is methyl in the 8-position, $R^2$ is 4-phenoxyphenyl, and $R^3$ is benzyl, i.e., the compound of the following formula:

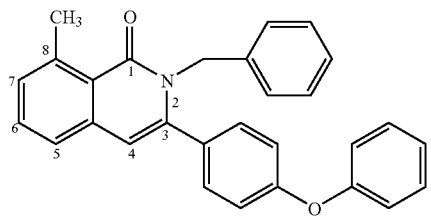

is named herein as 2-benzyl-8-methyl-3-(4-phenoxyphenyl)-2H-isoquinolin-1-one.

The term "atherosclerosis" refers to process whereby atherosclerotic plaques form within the inner lining of the artery wall leading to atherosclerotic cardiovascular diseases. Atherosclerotic cardiovascular diseases can be recognized and understood by physicians practicing in the relevant fields of medicine, and include without limitation, restenosis, coronary heart disease (also known as coronary artery heart disease or ischemic heart disease), cerebrovascular disease including ischemic stroke, multi-infarct dementia, and peripheral vessel disease, including intermittent claudication, and erectile dysfunction.

The term "dyslipidemia" refers to abnormal levels of lipoproteins in blood plasma including both depressed and/or elevated levels of lipoproteins (e.g., elevated levels of Low Density Lipoprotein, (LDL), Very Low Density Lipoprotein (VLDL) and depressed levels of High Density Lipoprotein (HDL) (less than 40 mg/dL)).

As used herein, "$EC_{50}$" refers to a dosage, concentration or amount of a particular test compound that elicits a dose-dependent response at 50% of maximal expression of a particular response that is induced, provoked or potentiated by the particular test compound.

The term "hyperlipidemia" refers to the presence of an abnormally elevated level of lipids in the blood. Hyperlipidemia can appear in at least three forms: (1) hypercholesterolemia, i.e., an elevated LDL cholesterol level (120 mg/dL and above); (2) hypertriglyceridemia, i.e., an elevated triglyceride level; (150 mg/dL and above) and (3) combined hyperlipidemia, i.e., a combination of hypercholesterolemia and hypertriglyceridemia.

As used herein, "$IC_{50}$" refers to an amount, concentration or dosage of a particular test compound that achieves a 50% inhibition of a maximal response, such as modulation of nuclear receptor, including the LXR α or LXR β activity, in an assay that measures such response.

As used herein, "LXR α" refers to all mammalian forms of such receptor including, for example, alternative splice isoforms and naturally occurring isoforms. Representative LXR α species include, without limitation the rat (Genbank Accession NM_031627), mouse (Genbank Accession BC012646), and human (GenBank Accession No. U22662) forms of the receptor.

As used herein, "LXR β" refers to all mammalian forms of such receptor including, for example, alternative splice isoforms and naturally occurring isoforms. Representative LXR β species include, without limitation the rat (GenBank Accession NM_031626), mouse (Genbank Accession NM_009473), and human (GenBank Accession No. U07132) forms of the receptor.

As used herein "LXR" or "LXRs" refers to both LXR α and LXR β.

The terms "obese" and "obesity" refers to a Body Mass Index (BMI) greater than 27.8 kg/m$^2$ for men and 27.3 kg/m$^2$ for women (BMI equals weight (kg)/height (m$^2$).

B. Utility of the Compounds of the Invention

The compounds of the invention exhibit valuable pharmacological properties in mammals, and are particularly useful as selective LXR agonists, antagonists, inverse agonists, partial agonists and antagonists, for the treatment, or prevention of diseases associated with, or symptoms arising from the complications of, altered cholesterol transport, cholesterol reverse transport, fatty acid metabolism, cholesterol absorption, cholesterol re-absorption, cholesterol secretion, cholesterol excretion, or cholesterol metabolism.

These diseases include, for example, hyperlipidemia, dyslipidemia, hypercholesterolemia, atherosclerosis, atherosclerotic cardiovascular diseases, hyperlipoproteinemia, (see, e.g., Patent Application Publication Nos. WO 00/57915 and WO 00/37077), hyperglycemia, insulin resistance, diabetes, lipodystrophy, obesity, syndrome X (US Patent Application No. 20030073614, International Patent Application Publication No. WO 01/82917), excess lipid deposition in peripheral tissues such as skin (xanthomas) (see, e.g., U.S. Pat. Nos. 6,184,215 and 6,187,814), stroke, peripheral occlusive disease, memory loss (*Brain Research* (1997), Vol. 752, pp.189-196), optic nerve and retinal pathologies (i.e., macular degeneration, retintis pigmentosa), repair of traumatic damage to the central or peripheral nervous system (*Trends in Neurosciences* (1994), Vol.17, pp. 525-530), prevention of the degenerative process due to aging (*American Journal of Pathology* (1997), Vol. 151, pp.1371-1377), Parkinson's disease or Alzheimer's disease (see, e.g., International Patent Application Publication No. WO 00/17334; *Trends in Neurosciences* (1994), Vol. 17, pp. 525-530), prevention of degenerative neuropathies occurring in diseases such as diabetic neuropathies (see, e.g., International Patent Application Publication No. WO 01/82917), multiple sclerosis (*Annals of Clinical Biochem.* (1996), Vol. 33, No. 2, pp. 148-150), and autoimmune diseases (*J. Lipid Res.* (1998), Vol. 39, pp. 1740-1743).

Also provided, are methods of increasing the expression of ATP-Binding Cassette (ABCA1), (see, e.g., International Patent Application Publication No. WO 00/78972) thereby increasing reverse cholesterol transport in mammalian cells using the claimed compounds and compositions.

Accordingly in another aspect, the invention also includes methods to remove cholesterol from tissue deposits such as atherosclerotic plaques or xanthomas in a patient with atherosclerosis or atherosclerotic cardiovascular disease manifest by clinical signs of such disease, wherein the methods comprise administering to the patient a therapeutically effective amount of a compound or composition of the present invention.

Additionally, the instant invention also provides a method for preventing or reducing the risk of a first or subsequent occurrence of an atherosclerotic cardiovascular disease event including ischemic heart disease, ischemic stroke, multi-infarct dementia, and intermittent claudication comprising the administration of a prophylactically effective amount of a compound or composition of the present invention to a patient at risk for such an event. The patient may already have atherosclerotic cardiovascular disease at the time of administration, or may be at risk for developing it. Risk factors for developing atherosclerotic cardiovascular disease events include increasing age (65 and over), male gender, a family history of atherosclerotic cardiovascular disease events, high blood cholesterol (especially LDL or "bad" cholesterol over 100 mg/dL), cigarette smoking and exposure to tobacco smoke, high blood pressure, diabetes, obesity and physical inactivity.

Also contemplated herein is the use of a compound of the invention, or a pharmaceutically acceptable derivative thereof, in combination with one or more of the following therapeutic agents in treating atherosclerosis: antihyperlipidemic agents, plasma HDL-raising agents, antihypercholesterolemic agents, cholesterol biosynthesis inhibitors (such as HMG CoA reductase inhibitors, such as lovastatin, simvastatin, pravastatin, fluvastatin, atorvastatin and rivastatin), acyl-coenzyme A:cholesterol acytransferase (ACAT) inhibitors, probucol, raloxifene, nicotinic acid, niacinamide, cholesterol absorption inhibitors, bile acid sequestrants (such as anion exchange resins, or quaternary amines (e.g., cholestyramine or colestipol)), low density lipoprotein receptor inducers, clofibrate, fenofibrate, benzofibrate, cipofibrate, gemfibrizol, vitamin $B_6$, vitamin $B_{12}$, anti-oxidant vitamins, $\beta$-blockers, anti-diabetes agents, angiotensin II antagonists, angiotensin converting enzyme inhibitors, platelet aggregation inhibitors, fibrinogen receptor antagonists, aspirin or fibric acid derivatives.

In one embodiment compounds of the invention are used in combination with a cholesterol biosynthesis inhibitor, particularly an HMG-CoA reductase inhibitor. The term HMG-CoA reductase inhibitor is intended to include all pharmaceutically acceptable salt, ester, free acid and lactone forms of compounds which have HMG-CoA reductase inhibitory activity and, therefore, the use of such salts, esters, free acids and lactone forms is included within the scope of this invention. Compounds which have inhibitory activity for HMG-CoA reductase can be readily identified using assays well-known in the art. For instance, suitable assays are described or disclosed in U.S. Pat. No. 4,231,938 and WO 84/02131. Examples of suitable HMG-CoA reductase inhibitors include, but are not limited to, lovastatin (MEVACOR®; see, U.S. Pat. No. 4,231,938); simvastatin (ZOCOR®); see, U.S. Pat. No. 4,444,784); pravastatin sodium (PRAVACHOL®); see, U.S. Pat. No. 4,346,227); fluvastatin sodium (LESCOL®; see, U.S. Pat. No. 5,354,772); atorvastatin calcium (LIPITOR®); see, U.S. Pat. No. 5,273,995) and rivastatin (also known as cerivastatin; see, U.S. Pat. No. 5,177,080). The structural formulas of these and additional HMG-CoA reductase inhibitors that can be used in combination with the compounds of the invention are described at page 87 of M. Yalpani, "Cholesterol Lowering Drugs," *Chemistry & Industry*, pp. 85-89 (5 Feb. 1996). In presently preferred embodiments, the HMG-CoA reductase inhibitor is selected from lovastatin and simvastatin.

The compounds of the present invention can also be used in methods for decreasing hyperglycemia and insulin resistance, i.e., in methods for treating diabetes (International Patent Application Publication No. WO 01/82917), and in methods of treatment, prevention, or amelioration of disorders related to, or arising as complications of diabetes, hyperglycemia or insulin resistance including the cluster of disease states, conditions or disorders that make up "Syndrome X" (See US Patent Application 20030073614) comprising the administration of a therapeutically effective amount of a compound or composition of the present invention to a patient in need of such treatment.

Additionally the instant invention also provides a method for preventing or reducing the risk of developing hyperglycemia, insulin resistance, diabetes or syndrome X in a patient, comprising the administration of a prophylactically effective amount of a compound or composition of the present invention to a patient at risk for such an event.

Diabetes mellitus, commonly called diabetes, refers to a disease process derived from multiple causative factors and characterized by elevated levels of plasma glucose, referred to as hyperglycemia. See, e.g., LeRoith, D. et al., (eds.), DIABETES MELLITUS (Lippincott-Raven Publishers, Philadelphia, Pa. U.S.A. 1996). According to the American Diabetes Association, diabetes mellitus is estimated to affect approximately 6% of the world population. Uncontrolled hyperglycemia is associated with increased and premature mortality due to an increased risk for macrovascular and macrovascular diseases, including nephropathy, neuropathy, retinopathy, hypertension, cerebrovascular disease and coronary heart disease. Therefore, control of glucose homeostasis is a critically important approach for the treatment of diabetes.

There are two major forms of diabetes: type 1 diabetes (formerly referred to as insulin-dependent diabetes or IDEM); and type 2 diabetes (formerly referred to as noninsulin dependent diabetes or NIDDM).

Type 2 diabetes is a disease characterized by insulin resistance accompanied by relative, rather than absolute, insulin deficiency. Type 2 diabetes can range from predominant insulin resistance with relative insulin deficiency to predominant insulin deficiency with some insulin resistance. Insulin resistance is the diminished ability of insulin to exert its biological action across a broad range of concentrations. In insulin resistant individuals, the body secretes abnormally high amounts of insulin to compensate for this defect. When inadequate amounts of insulin are present to compensate for insulin resistance and adequate control of glucose, a state of impaired glucose tolerance develops. In a significant number of individuals, insulin secretion declines further and the plasma glucose level rises, resulting in the clinical state of diabetes. Type 2 diabetes can be due to a profound resistance to insulin stimulating regulatory effects on glucose and lipid metabolism in the main insulin-sensitive tissues: muscle, liver and adipose tissue. This resistance to insulin responsiveness results in insufficient insulin activation of glucose uptake, oxidation and storage in muscle and inadequate insulin repression of lipolysis in adipose tissue and of glucose production and secretion in liver. In Type 2 diabetes, free fatty acid levels are often elevated in obese and some non-obese patients and lipid oxidation is increased.

Premature development of atherosclerosis and increased rate of cardiovascular and peripheral vascular diseases are characteristic features of patients with diabetes. Hyperlipidemia is an important precipitating factor for these diseases. Hyperlipidemia is a condition generally characterized by an abnormal increase in serum lipids, e.g., cholesterol and triglyceride, in the bloodstream and is an important risk factor in developing atherosclerosis and heart disease. For a review of disorders of lipid metabolism, see, e.g., Wilson, J.

et al., (ed.), Disorders of Lipid Metabolism, Chapter 23, *Textbook of Endocrinology*, 9th Edition, (W. B. Sanders Company, Philadelphia, Pa. U.S.A. 1998). Hyperlipidemia is usually classified as primary or secondary hyperlipidemia. Primary hyperlipidemia is generally caused by genetic defects, while secondary hyperlipidemia is generally caused by other factors, such as various disease states, drugs, and dietary factors. Alternatively, hyperlipidemia can result from both a combination of primary and secondary causes of hyperlipidemia. Elevated cholesterol levels are associated with a number of disease states, including coronary artery disease, angina pectoris, carotid artery disease, strokes, cerebral arteriosclerosis, and xanthoma.

Dyslipidemia, or abnormal levels of lipoproteins in blood plasma, is a frequent occurrence among diabetics, and has been shown to be one of the main contributors to the increased incidence of coronary events and deaths among diabetic subjects (see, e.g., Joslin, *E. Ann. Chim. Med.* (1927), Vol. 5, pp. 1061-1079). Epidemiological studies since then have confirmed the association and have shown a several-fold increase in coronary deaths among diabetic subjects when compared with non-diabetic subjects (see, e.g., Garcia, M. J. et al., *Diabetes* (1974), Vol. 23, pp.105-11 (1974); and Laakso, M. and Lehto, S., *Diabetes Reviews* (1997), Vol. 5, No. 4, pp. 294-315). Several lipoprotein abnormalities have been described among diabetic subjects (Howard B., et al., *Arteriosclerosis* (1978), Vol. 30, pp.153-162).

The compounds of the invention can also be used effectively in combination with one or more additional active diabetes agents depending on the desired target therapy (see, e.g., Turner, N. et al., *Prog. Drug Res.* (1998), Vol. 51, pp.33-94; Haffner, S., *Diabetes Care* (1998), Vol.21, pp.160-178; and DeFronzo, R. et al. (eds.), *Diabetes Reviews* (1997), Vol. 5, No. 4). A number of studies have investigated the benefits of combination therapies with oral agents (see, e.g., Mahler, R., *J. Clin. Endocrinol. Metab.* (1999), Vol. 84, pp.1165-71; United Kingdom Prospective Diabetes Study Group: UKPDS 28, *Diabetes Care* (1998), Vol. 21, pp. 87-92; Bardin, C. W.(ed.), CURRENT THERAPY IN ENDOCRINOLOGY AND METABOLISM, 6th Edition (Mosby—Year Book, Inc., St. Louis, Mo. 1997); Chiasson, J. et al., *Ann. Intern. Med.* (1994), Vol. 121, pp. 928-935; Coniff, R. et al., *Clin. Ther.* (1997), Vol. 19, pp. 16-26; Coniff, R. et al., *Am. J. Med.* (1995), Vol. 98, pp. 443-451; Iwamoto, Y. et al., *Diabet. Med.* (1996), Vol. 13, pp. 365-370; Kwiterovich, P., *Am. J. Cardiol* (1998), Vol. 82 (12A), pp. 3U-17U). These studies indicate that diabetes and hyperlipidemia modulation can be further improved by the addition of a second agent to the therapeutic regimen.

Accordingly, the compounds of the invention may be used in combination with one or more of the following therapeutic agents in treating diabetes: sulfonylureas (such as chlorpropamide, tolbutamide, acetohexamide, tolazamide, glyburide, gliclazide, glynase, glimepiride, and glipizide), biguanides (such as mefformin), thiazolidinediones (such as ciglitazone, pioglitazone, troglitazone, and rosiglitazone), and related insulin sensitizers, such as selective and non-selective activators of PPARα, PPARβ and PPARγ; dehydroepiandrosterone (also referred to as DHEA or its conjugated sulphate ester, DHEA-$SO_4$); antiglucocorticoids; TNFα inhibitors; α-glucosidase inhibitors (such as acarbose, miglitol, and voglibose), pramlintide (a synthetic analog of the human hormone amylin), other insulin secretogogues (such as repaglinide, gliquidone, and nateglinide), insulin, as well as the therapeutic agents discussed above for treating atherosclerosis.

Further provided by this invention are methods of using the compounds of the invention to treat obesity, as well as the complications of obesity. Obesity is linked to a variety of medical conditions including diabetes and hyperlipidemia. Obesity is also a known risk factor for the development of type 2 diabetes (See, e.g., Barrett-Conner, E., *Epidemol. Rev.* (1989), Vol. 11, pp. 172-181; and Knowler, et. al., *Am. J. Clin. Nutr.* (1991), Vol. 53, pp. 1543-1551).

In addition, the compounds of the invention can be used in combination with agents used in treated obesity or obesity-related disorders. Such agents, include, but are not limited to, phenylpropanolamine, phentermine, diethylpropion, mazindol, fenfluramine, dexfenfluramine, phentiramine, $\beta_3$ adrenoceptor agonist agents; sibutramine, gastrointestinal lipase inhibitors (such as orlistat), and leptins. Other agents used in treating obesity or obesity-related disorders include neuropeptide Y, enterostatin, cholecytokinin, bombesin, amylin, histamine $H_3$ receptors, dopamine $D_2$ receptor modulators, melanocyte stimulating hormone, corticotrophin releasing factor, galanin and gamma amino butyric acid (GABA).

C. Evaluation of the Utility of the Compounds of the Invention

Standard physiological, pharmacological and biochemical procedures are available for testing the compounds to identify those that possess biological activities that modulate the activity or nuclear receptors, including the LXRs (LXRα and LXRβ). Such assays include, for example, biochemical assays such as binding assays, fluorescence polarization assays, FRET based coactivator recruitment assays (see, generally, Glickman et al., *J. Biomolecular Screening* (2002), Vol. 7, No.1, pp. 3-10, as well as cell based assays including the co-transfection assay, the use of LBD-Gal 4 chimeras and protein-protein interaction assays, (see, Lehmann. et al., *J. Biol Chem.* (1997), Vol. 272, No. 6, pp. 3137-3140.

High throughput screening systems are commercially available (see, e.g., Zymark Corp., Hopkinton, Mass.; Air Technical Industries, Mentor, Ohio; Beckman Instruments Inc., Fullerton, Calif.; Precision Systems, Inc., Natick, Mass.) that enable these assays to be run in a high throughput mode. These systems typically automate entire procedures, including all sample and reagent pipetting, liquid dispensing timed incubations, and final readings of the microplate in detector(s) appropriate for the assay. These configurable systems provide high throughput and rapid start up as well as a high degree of flexibility and customization. The manufacturers of such systems provide detailed protocols for various high throughput systems. Thus, for example, Zymark Corp. provides technical bulletins describing screening systems for detecting the modulation of gene transcription, ligand binding, and the like.

Assays that do not require washing or liquid separation steps are preferred for such high throughput screening systems and include biochemical assays such as fluorescence polarization assays (see, for example, Owicki, J., *Biomol. Screen* (2000 October), Vol. 5, No. 5, pp. 297), scintillation proximity assays (SPA) (see, for example, Carpenter et al., *Methods Mol. Biol.* (2002), Vol 190, pp. 31-49) and fluorescence resonance energy transfer energy transfer (FRET) or time resolved FRET based coactivator recruitment assays (Mukherjee et al., *J. Steroid Biochem. Mol. Biol.* (2002 July); Vol. 81, No. 3, pp. 217-25; (Zhou et al., *Mol. Endocrinol.* (1998 October), Vol. 12, No. 10, pp. 1594-604). Generally such assays can be preformed using either the full length receptor, or isolated ligand binding domain (LBD). In the case of LXR α the LBD comprises amino acids 188-447, for LXR β the LDB comprises amino acids 198-461, and for FXR, the LBD comprises amino acids 244 to 472 of the full length sequence.

If a fluorescently labeled ligand is available, fluorescence polarization assays provide a way of detecting binding of compounds to the nuclear receptor of interest by measuring changes in fluorescence polarization that occur as a result of the displacement of a trace amount of the label ligand by the compound. Additionally this approach can also be used to monitor the ligand dependent association of a fluorescently labeled coactivator peptide to the nuclear receptor of interest to detect ligand binding to the nuclear receptor of interest.

The ability of a compound to bind to a receptor, or heterodimer complex with RXR, can also be measured in a homogeneous assay format by assessing the degree to which the compound can compete off a radiolabelled ligand with known affinity for the receptor using a scintillation proximity assay (SPA). In this approach, the radioactivity emitted by a radiolabelled compound (for example, [$^3$H] 24,25 Epoxycholesterol) generates an optical signal when it is brought into close proximity to a scintillant such as a Ysi-copper containing bead, to which the nuclear receptor is bound. If the radiolabelled compound is displaced from the nuclear receptor the amount of light emitted from the nuclear receptor bound scintillant decreases, and this can be readily detected using standard microplate liquid scintillation plate readers such as, for example, a Wallac MicroBeta reader.

The heterodimerization of LXR with RXRα can also be measured by fluorescence resonance energy transfer (FRET), or time resolved FRET, to monitor the ability of the compounds provided herein to bind to LXR or other nuclear receptors. Both approaches rely upon the fact that energy transfer from a donor molecule to an acceptor molecule only occurs when donor and acceptor are in close proximity. Typically the purified LBD of the nuclear receptor of interest is labeled with biotin then mixed with stoichiometric amounts of europium labeled streptavidin (Wallac Inc.), and the purified LBD of RXRα is labeled with a suitable fluorophore such as CY5™. Equimolar amounts of each modified LBD are mixed together and allowed to equilibrate for at least 1 hour prior to addition to either variable or constant concentrations of the sample for which the affinity is to be determined. After equilibration, the time-resolved fluorescent signal is quantitated using a fluorescent plate reader. The affinity of the compound can then be estimated from a plot of fluorescence versus concentration of compound added.

This approach can also be exploited to measure the ligand dependent interaction of a co-activator peptide with a nuclear receptor in order to characterize the agonist or antagonist activity of the compounds disclosed herein. Typically the assay in this case involves the use a recombinant Glutathione-S-transferase (GST)-nuclear receptor ligand binding domain (LBD) fusion protein and a synthetic biotinylated peptide sequenced derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought in to close proximity to the allophycocyanin moiety there is little or no energy transfer and excitation of the europium chelate results in emission at 615 nm. Thus the intensity of light emitted at 665 nm gives an indication of the strength of the protein-protein interaction. The activity of a nuclear receptor antagonist can be measured by determining the ability of a compound to competitively inhibit (i.e., $IC_{50}$) the activity of an agonist for the nuclear receptor.

In addition a variety of cell based assay methodologies may be successfully used in screening assays to identify and profile the specificity of compounds of the present invention. These approaches include the co-transfection assay, translocation assays, complementation assays and the use of gene activation technologies to over express endogenous nuclear receptors.

Three basic variants of the co-transfection assay strategy exist, co-transfection assays using full-length nuclear receptor, co transfection assays using chimeric nuclear receptors comprising the ligand binding domain of the nuclear receptor of interest fused to a heterologous DNA binding domain, and assays based around the use of the mammalian two hybrid assay system.

The basic co-transfection assay is based on the co-transfection into the cell of an expression plasmid to express the nuclear receptor of interest in the cell with a reporter plasmid comprising a reporter gene whose expression is under the control of DNA sequence that is capable of interacting with that nuclear receptor (see, for example, U.S. Pat. Nos. 5,071,773; 5,298,429 and 6,416,957). Treatment of the transfected cells with an agonist for the nuclear receptor increases the transcriptional activity of that receptor which is reflected by an increase in expression of the reporter gene which may be measured by a variety of standard procedures.

For those receptors that function as heterodimers with RXR, such as the LXRs, the co-transfection assay typically includes the use of expression plasmids for both the nuclear receptor of interest and RXR. Typical co-transfection assays require access to the full length nuclear receptor and suitable response elements that provide sufficient screening sensitivity and specificity to the nuclear receptor of interest.

Typically, the expression plasmid comprises: (1) a promoter, such as an SV40 early region promoter, HSV tk promoter or phosphoglycerate kinase (pgk) promoter, CMV promoter, Srα promoter or other suitable control elements known in the art, (2) a cloned polynucleotide sequence, such as a cDNA encoding a receptor, co-factor, or fragment thereof, ligated to the promoter in sense orientation so that transcription from the promoter will produce a RNA that encodes a functional protein, and (3) a polyadenylation sequence. For example and not limitation, an expression cassette of the invention may comprise the cDNA expression cloning vectors, or other preferred expression vectors known and commercially available from vendors such as Invitrogen, (CA), Stratagene, (CA) or Clontech, (CA). Alternatively expression vectors developed by academic groups such as the pCMX vectors originally developed in the Evans lab (Willey et al. Genes & Development 9 1033-1045 (1995)) may also be used.

The transcriptional regulatory sequences in an expression cassette are selected by the practitioner based on the intended application; depending upon the specific use, transcription regulation can employ inducible, repressible, constitutive, cell-type specific, developmental stage-specific, sex-specific, or other desired type of promoter or control sequence.

Alternatively, the expression plasmid may comprise an activation sequence to activate or increase the expression of an endogenous chromosomal sequence. Such activation sequences include for example, a synthetic zinc finger motif (for example see U.S. Pat. Nos. 6,534,261 and 6,503,7171) or a strong promoter or enhancer sequence together with a targeting sequence to enable homologous or non-homologous recombination of the activating sequence upstream of the gene of interest.

Genes encoding the following full-length previously described proteins, which are suitable for use in the co-transfection studies and profiling the compounds described herein, include human LXR α (accession U22662), human LXR β (accession U07132), rat FXR (accession U18374), human FXR (accession NM_005123), human RXR α (accession NM_002957), human RXR β (accession XM_042579), human RXRγ (accession XM_053680), human PPARα (accession X57638) and human PPAR δ (accession U10375). All accession numbers in this application refer to GenBank accession numbers.

Reporter plasmids may be constructed using standard molecular biological techniques by placing cDNA encoding for the reporter gene downstream from a suitable minimal promoter. For example luciferase reporter plasmids may be constructed by placing cDNA encoding firefly luciferase (typically with SV40 small t intron and poly-A tail, (de Wet et al., (1987) Mol. Cell. Biol. 7 725-735) down stream from the herpes virus thymidine kinase promoter (located at nucleotides residues –105 to +51 of the thymidine kinase nucleotide sequence, obtained for example, from the plasmid pBLCAT2 (Luckow & Schutz (1987) Nucl. Acid. Res. 15 5490-5494)) which is linked in turn to the appropriate response element (RE).

The choice of hormone response element is dependent upon the type of assay to be used. In the case of the use of the full-length LXR α or LXR β a reporter plasmid comprising a known LXR RE would typically be used, such as for example in a reporter plasmid such as LXRExl-tk-luciferase, (see U.S. Pat. No. 5,747,661, which is hereby incorporated by reference). In the case of a LXR α or LXR β-LBD-Gal4 fusion, GAL4 Upstream Activating Sequences (UAS) would be used. Typically the GAL4 UAS would comprise the sequence 5'CGGRNNRCYNYNCNCCG-3', where Y=C or T, R=A or G, and N=A, C, T or G, and would be present as a tandem repeat of 4 copies.

Numerous methods of co-transfecting the expression and reporter plasmids are known to those of skill in the art and may be used for the co-transfection assay to introduce the plasmids into a suitable cell type. Typically such a cell will not endogenously express nuclear receptors that interact with the response elements used in the reporter plasmid.

Numerous reporter gene systems are known in the art and include, for example, alkaline phosphatase (see, Berger, J., et al., *Gene* (1988), Vol. 66, pp.1-10; and Kain, S. R., *Methods. Mol. Biol.* (1997), Vol. 63, pp. 49-60), β-galactosidase (See, U.S. Pat. No. 5,070,012, issued Dec. 3, 1991 to Nolan et al., and Bronstein, I., et al., *J. Chemilum. Biolum.* (1989), Vol. 4, pp. 99-111), chloramphenicol acetyltransferase (See, Gorman et al., *Mol. Cell Biol.* (1982), Vol. 2, pp. 1044-51), β-glucuronidase, peroxidase, β-lactamase (U.S. Pat. Nos. 5,741,657 and 5,955,604), catalytic antibodies, luciferases (U.S. Pat. Nos. 5,221,623; 5,683,888; 5,674,713; 5,650,289; and 5,843,746) and naturally fluorescent proteins (Tsien, R. Y., *Annu. Rev. Biochem.* (1998), Vol. 67, pp. 509-44).

The use of chimeras comprising the ligand binding domain (LBD) of the nuclear receptor of interest to a heterologous DNA binding domain (DBD) expands the versatility of cell based assays by directing activation of the nuclear receptor in question to defined DNA binding elements recognized by defined DNA binding domain (see WO95/18380). This assay expands the utility of cell based co-transfection assays in cases where the biological response or screening window using the native DNA binding domain is not satisfactory.

In general the methodology is similar to that used with the basic co-transfection assay, except that a chimeric construct is used in place of the full length nuclear receptor. As with the full length nuclear receptor, treatment of the transfected cells with an agonist for the nuclear receptor LBD increases the transcriptional activity of the heterologous DNA binding domain which is reflected by an increase in expression of the reporter gene as described above. Typically for such chimeric constructs, the DNA binding domains from defined nuclear receptors, or from yeast or bacterially derived transcriptional regulators such as members of the GAL 4 and Lex A/Umud super families are used.

A third cell based assay of utility for screening compounds of the present invention is a mammalian two-hybrid assay that measures the ability of the nuclear hormone receptor to interact with a cofactor in the presence of a ligand (see, for example, U.S. Pat. Nos. 5,667,973, 5,283, 173 and 5,468,614). The basic approach is to create three plasmid constructs that enable the interaction of the nuclear receptor with the interacting protein to be coupled to a transcriptional readout within a living cell. The first construct is an expression plasmid for expressing a fusion protein comprising the interacting protein, or a portion of that protein containing the interacting domain, fused to a GAL4 DNA binding domain. The second expression plasmid comprises DNA encoding the nuclear receptor of interest fused to a strong transcription activation domain such as VP16, and the third construct comprises the reporter plasmid comprising a reporter gene with a minimal promoter and GAL4 upstream activating sequences.

Once all three plasmids are introduced into a cell, the GAL4 DNA binding domain encoded in the first construct allows for specific binding of the fusion protein to GAL4 sites upstream of a minimal promoter. However because the GAL4 DNA binding domain typically has no strong transcriptional activation properties in isolation, expression of the reporter gene occurs only at a low level. In the presence of a ligand, the nuclear receptor-VP16 fusion protein can bind to the GAL4-interacting protein fusion protein bringing the strong transcriptional activator VP16 in close proximity to the GAL4 binding sites and minimal promoter region of the reporter gene. This interaction significantly enhances the transcription of the reporter gene which can be measured for various reporter genes as described above. Transcription of the reporter gene is thus driven by the interaction of the interacting protein and nuclear receptor of interest in a ligand dependent fashion.

Any compound which is a candidate for activation of LXR α or LXR β may be tested by these methods. Generally, compounds are tested at several different concentrations to optimize the chances that activation of the receptor will be detected and recognized if present. Typically assays are performed in triplicate and vary within experimental error by less than 15%. Each experiment is typically repeated three or more times with similar results.

Activity of the reporter gene can be conveniently normalized to the internal control and the data plotted as fold activation relative to untreated cells. A positive control compound (agonist) may be included along with DMSO as high and low controls for normalization of the assay data. Similarly, antagonist activity can be measured by determining the ability of a compound to competitively inhibit the activity of an agonist.

Additionally the compounds and compositions can be evaluated for their ability to increase or decrease the expression of genes known to be modulated by LXR $\alpha$ or $\beta$ and other nuclear receptors in vivo, using Northern-blot, RT PCR or oligonucleotide microarray analysis to analyze RNA levels. Western-blot analysis can be used to measure expression of proteins encoded by LXR target genes. Genes that are known to be regulated by the LXRs include the ATP binding cassette transporters ABCA1, ABCG1, ABCG5, ABCG8, the sterol response element binding protein 1c (SREBP1c) gene, stearoyl CoA desaturase 1 (SCD-1) and the apolipoprotein apoE gene (ApoE).

Established animal models exist for a number of diseases of direct relevance to the claimed compounds and these can be used to further profile and characterize the claimed compounds. These model systems include diabetic dislipidemia using Zucker (fa/fa) rats or (db/db) mice, spontaneous hyperlipidemia using apolipoprotein E deficient mice (ApoE$^{-/-}$), diet-induced hyperlipidemia using low density lipoprotein receptor deficient mice (LDR$^{-/-}$) and atherosclerosis using both the Apo E($^{-/-}$) and LDL($^{-/-}$) mice fed a western diet. (21% fat, 0.05% cholesterol). Additionally LXR or FXR animal models (e.g., knockout mice) can be used to further evaluate the present compounds and compositions in vivo (see, for example, Peet, et al., *Cell* (1998), Vol. 93, pp. 693-704, and Sinal, et al., *Cell* (2000), Vol. 102, pp. 731-744).

D. Administration of the Compounds of the Invention

Administration of the compounds of the invention, or their pharmaceutically acceptable salts, in pure form or in an appropriate pharmaceutical composition, can be carried out via any of the accepted modes of administration of agents for serving similar utilities. The pharmaceutical compositions of the invention can be prepared by combining a compound of the invention with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see *Remington's Pharmaceutical Sciences*, 18th Ed., (Mack Publishing Company, Easton, Pa., 1990). The composition to be administered will, in any event, contain a therapeutically effective amount of a compound of the invention, or a pharmaceutically acceptable salt thereof, for treatment of a disease-state associated with the activity of a nuclear receptor in accordance with the teachings of this invention.

A pharmaceutical composition of the invention may be in the form of a solid or liquid. In one aspect, the carrier(s) are particulate, so that the compositions are, for example, in tablet or powder form. The carrier(s) may be liquid, with the compositions being, for example, an oral syrup, injectable liquid or an aerosol, which is useful in, e.g., inhalatory administration.

When intended for oral administration, the pharmaceutical composition is preferably in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, e.g., a gelatin capsule, it may contain, in addition to materials of the above type, a liquid carrier such as polyethylene glycol or oil.

The pharmaceutical composition may be in the form of a liquid, e.g., an elixir, syrup, solution, emulsion or suspension. The liquid may be for oral administration or for delivery by injection, as two examples. When intended for oral administration, preferred composition contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid pharmaceutical composition of the invention intended for either parenteral or oral administration should contain an amount of a compound of the invention such that a suitable dosage will be obtained. Typically, this amount is at least 0.01% of a compound of the invention in the composition. When intended for oral administration, this amount may be varied to be between 0.1 and about 70% of the weight of the composition. Preferred oral pharmaceutical compositions contain between about 4% and about 50% of the compound of the invention. Preferred pharmaceutical compositions and preparations according to the present invention are prepared so that a parenteral dosage unit contains between 0.01 to 1% by weight of the compound of the invention.

The pharmaceutical composition of the invention may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention from about 0.1 to about 10% w/v (weight per unit volume).

The pharmaceutical composition of the invention may be intended for rectal administration, in the form, e.g., of a suppository, which will melt in the rectum and release the drug. The composition for rectal administration may contain an oleaginous base as a suitable nonirritating excipient. Such bases include, without limitation, lanolin, cocoa butter and polyethylene glycol.

The pharmaceutical composition of the invention may include various materials, which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule.

The pharmaceutical composition of the invention in solid or liquid form may include an agent that binds to the compound of the invention and thereby assists in the delivery of the compound. Suitable agents that may act in this capacity include a monoclonal or polyclonal antibody, a protein or a liposome.

The pharmaceutical composition of the invention may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of the invention may be delivered in single phase, bi-phasic, or tri-phasic systems in order to deliver the active ingredient(s). Delivery of the aerosol includes the necessary container, activators, valves, subcontainers, and the like, which together may form a kit. One skilled in the art, without undue experimentation may determine preferred aerosols.

The pharmaceutical compositions of the invention may be prepared by methodology well known in the pharmaceutical art. For example, a pharmaceutical composition intended to be administered by injection can be prepared by combining a compound of the invention with sterile, distilled water so as to form a solution. A surfactant may be added to facilitate the formation of a homogeneous solution or suspension. Surfactants are compounds that non-covalently interact with the compound of the invention so as to facilitate dissolution or homogeneous suspension of the compound in the aqueous delivery system.

The compounds of the invention, or their pharmaceutically acceptable salts, are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Generally, a therapeutically effective daily dose is from about 0.1 mg to about 20 mg/kg of body weight per day of a compound of the invention, or a pharmaceutically acceptable salt thereof; preferably, from about 0.1 mg to about 10 mg/kg of body weight per day; and most preferably, from about 0.1 mg to about 7.5 mg/kg of body weight per day.

Compounds of the invention, or pharmaceutically acceptable derivatives thereof, may also be administered simultaneously with, prior to, or after administration of one or more of the therapeutic agents described above in the Utility of the Compounds of the Invention. Such combination therapy includes administration of a single pharmaceutical dosage formulation which contains a compound of the invention and one or more additional active agents, as well as administration of the compound of the invention and each active agent in its own separate pharmaceutical dosage formulation. For example, a compound of the invention and an HMG-CoA reductase inhibitor can be administered to the patient together in a single oral dosage composition such as a tablet or capsule, or each agent administered in separate oral dosage formulations. Where separate dosage formulations are used, the compounds of the invention and one or more additional active agents can be administered at essentially the same time, i.e., concurrently, or at separately staggered times, i.e., sequentially; combination therapy is understood to include all these regimens.

Dosage information for HMG-CoA reductase inhibitors is well known in the art, since several HMG-CoA reductase inhibitors are marketed in the U.S. In particular, the daily dosage amounts of the HMG-CoA reductase inhibitor may be the same or similar to those amounts which are employed for anti-hypercholesterolemic treatment and which are described in the *Physicians' Desk Reference* (PDR). For example, see the 50th Ed. of the PDR, 1996 (Medical Economics Co); in particular, see at page 216 the heading "Hypolipidemics," sub-heading "HMG-CoA Reductase Inhibitors," and the reference pages cited therein. Preferably, the oral dosage amount of HMG-CoA reductase inhibitor is from about 1 to 200 mg/day and, more preferably, from about 5 to 160 mg/day. However, dosage amounts will vary depending on the potency of the specific HMG-CoA reductase inhibitor used as well as other factors as noted above. An HMG-CoA reductase inhibitor which has sufficiently greater potency may be given in sub-milligram daily dosages.

As examples, the daily dosage amount for simvastatin may be selected from 5 mg, 10 mg, 20 mg, 40 mg, 80 mg and 160 mg for lovastatin, 10 mg, 20 mg, 40 mg and 80 mg; for fluvastatin sodium, 20 mg, 40 mg and 80 mg; and for pravastatin sodium, 10 mg, 20 mg, and 40 mg. The daily dosage amount for atorvastatin calcium may be in the range of from 1 mg to 160 mg and, more particularly, from 5 mg to 80 mg. Oral administration may be in a single or divided doses of two, three, or four times daily, although a single daily dose of the HMG-CoA reductase inhibitor is preferred.

E. Preferred Embodiments of the Compounds of the Invention

Of the compounds of the invention, as set forth above in the Summary of the Invention, a preferred group of compounds are those compounds wherein:

n is 0 to 4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$S(O)_tR^4$ (where t is 0 to 2), and —$R^6$—$S(O)_pN(R^4)_2$ (where p is 1 or 2);

$R^2$ is alkynyl optionally substituted with —$Si(R^4)_3$, hydroxyalkyl, optionally substituted aryl, or optionally substituted cycloalkyl, $R^3$ is alkyl or cycloalkylalkyl optionally substituted with one or more substituents selected from the group consisting of alkyl, alkenyl, cyano, nitro, halo, haloalkyl, haloalkenyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2), or $R^3$ is aralkyl wherein the aryl group of the aralkyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R_6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2 );

or $R^3$ is heteroarylalkyl wherein the heteroaryl group of the heteroarylakyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen or aralkyl.

Of this preferred group of compounds, a preferred subgroup of compounds are those compounds wherein:

n is 0 to 4;

each $R^1$ is independently selected from the group consisting of alkyl, halo, haloalkyl or hydroxy;

$R^2$ is alkynyl optionally substituted with —$Si(R^4)_3$, hydroxyalkyl, optionally substituted aryl, or optionally substituted cycloalkyl, $R^3$ is benzyl optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N[S(O)_tR^4_2]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

$R^5$ is selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen.

Of this preferred subgroup of compounds, a preferred class of compounds are those compounds wherein:

n is 0;

$R^2$ is ethynyl optionally substituted with —$Si(R^4)_3$, hydroxyalkyl, phenyl or cyclohexyl optionally substituted by hydroxy, $R^3$ is benzyl optionally substituted with one or more substituents selected from the group consisting of alkyl and aryl; and each $R^4$ is independently selected from the group consisting of hydrogen, methyl, phenyl and benzyl.

Of this preferred class of compounds, preferred compounds are selected from the group consisting of the following:

2-biphenyl-4-ylmethyl-3-trimethylsilanylethynyl-2H-isoquinolin-1-one;

2-(2,4-dimethylbenzyl)-3-(3-hydroxy-3-methylbut-1-ynyl)-2H-isoquinolin-1-one; 2-(2,4-dimethylbenzyl)-3-trimethylsilanylethynyl-2H-isoquinolin-1-one;

2-benzyl-3-(3-hydroxy-3-methylbut-1-ynyl)-2H-isoquinolin-1-one;

3-(3-hydroxy-3-methylbut-1-ynyl)-2-(4-methylbenzyl)-2H-isoquinolin-1-one;

2-benzyl-3-trimethylsilanylethynyl-2H-isoquinolin-1-one;

2-(4-methylbenzyl)-3-trimethylsilanylethynyl-2H-isoquinolin-1-one;

2-(2,4-dimethylbenzyl)-3-phenylethynyl-2H-isoquinolin-1-one; and 2-(2,4-dimethylbenzyl)-3-(1-hydroxycyclohexylethynyl)-2H-isoquinolin-1-one.

Of the compounds of the invention as set forth above in the Summary of the Invention, another preferred group of compounds are those compounds wherein:

n is 0 to 4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R^6-S(O)_tR^4$ (where t is 0 to 2), and $-R^6-S(O)_pN(R^4)_2$ (where p is 1 or 2);

$R^2$ is heteroaryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R_6-N[S(O)_tR^4]_2$ (where t is 0 to 2), $-R^6-N(R^4)(S(O)_tR^4)$ (where t is 0 to 2), $-R^6-S(O)_tR^4$ (where t is 0 to 2), and $-R^6-S(O)_pN(R^4)_2$ (where p is 1 or 2);

$R^3$ is alkyl or cycloalkylalkyl optionally substituted with one or more substituents selected from the group consisting of alkyl, alkenyl, cyano, nitro, halo, haloalkyl, haloalkenyl, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R^6-N[S(O)_tR^4]_2$ (where t is 0 to 2), $-R^6-N(R^4)(S(O)_tR^4)$ (where t is 0 to 2), $-R^6-S(O)_tR^4$ (where t is 0 to 2), and $-R^6-S(O)_pN(R^4)_2$ (where p is 1 or 2);

or $R^3$ is aralkyl wherein the aryl group of the aralkyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R_6-N[S(O)_tR^4]_2$ (where t is 0 to 2), $-R^6-N(R^4)(S(O)_tR^4)$ (where t is 0 to 2), $-R^6-S(O)_tR^4$ (where t is 0 to 2), and $-R^6-S(O)_pN(R^4)_2$ (where p is 1 or 2);

or $R^3$ is heteroarylalkyl wherein the heteroaryl group of the heteroarylakyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R^6-N[S(O)_tR^4]_2$ (where t is 0 to 2), $-R^6-N(R^4)(S(O)_tR^4)$ (where t is 0 to 2), $-R^6-S(O)_tR^4$ (where t is 0 to 2), and $-R^6-S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen or aralkyl.

Of this preferred group of compounds, a preferred subgroup of compounds are those compounds wherein:

n is 0 to 4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R^6-S(O)_tR^4$ (where t is 0 to 2), and $-R^6-S(O)_pN(R^4)_2$ (where p is 1 or 2);

$R^2$ is heteroaryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R_6-N[S(O)_tR^4]_2$ (where t is 0 to 2), $-R^6-N(R^4)(S(O)_tR^4)$ (where t is 0 to 2), $-R^6-S(O)_tR^4$ (where t is 0 to 2), and $-R^6-S(O)_pN(R^4)_2$ (where p is 1 or 2);

$R^3$ is aralkyl wherein the aryl group of the aralkyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R_6-N[S(O)_tR^4]_2$ (where t is 0 to 2), $-R^6-N(R^4)(S(O)_tR^4)$ (where t is 0 to 2), $-R^6-S(O)_tR^4$ (where t is 0 to 2), and $-R^6-S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen or aralkyl.

Of this preferred subgroup of compounds, a preferred class of compounds are those compounds wherein:

n is 0 to 4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R^6-S(O)_tR^4$ (where t is 0 to 2), and $-R^6-S(O)_pN(R^4)_2$ (where p is 1 or 2);

$R^2$ is heteroaryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^6-OR^4$, $-R^6-N(R^4)_2$, $-R^6-C(O)OR^4$, $-R^6-C(O)N(R^4)_2$, —$R^6$—$N(R^4)C(O)R^4$, —$R^6$—$N(R^4)C(O)OR^5$, —$R^6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

$R^3$ is benzyl optionally substituted with one or more substituents selected from the group consisting of alkyl, aryl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

$R^5$ is selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen.

Of this class of compounds, a preferred subclass are those compounds wherein:

n is 0 to 4;

each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;

$R^2$ is thiophenyl, benzothiophenyl, furanyl or benzofuranyl, each optionally substituted with one or more substituents selected from the group consisting of alkyl, cyano, nitro, halo, haloalkyl, optionally substituted aryl, optionally substituted aralkyl, optionally substituted heteroaryl, optionally substituted heteroarylalkyl, —$R^6$—$OR^4$, —$R^6$—$N(R^4)_2$, —$R^6$—$C(O)OR^4$, and —$R^6$—$C(O)N(R^4)_2$;

$R^3$ is benzyl optionally substituted with one or more substituents selected from the group consisting of alkyl, aryl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^6$ is a direct bond or a straight or branched alkylene chain; and $R^7$ is hydrogen.

Of this subclass of compounds, a preferred set of compounds are those compounds wherein:

n is 0 to 4;

each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;

$R^2$ is thiophenyl, benzothiophenyl, furanyl or benzofuranyl, each of which are optionally substituted with one or more substituents independently selected from the group consisting of halo, —$R^6$—$OR^4$, optionally substituted phenyl and optionally substituted pyridinyl;

$R^3$ is benzyl optionally substituted with one or more substituents selected from the group consisting of alkyl, aryl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, haloalkyl, aryl, and aralkyl;

each $R^6$ is a direct bond or a straight or branched alkylene chain; and $R^7$ is hydrogen.

Of this preferred set of compounds, a preferred subset of compounds are those compounds wherein:

n is 0 to 4;

each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;

$R^2$ is thiophenyl, benzothiophenyl, furanyl or benzofuranyl, each of which are optionally substituted with one or more substituents independently selected from the group consisting of halo and —$R^6$—$OR^4$;

$R^3$ is benzyl optionally substituted with one or more substituents selected from the group consisting of alkyl, aryl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, haloalkyl, aryl, and aralkyl;

each $R^6$ is a direct bond or a straight or branched alkylene chain; and $R^7$ is hydrogen.

Of this preferred subset of compounds, preferred compounds are selected from the group consisting of the following:

2-benzyl-3-thiophen-2-yl-2H-isoquinolin-1-one;
2-benzyl-3-furan-3-yl-2H-isoquinolin-1-one;
2-(2,4-dimethylbenzyl)-3-thiophen-3-yl-2H-isoquinolin-1-one;
2-(2,4-dimethylbenzyl)-3-furan-2-yl-2H-isoquinolin-1-one;
2-benzyl-3-thiophen-3-yl-2H-isoquinolin-1-one;
2-(2,4-dimethylbenzyl)-3-thiophen-2-yl-2H-isoquinolin-1-one;
3-benzo[b]thiophen-2-yl-2-(4-methylbenzyl)-2H-isoquinolin-1-one;
3-benzofuran-2-yl-2-(4-methylbenzyl)-2H-isoquinolin-1-one;
3-benzofuran-2-yl-2-(2,4-dimethylbenzyl)-2H-isoquinolin-1-one;
3-benzo[b]thiophen-2-yl-2-(2,4-dimethylbenzyl)-2H-isoquinolin-1-one; and
3-(5-bromothiophen-2-yl)-8-chloro-2-(2,4-difluorobenzyl)-2H-isoquinolin-1-one.

Of the preferred set of compounds described above, another preferred subset of compounds are those compounds wherein:

n is 0 to 4;

each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;

$R^2$ is thiophenyl or furanyl, each of which is substituted with phenyl or pyridinyl, where the phenyl and the pyridinyl are each optionally substituted with one or more substituents selected from the group consisting of alkyl, halo, haloalkyl, cyano, nitro, —$R^6$—$OR^4$, —$R^6$—$N(R^4)_2$, —$R^6$—$C(O)OR^4$, —$R^6$—$C(O)N(R^4)_2$—$R^6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 to 2);

$R^3$ is benzyl optionally substituted with one or more substituents selected from the group consisting of alkyl, aryl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, haloalkyl, aryl, and aralkyl;

each $R^6$ is a direct bond or a straight or branched alkylene chain; and $R^7$ is hydrogen.

Of this preferred subset of compounds, preferred compounds are selected from the group consisting of the following:

8-chloro-2-(2,4-difluorobenzyl)-3-[5-(3,4-dimethoxyphenyl)thiophen-2-yl]-2H-isoquinolin-1-one;

3-[5-(3,5-bis-trifluoromethylphenyl)thiophen-2-yl]-8-chloro-2-(2,4-difluorobenzyl)-2H-isoquinolin-1-one;

8-chloro-2-(2,4-difluorobenzyl)-3-[5-(4-methanesulfonylphenyl)thiophen-2-yl]-2H-isoquinolin-1-one;

8-chloro-3-[5-(3-chloro-4-ethoxyphenyl)thiophen-2-yl]-2-(2,4-difluorobenzyl)-2H-isoquinolin-1-one;

8-chloro-3-[5-(3-chloro-4-ethoxyphenyl)furan-2-yl]-2-(2,4-difluorobenzyl)-2H-isoquinolin-1-one;

3-[5-(3,5-bis-trifluoromethylphenyl)furan-2-yl]-8-chloro-2-(2,4-difluorobenzyl)-2H-isoquinolin-1-one;

8-chloro-2-(2,4-difluorobenzyl)-3-[5-(4-methanesulfonylphenyl)furan-2-yl]-2H-isoquinolin-1-one;

8-chloro-3-[4-(3-chloro-4-ethoxyphenyl)thiophen-2-yl]-2-(2,4-difluorobenzyl)-2H-isoquinolin-1-one;

3-[4-(3,5-bis-trifluoromethylphenyl)thiophen-2-yl]-8-chloro-2-(2,4-difluorobenzyl)-2H-isoquinolin-1-one;

8-chloro-2-(2,4-difluorobenzyl)-3-[4-(4-methanesulfonylphenyl)thiophen-2-yl]-2H-isoquinolin-1-one;

3-[4-(4-amino-3-trifluoromethylphenyl)thiophen-2-yl]-8-chloro-2-(2,4-difluorobenzyl)-2H-isoquinolin-1-one;

3-[4-(4-amino-3-chloro-phenyl)thiophen-2-yl]-8-chloro-2-(2,4-difluorobenzyl)-2H-isoquinolin-1-one;

8-chloro-2-(2,4-difluorobenzyl)-3-[4-(4-ethoxy-3-trifluoromethylphenyl)thiophen-2-yl]-2H-isoquinolin-1-one;

8-chloro-2-(2,4-difluorobenzyl)-3-[5-(4-ethoxy-3-trifluoromethylphenyl)thiophen-2-yl]-2H-isoquinolin-1-one;

3-[5-(4-amino-3-trifluoromethylphenyl)thiophen-2-yl]-8-chloro-2-(2,4-difluorobenzyl)-2H-isoquinolin-1-one;

3-[5-(4-amino-3-chloro-phenyl)thiophen-2-yl]-8-chloro-2-(2,4-difluorobenzyl)-2H-isoquinolin-1-one;

8-chloro-3-[4-(3-chloro-4-diethylamino-phenyl)thiophen-2-yl]-2-(2,4-difluorobenzyl)-2H-isoquinolin-1-one;

8-chloro-3-[4-(3-chloro-4-ethylamino-phenyl)thiophen-2-yl]-2-(2,4-difluorobenzyl)-2H-isoquinolin-1-one;

8-chloro-3-[4-(3-chloro-4-ethoxyphenyl)furan-2-yl]-2-(2,4-difluorobenzyl)-2H-isoquinolin-1one;

3-[4-(3,5-bis-trifluoromethylphenyl)furan-2-yl]-8-chloro-2-(2,4-difluorobenzyl)-2H-isoquinolin-1-one;

8-chloro-2-(2,4-difluorobenzyl)-3-[5-(4-ethylamino-3-trifluoromethylphenyl)thiophen-2-yl]-2H-isoquinolin-1-one;

8-chloro-3-[5-(3-trifluoromethyl-4-(bis-methanesulfonylamino)-phenyl)thiophen-2-yl]-2-(2,4-difluorobenzyl)-2H-isoquinolin-1-one;

8-chloro-2-(2,4-difluorobenzyl)-3-[4-(4-methanesulfonylphenyl)furan-2-yl]-2H-isoquinolin-1-one;

8-chloro-2-(2,4-difluorobenzyl)-3-[5-(3-ethanesulfonyl-5-trifluoromethylphenyl)thiophen-2-yl]-2H-isoquinolin-1-one;

8-chloro-2-(2,4-difluorobenzyl)-3-[4-(3-ethanesulfonyl-5-trifluoromethylphenyl)furan-2-yl]-2H-isoquinolin-1-one;

3-[4-(4-amino-3-trifluoromethylphenyl)furan-2-yl]-8-chloro-2-(2,4-difluorobenzyl)-2H-isoquinolin-1-one;

8-chloro-2-(2,4-difluorobenzyl)-3-[5-(3-ethylsulfanyl-5-trifluoromethylphenyl)furan-2-yl]-2H-isoquinolin-1-one;

8-chloro-2-(2,4-difluorobenzyl)-3-[5-(3-ethanesulfonyl-5-trifluoromethylphenyl)furan-2-yl]-2H-isoquinolin-1-one;

8-chloro-2-(2,4-difluorobenzyl)-3-[4-(4-ethylamino-3-trifluoromethylphenyl)furan-2-yl]-2H-isoquinolin-1-one;

8-chloro-2-(2,4-difluorobenzyl)-3-[5-(6-ethoxypyridin-3-yl)-thiophen-2-yl]-2H-isoquinolin-1-one; and 5-{5-[8-chloro-2-(2,4-difluorobenzyl)-1-oxo-1,2-dihydro-isoquinolin-3-yl]-thiophen-2-yl}-2-ethoxy-nicotinonitrile.

Of the compounds of the invention as set forth above in the Summary of the Invention, another preferred group of compounds are those compounds wherein:

n is 0 to 4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R^6-S(O)_tR^4$ (where t is 0 to 2), and $-R^6-S(O)_pN(R^4)_2$ (where p is 1 or 2);

$R^2$ is aryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R^6-N[S(O)_tR^4]_2$ (where t is 0 to 2), $-R^6-N(R^4)(S(O)_tR^4)$ (where t is 0 to 2), $-R^6-S(O)_tR^4$ (where t is 0 to 2), and $-R_6-S(O)_pN(R^4)_2$ (where p is 1 or 2);

$R^3$ is alkyl or cycloalkylalkyl optionally substituted with one or more substituents selected from the group consisting of alkyl, alkenyl, cyano, nitro, halo, haloalkyl, haloalkenyl, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R^6-N[S(O)_tR^4]_2$ (where t is 0 to 2), $-R^6-N(R^4)(S(O)_tR^4)$ (where t is 0 to 2), $-R^6-S(O)_tR^4$ (where t is 0 to 2), and $-R^6-S(O)_pN(R^4)_2$ (where p is 1 or 2);

or $R^3$ is aralkyl wherein the aryl group of the aralkyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R_6-N[S(O)_tR^4]_2$ (where t is 0 to 2), $-R^6-N(R^4)(S(O)_tR^4)$ (where t is 0 to 2), $-R^6-S(O)_tR^4$ (where t is 0 to 2), and $-R^6-S(O)_pN(R^4)_2$ (where p is 1 or 2);

or $R^3$ is heteroarylalkyl wherein the heteroaryl group of the heteroarylakyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, $-R^6-OR^4$, $-R^6-N(R^4)_2$, $-R^6-C(O)OR^4$, $-C(O)N(R^4)_2$, $-R^6-N(R^4)C(O)R^4$, $-R^6-N(R^4)C(O)OR^5$, $-R^6-N[S(O)_tR^4]_2$ (where t is 0 to 2), $-R^6-N(R^4)(S(O)_tR^4)$ (where t is 0 to 2), $-R^6-S(O)_tR^4$ (where t is 0 to 2), and $-R^6-S(O)_pN(R^4)_2$(where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen or aralkyl.

Of this preferred group of compounds, a preferred subgroup of compounds are those compounds wherein:

n is 0 to 4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$S(O)_tR^4$ (where t is 0 to 2), and —$R^6$—$S(O)_pN(R^4)_2$ (where p is 1 or 2);

$R^2$ is aryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$—$R^6$—$N(R^4)C(O)R^4$, —$R^6$—$N(R^4)C(O)OR^5$, —$R^6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

$R^3$ is aralkyl wherein the aryl group of the aralkyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R_6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen or aralkyl.

Of this preferred subgroup of compounds, a preferred class of compounds are those compounds wherein:

n is 0 to 4;

each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;

$R^2$ is phenyl optionally substituted with one or more substituents selected from the group consisting of alkyl, cyano, nitro, halo, haloalkyl, optionally substituted aryl, optionally substituted aralkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, and —$R^6$—$N(R)C(O)R^4$;

$R^3$ is benzyl optionally substituted with one or more substituents selected from the group consisting of alkyl, aryl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, alkenyl, haloalkyl, hydroxyalkyl, cycloalkyl, cycloalkylalkyl, aryl, and aralkyl;

each $R^6$ is a direct bond or a straight or branched alkylene chain; and $R^7$ is hydrogen.

Of this class of compounds, a preferred subclass of compounds are those compounds wherein:

n is 0 or 1;

$R^1$ is alkyl or halo;

$R^2$ is phenyl optionally substituted with one or more substituents selected from the group consisting of alkyl, optionally substituted aryl and optionally substituted aralkyl; and $R^3$ is benzyl optionally substituted with one or more substituents selected from the group consisting of alkyl, halo and aryl.

Of this preferred subclass of compounds, preferred compounds are selected from the group consisting of the following:

2-biphenyl-4-ylmethyl-3-m-tolyl-2H-isoquinolin-1-one;
2-(2,4-dimethylbenzyl)-3-m-tolyl-2H-isoquinolin-1-one;
2-benzyl-3-m-tolyl-2H-isoquinolin-1-one;
2-(2,4-dimethylbenzyl)-3-(3,5-dimethylphenyl)-2H-isoquinolin-1-one;
2-(2,4-dimethylbenzyl)-3-phenyl-2H-isoquinolin-1-one;
5-chloro-2-(2,4-dimethylbenzyl)-3-m-tolyl-2H-isoquinolin-1-one;
5-chloro-2-(4-methylbenzyl)-3-m-tolyl-2H-isoquinolin-1-one;
5-chloro-2-(2,4-dimethylbenzyl)-3-phenyl-2H-isoquinolin-1-one;
5-chloro-2-(4-methylbenzyl)-3-phenyl-2H-isoquinolin-1-one;
8-chloro-2-(2,4-dimethylbenzyl)-3-phenyl-2H-isoquinolin-1-one;
8-chloro-2-(2,4-dimethylbenzyl)-3-m-tolyl-2H-isoquinolin-1-one;
2-benzyl-8-chloro-3-m-tolyl-2H-isoquinolin-1-one;
2-benzyl-8-chloro-3-phenyl-2H-isoquinolin-1-one;
2-benzyl-8-methyl-3-m-tolyl-2H-isoquinolin-1-one;
8-methyl-2-(4-methylbenzyl)-3-m-tolyl-2H-isoquinolin-1-one;
2-(2,4-dimethylbenzyl)-8-methyl-3-m-tolyl-2H-isoquinolin-1-one;
2-benzyl-8-methyl-3-phenyl-2H-isoquinolin-1-one;
8-methyl-2-(4-methylbenzyl)-3-phenyl-2H-isoquinolin-1-one;
2-(2,4-dimethylbenzyl)-8-methyl-3-phenyl-2H-isoquinolin-1-one;
2-(2,4-dimethylbenzyl)-7-methyl-3-phenyl-2H-isoquinolin-1-one;
2-(2,4-dimethylbenzyl)-7-methyl-3-m-tolyl-2H-isoquinolin-1-one;
7-methyl-2-(4-methylbenzyl)-3-phenyl-2H-isoquinolin-1-one;
7-methyl-2-(4-methylbenzyl)-3-m-tolyl-2H-isoquinolin-1-one;
7-chloro-2-(2,4-dimethylbenzyl)-3-m-tolyl-2H-isoquinolin-1-one;
2-benzyl-7-methyl-3-m-tolyl-2H-isoquinolin-1-one;
2-benzyl-7-methyl-3-phenyl-2H-isoquinolin-1-one;
2-benzyl-6-methyl-3-m-tolyl-2H-isoquinolin-1-one;

2-benzyl-6-methyl-3-phenyl-2H-isoquinolin-1-one;
2-(2,4-dimethylbenzyl)-6-methyl-3-phenyl-2H-isoquinolin-1-one;
6-methyl-2-(4-methylbenzyl)-3-m-tolyl-2H-isoquinolin-1-one;
6-methyl-2-(4-methylbenzyl)-3-phenyl-2H-isoquinolin-1-one;
7-chloro-2-(2,4-dimethylbenzyl)-3-phenyl-2H-isoquinolin-1-one;
2-(4-methylbenzyl)-3-phenyl-2H-isoquinolin-1-one;
2-benzyl-3-phenyl-2H-isoquinolin-1-one;
3-(4-benzylphenyl)-2-(2,4-dimethylbenzyl)-8-methyl-2H-isoquinolin-1-one;
8-chloro-2-(2,4-difluorobenzyl)-3-(4'-methanesulfonylbiphenyl-3-yl)-2H-isoquinolin-1-one;
8-chloro-2-(2,4-difluorobenzyl)-3-(3'-ethanesulfonyl-5'-trifluoromethyl-biphenyl-3-yl)-2H-isoquinolin-1-one;
8-chloro-2-(2,4-difluorobenzyl)-3-[3-(6-ethoxypyridin-3-yl)-phenyl]-2H-isoquinolin-1-one;
5-{3-[8-chloro-2-(2,4-difluorobenzyl)-1-oxo-1 ,2-dihydroisoquinolin-3-yl]-phenyl}-2-ethoxy-nicotinonitrile;
3-(3',5'-bis-trifluoromethylbiphenyl-3-yl)-8-chloro-2-(2,4-difluorobenzyl)-2H-isoquinolin-1-one
8-chloro-3-(3'-chloro-4'-ethoxybiphenyl-3-yl)-2-(2,4-difluorobenzyl)-2H-isoquinolin-1-one Of the preferred subgroup of compounds described above, another preferred class of compounds are those compounds wherein:

n is 0 to 4;
each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;
$R^2$ is phenyl optionally substituted with one or more substituents selected from the group consisting of alkyl, —$R^6$—$OR^4$, and —$R^6$—$S(O)_tR^4$ (where t is 0 to 2);
$R^3$ is benzyl optionally substituted with one or more substituents selected from the group consisting of alkyl, aryl, aralkyl, cyano, nitro, halo, haloalkyl, cycloalkyl, heterocyclyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$S(O)_tR^4$ (where t is 0 to 2), and —$R^6$—$S(O)_pN(R^4)_2$ (where p is 1 or 2);
each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;
each $R^5$ is independently selected from the group consisting of hydrogen, alkyl, alkenyl, haloalkyl, hydroxyalkyl, cycloalkyl, cycloalkylalkyl, and aralkyl;
each $R^6$ is a direct bond or a straight or branched alkylene chain; and
$R^7$ is hydrogen or aralkyl.

Of this preferred class of compounds, a preferred subclass of compounds are those compounds wherein:

n is 0 to 4;
each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;
$R^2$ is phenyl optionally substituted with one or more substituents selected from the group consisting of alkyl, —$R$—$OR^4$, and —$R^6$—$S(O)_tR^4$ (where t is 0 to 2);
$R^3$ is benzyl optionally substituted with one or more substituents selected from the group consisting of alkyl, halo, and haloalkyl;
each $R^4$ is independently selected from the group consisting of hydrogen, alkyl, optionally substituted aryl, optionally substituted aralkyl, optionally substituted heterocyclyl and optionally substituted heteroaryl;
each $R^5$ is a direct bond; and
$R^7$ is hydrogen or aralkyl.

Of this preferred subclass of compounds, preferred compounds are those compounds selected from the group consisting of the following:

2-benzyl-3-(4-hydroxy-3,5-dimethylphenyl)-2H-isoquinolin-1-one;
2-(2,4-dimethylbenzyl)-3-(4-hydroxy-3,5-dimethylphenyl)-2H-isoquinolin-1-one;
2-(2,4-dimethylbenzyl)-3-(4-methoxyphenyl)-2H-isoquinolin-1-one;
2-benzyl-3-(4-hydroxyphenyl)-2H-isoquinolin-1-one;
2-(2,4-dimethylbenzyl)-3-(4-hydroxyphenyl)-2H-isoquinolin-1-one;
2-(2,4-dimethylbenzyl)-3-(4-hydroxy-3-methoxyphenyl)-2H-isoquinolin-1-one;
2-(2,4-dimethylbenzyl)-3-[3-methyl-4-(tetrahydropyran-2-yloxy)phenyl]-2H-isoquinolin-1-one;
2-(2,4-dimethylbenzyl)-3-(4-hydroxy-3-methylphenyl)-2H-isoquinolin-1-one;
2-(4-methylbenzyl)-3-(4-phenoxyphenyl)-2H-isoquinolin-1-one;
2-(2,4-dimethylbenzyl)-3-(4-phenoxyphenyl)-2H-isoquinolin-1-one;
2-(2,4-dimethylbenzyl)-3-(4-methylsulfanylphenyl)-2H-isoquinolin-1-one;
2-(4-methyl-benzyl)-3-(4-methylsulfanylphenyl)-2H-isoquinolin-1-one;
2-(2,4-dimethylbenzyl)-3-(3-methyl-4-phenoxyphenyl)-2H-isoquinolin-1-one;
2-benzyl-3-(4-phenoxyphenyl)-2H-isoquinolin-1-one;
5-chloro-2-(2,4-dimethylbenzyl)-3-(4-phenoxyphenyl)-2H-isoquinolin-1-one;
5-chloro-2-(4-methylbenzyl)-3-(4-phenoxyphenyl)-2H-isoquinolin-1-one;
2-(2,4-dimethylbenzyl)-5-fluoro-3-(4-phenoxyphenyl )-2H-isoquinolin-1-one;
2-benzyl-5-fluoro-3-(4-phenoxyphenyl)-2H-isoquinolin-1-one;
8-chloro-2-(2,4-dimethylbenzyl)-3-(4-phenoxyphenyl)-2H-isoquinolin-1-one;
2-benzyl-8-chloro-3-(4-phenoxyphenyl)-2H-isoquinolin-1-one;
2-benzyl-8-methyl-3-(4-phenoxyphenyl)-2H-isoquinolin-1-one;
8-methyl-2-(4-methylbenzyl)-3-(4-phenoxyphenyl)-2H-isoquinolin-1-one;
2-(2,4-dimethylbenzyl)-8-methyl-3-(4-phenoxyphenyl)-2H-isoquinolin-1-one;
2-(2,4-dimethylbenzyl)-7-methyl-3-(4-phenoxyphenyl)-2H-isoquinolin-1-one;
7-methyl-2-(4-methylbenzyl)-3-(4-phenoxyphenyl)-2H-isoquinolin-1-one;
2-benzyl-7-methyl-3-(4-phenoxyphenyl)-2H-isoquinolin-1-one;
2-benzyl-6-methyl-3-(4-phenoxyphenyl)-2H-isoquinolin-1-one;
2-(2,4-dimethylbenzyl)-6-methyl-3-(4-phenoxyphenyl)-2H-isoquinolin-1-one;
6-methyl-2-(4-methylbenzyl)-3-(4-phenoxyphenyl)-2H-isoquinolin-1-one;
7-chloro-2-(2,4-dimethylbenzyl)-3-(4-phenoxyphenyl)-2H-isoquinolin-1-one;

2-benzyl-7-chloro-3-(4-phenoxyphenyl)-2H-isoquinolin-1-one;
2-benzyl-6-chloro-3-(4-phenoxyphenyl)-2H-isoquinolin-1-one;
6-chloro-2-(2,4-dimethylbenzyl)-3-(4-phenoxyphenyl)-2H-isoquinolin-1-one;
2-benzyl-6,8-dimethyl-3-(4-phenoxyphenyl)-2H-isoquinolin-1-one;
2-(2,4-dimethylbenzyl)-6,8-dimethyl-3-(4-phenoxyphenyl)-2H-isoquinolin-1-one;
2-benzyl-5-methyl-3-(4-phenoxyphenyl)-2H-isoquinolin-1-one;
2-benzyl-5,6,7,8-tetramethyl-3-(4-phenoxyphenyl)-2H-isoquinolin-1-one;
2-(2,4-dimethylbenzyl)-5-methyl-3-(4-phenoxyphenyl)-2H-isoquinolin-1-one;
2-benzyl-8-methoxy-3-(4-phenoxyphenyl)-2H-isoquinolin-1-one;
2-(2,4-dimethylbenzyl)-8-fluoro-3-(4-phenoxyphenyl)-2H-isoquinolin-1-one;
8-chloro-2-(2,4-dichloro-benzyl)-3-(4-phenoxyphenyl)-2H-isoquinolin-1-one;
2-benzyl-8-fluoro-3-(4-phenoxyphenyl)-2H-isoquinolin-1-one;
2-(2,4-dimethylbenzyl)-3-(4-phenoxyphenyl)-8-trifluoromethyl-2H-isoquinolin-1-one;
2-(2,4-dimethylbenzyl)-8-methoxy-3-(4-phenoxyphenyl)-2H-isoquinolin-1-one;
8-chloro-2-(2,4-difluorobenzyl)-3-(4-phenoxyphenyl)-2H-isoquinolin-1-one;
7,8-dichloro-2-(2,4-dimethylbenzyl)-3-(4-phenoxyphenyl)-2H-isoquinolin-1-one;
8-chloro-2-(2,4-difluorobenzyl)-5-methyl-3-(4-phenoxyphenyl)-2H-isoquinolin-1-one;
6,7-dichloro-2-(2,4-difluorobenzyl)-3-(4-phenoxyphenyl)-2H-isoquinolin-1-one;
8-chloro-2-(2-chloro-4-fluoro-benzyl)-3-(4-phenoxyphenyl)-2H-isoquinolin-1-one;
5,6-dichloro-2-(2,4-difluorobenzyl)-3-(4-phenoxyphenyl)-2H-isoquinolin-1-one;
2-{4-[8-chloro-2-(2,4-difluorobenzyl)-1-oxo-1,2-dihydro-isoquinolin-3-yl]-phenoxy}-nicotinonitrile;
8-chloro-2-(2,4-difluorobenzyl)-3-(4-hydroxyphenyl)-2H-isoquinolin-1-one;
8-chloro-2-(2,4-difluorobenzyl)-3-[4-(pyrazin-2-yloxy)phenyl]-2H-isoquinolin-1-one;
2-{4-[2-(2,4-difluorobenzyl)-7-fluoro-1-oxo-1,2-dihydro-isoquinolin-3-yl]-phenoxy}-nicotinonitrile;
2-(2,4-difluorobenzyl)-7-fluoro-3-[4-(pyrazin-2-yloxy)phenyl]-2H-isoquinolin-1-one;
2-(2,4-difluorobenzyl)-7-fluoro-3-(4-phenoxyphenyl)-2H-isoquinolin-1-one;
2-(2,4-difluorobenzyl)-5-fluoro-3-[4-(pyrazin-2-yloxy)phenyl]-2H-isoquinolin-1-one;
2-{4-[2-(2,4-difluorobenzyl)-5-fluoro-1-oxo-1,2-dihydro-isoquinolin-3-yl]-phenoxy}-nicotinonitrile; and
2-(2,4-difluorobenzyl)-5-fluoro-3-(4-phenoxyphenyl)-2H-isoquinolin-1-one.

Of the preferred subgroup of compounds described above, another preferred class of compounds are those compounds wherein:
n is O or 1;
$R^1$ is alkyl or halo;
$R^2$ is phenyl optionally substituted with one or more substituents selected from the group consisting of cyano, halo, haloalkyl, —$R^6$—$OR^4$, —$R^6$—$N(R^4)_2$, —$R^6$—$C(O)OR^4$, and —$R^6$—$N(R^4)C(O)R^4$;

$R^3$ is benzyl optionally substituted with one or more substituents selected from the group consisting of alkyl, aryl, aralkyl, cyano, nitro, halo, haloalkyl, cycloalkyl, heterocyclyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R$—$S(O)_tR^4$ (where t is 0 to 2), and —$R^6$—$S(O)_pN(R^4)_2$ (where p is 1 or 2);
each $R^4$ is independently selected from the group consisting of hydrogen, alkyl, alkenyl, haloalkyl, hydroxyalkyl, cycloalkyl, cycloalkylalkyl, aryl, and aralkyl;
each $R^5$ is independently selected from the group consisting of hydrogen, alkyl, alkenyl, haloalkyl, hydroxyalkyl, cycloalkyl, cycloalkylalkyl, and aralkyl;
each $R^6$ is a direct bond or a straight or branched alkylene chain; and
$R^7$ is hydrogen or aralkyl.

Of this preferred class of compounds, a preferred subclass of compounds are those compounds wherein:
n is 0 or 1;
$R^1$ is alkyl or halo;
$R^2$ is phenyl optionally substituted with one or more substituents selected from the group consisting of cyano, halo, haloalkyl, —$R^6$—$OR^4$, —$R^6$—$N(R^4)_2$, —$R^6$—$C(O)OR^4$, and —$R^6$—$N(R^4)C(O)R^4$;
$R^3$ is benzyl wherein the phenyl group is optionally substituted with one or more alkyl substituents;
each $R^4$ is independently selected from the group consisting of hydrogen, alkyl, aryl, and aralkyl; and
each $R^6$ is a direct bond.

Of this preferred subclass of compounds, preferred compounds are selected from the group consisting of the following:
N-[4-(2-benzyl-1-oxo-1,2-dihydroisoquinolin-3-yl)phenyl]acetamide;
3-(4-aminophenyl)-2-(2,4-dimethylbenzyl)-2H-isoquinolin-1-one;
3-(3,5-bis-trifluoromethylphenyl)-2-(2,4-dimethylbenzyl)-2H-isoquinolin-1-one;
4-[2-(2,4-dimethylbenzyl)-1-oxo-1,2-dihydroisoquinolin-3-yl]benzoic acid methyl ester;
2-(2,4-dimethylbenzyl)-3-(4-methoxy-3-trifluoromethylphenyl)-2H-isoquinolin-1-one;
N-{4-[2-(2,4-dimethylbenzyl)-1-oxo-1,2-dihydroisoquinolin-3-yl]phenyl}-acetamide;
4-[2-(2,4-dimethylbenzyl)-1-oxo-1,2-dihydroisoquinolin-3-yl]benzonitrile;
2-(2,4-dimethylbenzyl)-3-(3-trifluoromethylphenyl)-2H-isoquinolin-1-one;
2-(4-methylbenzyl)-3-(3-trifluoromethylphenyl)-2H-isoquinolin-1-one;
2-benzyl-3-(3-trifluoromethylphenyl)-2H-isoquinolin-1-one;
3-(4-bromophenyl)-2-(2,4-dimethylbenzyl)-2H-isoquinolin-1-one; and
3-(4-bromophenyl)-2-(4-methylbenzyl)-2H-isoquinolin-1-one.

Of the compounds of the invention as set forth above in the Summary of the Invention, another preferred group of compounds are those compounds wherein:
n is 0 to 4;
each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$S(O)_tR^4$ (where t is 0 to 2), and —$R^6$—$S(O)_pN(R^4)_2$ (where p is 1 or 2);

$R^2$ is aryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R)^4)C(O)OR^5$, —$R_6$—$N[S(O)_tR^4]_2$ (where t is 0 to 2), —$R^6$—$N(R^4)(S(O)_tR^4)$ (where t is 0 to 2), —$R^6$—$S(O)_tR^4$) (where t is 0 to 2), and —$R_6$—$S(O)_pN(R^4)_2$ (where p is 1 or 2);

$R^3$ is alkyl or cycloalkylalkyl optionally substituted with one or more substituents selected from the group consisting of alkyl, alkenyl, cyano, nitro, halo, haloalkyl, haloalkenyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

or $R^3$ is heteroarylalkyl wherein the heteroaryl group of the heteroarylakyl substituent is optionally substituted with one or more substituents selected from the group consisting of alkyl, alkenyl, aryl, aralkyl, cya no, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N[S(O)_tR^4]_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen or aralkyl.

Of this preferred group of compounds, a preferred subgroup of compounds are those compounds wherein:

n is 0 to 4;

each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;

$R^2$ is phenyl optionally substituted with one or more substituents selected from the group consisting of alkyl, cyano, nitro, halo, haloalkyl, optionally substituted aryl, optionally substituted aralkyl, optionally substituted heteroaryl, optionally substituted heteroarylalkyl, —$R^6$—$OR^4$, —$R^6$—$N(R^4)_2$, —$R^6$—$C(O)OR^4$, and —$R^6$—$C(O)N(R^4)_2$;

$R^3$ is alkyl or cycloalkylalkyl optionally substituted with one or more substituents selected from the group consisting of alkyl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, optionally substituted aryl, optionally substituted aralkyl, optionally substituted heterocyclyl and optionally substituted heteroaryl;

each $R^6$ is a direct bond or a straight or branched alkylene chain; and $R^7$ is hydrogen or aralkyl.

Of this preferred subgroup of compounds, preferred compounds are selected from the group consisting of the following:

8-chloro-2-cyclohexylmethyl-3-(4-phenoxyphenyl)-2H-isoquinolin-1-one; and 8-chloro-2-(2,2-dimethyl-propyl)-3-(4-phenoxyphenyl)-2H-isoquinolin-1-one.

Of the preferred group of compounds described above, another preferred subgroup of compounds are those compounds wherein:

n is 0 to 4;

each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;

$R^2$ is phenyl optionally substituted with one or more substituents selected from the group consisting of alkyl, cyano, nitro, halo, haloalkyl, optionally substituted aryl, optionally substituted aralkyl, optionally substituted heteroaryl, optionally substituted heteroarylalkyl, —$R^6$—$OR^4$, —$R^6$—$N(R^4)_2$, —$R^6$—$C(O)OR^4$, and —$R^6$—$C(O)N(R^4)_2$;

or $R^3$ is heteroarylalkyl optionally substituted with one or more substituents selected from the group consisting of alkyl, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, optionally substituted aryl, optionally substituted aralkyl, optionally substituted heterocyclyl and optionally substituted heteroaryl;

each $R^6$ is a direct bond or a straight or branched alkylene chain; and $R^7$ is hydrogen or aralkyl.

Of this preferred subgroup of compounds, preferred compounds are those compounds selected from the group consisting of the following:

8-chloro-3-(4-phenoxyphenyl)-2-pyridin-3-ylmethyl-2H-isoquinolin-1-one-trifluoroacetic acid salt;

8-chloro-2-(5-methyl-furan-2-ylmethyl)-3-(4-phenoxyphenyl)-2H-isoquinolin-1-one; and 8-chloro-3-(4-phenoxyphenyl)-2-thiophen-2-ylmethyl-2H-isoquinolin-1-one.

F. Preparation of the Compounds of the Invention

It is understood that in the following description, combinations of substituents and/or variables of the depicted formulae are permissible only if such contributions result in stable compounds.

It will also be appreciated by those skilled in the art that in the processes described below the functional groups of intermediate compounds may need to be protected by suitable protecting groups. Such functional groups include hydroxy, amino, mercapto and carboxylic acid. Suitable protecting groups for hydroxy include trialkylsilyl or diaryalkylsilyl (e.g., t-butyldimethylsilyl, t-butyldiphenylsilyl or trimethylsilyl), tetrahydropyranyl, benzyl, and the like. Suitable protecting groups for 1,2-dihydroxys include ketal- and acetal-forming groups. Suitable protecting groups for amino, amidino and guanidino include t-butoxycarbonyl, benzyloxycarbonyl, and the like. Suitable protecting groups for mercapto include —C(O)—R (where R is alkyl, aryl or aralkyl), p-methoxybenzyl, trityl and the like. Suitable protecting groups for carboxylic acid include alkyl, aryl or aralkyl esters.

Protecting groups may be added or removed in accordance with standard techniques, which are well-known to those skilled in the art and as described herein.

The use of protecting groups is described in detail in Green, T. W. and P. G. M. Wutz, Protective Groups in Organic Synthesis (1991), 2nd Ed., Wiley-Interscience. The protecting group may also be a polymer resin such as a Wang resin or a 2-chlorotrityl chloride resin.

It will also be appreciated by those skilled in the art, although such protected derivatives of compounds of formula (I), as described above in the Summary of the Invention, may not possess pharmacological activity as such, they may be administered to a mammal having a disease associated with defects in cholesterol transport, glucose metabolism, fatty acid metabolism and cholesterol metabolism, and thereafter metabolized in the body to form compounds of the invention which are pharmacologically active. Such derivatives may therefore be described as "prodrugs". All prodrugs of compounds of formula (I) are included within the scope of the invention.

It is understood that one of ordinary skill in the art would be able to make the compounds of the invention not specifically prepared herein in light of the following disclosure, including the Preparations and Examples, and information known to those of ordinary skill in the chemical synthesis field.

1. Preparation of Compounds of Formula (Ia)

Compounds of formula (Ia) are compounds of formula (I) as set forth above in the Summary of the Invention and are prepared as described below in Reaction Scheme 1 wherein X is halo; n is 1 to 4; m is 1 to 5; each $R^{3a}$ is independently selected from the group consisting of alkyl, aryl, aralkyl, cyano, nitro, halo, haloalkyl, cycloalkyl, heterocyclyl, —R—OR$^4$, —R$^6$—N(OR$^4$)$_2$, —R$^6$—C(O)OR$^4$, —R$^6$—C(O)N(R$^4$)$_2$, —R$^6$—N(R$^4$)C(O)R$^4$, —R$^6$—N(R$^4$)C(O)OR$^5$, —R$^6$—S(O)$_t$R$^4$ (where t is 0 to 2), and —R$^6$—S(O)$_p$N(R$^4$)$_2$ (where p is 1 or 2); each R$^1$, R$^2$, R$^4$, R$^5$ and R$^6$ is as described above in the Summary of the Invention; R$^8$ is alkyl or aralkyl; and R$^9$ is hydrogen, alkyl or —OR$^{10}$ where R$^{10}$ is hydrogen, alkyl, aryl or aralkyl:

REACTION SCHEME 1

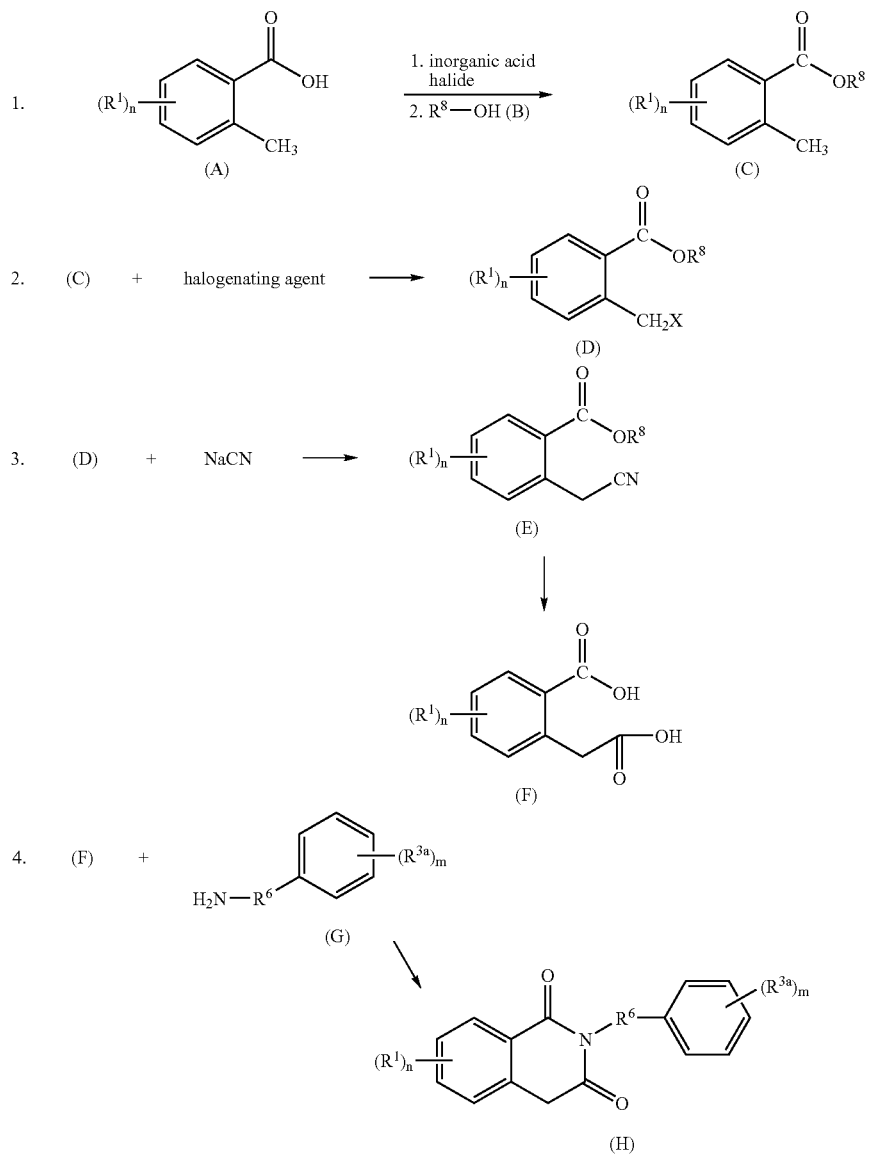

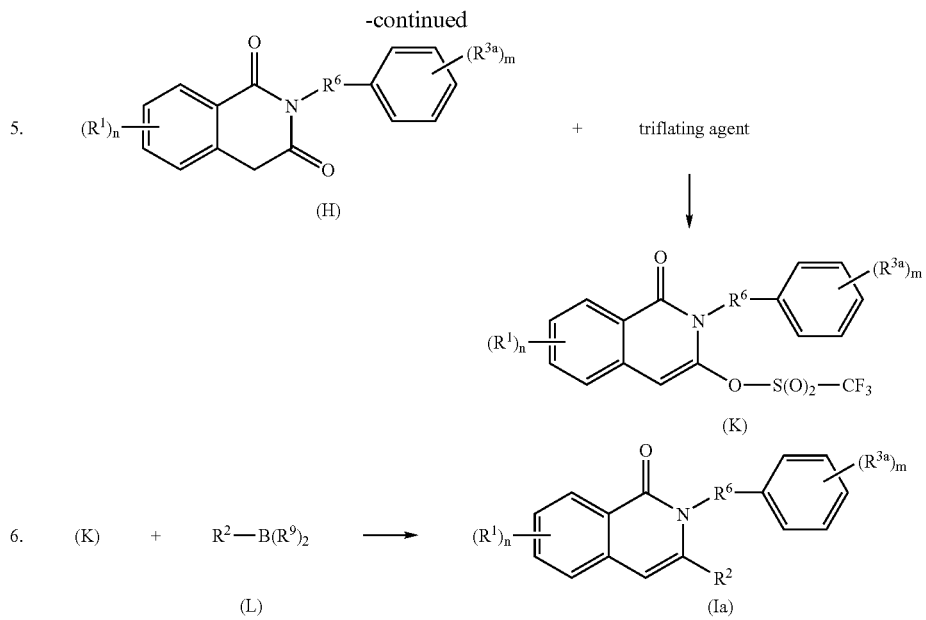

Compounds of formulae (A), (B), (G), and (L) are commercially available, or may be prepared by methods known to one skilled in the art or by methods disclosed herein. In particular, compounds of formula (A) can be prepared by methods similar to those described in *J. Org. Chem.* (1984), p. 1078; U.S. Pat. Nos. 5,607,898 and 5,945,380; and *J. Med. Chem.* (1997), p. 2017. Halogenating agents, such as N-bromosuccinimide, are commercially available, as well as triflating agents, such as 2-(5-chloropyridyl) bis-trifluoromethane-sulfonimide.

In general, compounds of formula (Ia) are prepared by first treating a compound of formula (A) with an inorganic acid halide, such as thionyl chloride, under standard conditions to form the corresponding acid halide. The acid halide is then dissolved in an aprotic solvent, such as methylene chloride, and the resulting solution is cooled to a temperature of between about 0° C. and about 5° C. An excess molar amount of a compound of formula (B) is then added to the solution, and the resulting reaction mixture is allowed to warm to ambient temperature. An organic base, such as triethylamine, is added to the reaction mixture to promote the reaction to completion. The compound of formula (C) is isolated from the reaction mixture by standard isolation techniques, such as organic extraction, filtration, concentration and flash chromatography.

Alternatively, to a suspension of a compound of formula (A) in a protic solvent, such as methanol, is added an equimolar amount of trimethyl orthoformate. The reaction mixture is treated with acid, such as hydrogen chloride gas, and the resulting solution is heated to a temperature of between about 50° C. and about 60° C., preferably to about 60° C., and stirred at that temperature for a period of between about 4 hours and about 16 hours, preferably for about 16 hours. The compound of formula (C) is then isolated from the reaction mixture by standard isolation techniques, such as concentration under reduced pressure.

A compound of formula (C), in a nonpolar solvent, such as carbon tetrachloride, in then treated with an slightly excess molar amount of a halogenating agent, preferably N-bromosuccinimide, in the presence of a catalyst, such as benzoyl peroxide. The resulting reaction mixture is then heated to a temperature of between about 80° C. and about 90° C., preferably to a temperature of about 85° C., and illuminated while stirring for a period of time of between about 8 hours and about 16 hours, preferably for about 16 hours. The reaction mixture is then allowed to warm to ambient temperature and the compound of formula (D) is then isolated from the reaction mixture by standard isolation techniques.

A compound of formula (D) in an aprotic solvent, such as dimethylformamide, is then treated with an excess molar amount of sodium cyanide. The resulting reaction mixture is then heated to a temperature of between about 50° C. and about 60° C., preferably to a temperature of about 55° C. and stirred for a period of time of between about 1 hour and about 2 hours, preferably for about 1.5 hours. The reaction mixture is then allowed to warm to ambient temperature and stirred at that temperature for a period of time of between about 8 hours and about 16 hours, preferably for about 16 hours. The compound of formula (E) is then isolated from the reaction mixture by standard isolation techniques, such as organic extraction, filtration, concentration and flash chromatography.

A compound of formula (E) is then treated under base hydrolysis conditions, such as treating the compound with an aqueous sodium hydroxide solution at ambient temperature while stirring for a period of time of between about 8 hours and about 16 hours, preferably for about 16 hours. The reaction mixture is then heated to reflux temperature for a period of time of between about 2 hours and about 3 hours, preferably for about 2.5 hours. The reaction mixture is then cooled to a temperature of between about 0° C. and about 5° C. and slowly acidified by the addition of a strong acid, such as hydrochloric acid. The compound of formula (F) is then isolated from the reaction mixture by standard isolation techniques, such as organic extraction, filtration and concentration.

A compound of formula (F) is then treated with a slightly excess molar amount of a compound of formula (G) and the resulting reaction mixture is heated to a temperature of between about 170° C. and about 180° C., preferably at about 180° C., for a period of time of between about 60 hours and about 70 hours, preferably for about 64 hours. The reaction mixture is then allowed to come to ambient temperature. The compound of formula (H) is then isolated from the reaction mixture by standard isolation techniques, such as organic extraction, concentration and silica gel column chromatography.

To a solution of an alkaline metal amide base, such as lithium hexamethyldisilazide, in an aprotic solvent, such as tetrahydrofuran, at a temperature of between about −80° C. and about −30° C., preferably at about −78° C., is added an excess molar amount of a compound of formula (H) in an aprotic solvent, such as tetrahydrofuran. The resulting reaction mixture is stirred for a period of time of between about 30 minutes and about 1 hour, preferably for about 30 minutes, at a temperature of between about −80° C. and about −30° C., preferably at about −78° C., to form the corresponding enolate ion of the compound of formula (H). A triflating agent, such as 2-(5-chloropyridyl) bis-trifluoromethanesulfonimide, is then added to the solution over a period of time, preferably over 20 minutes, at a temperature of between about −80° C. and about −30° C., preferably at about −78° C. The resulting reaction mixture is stirred for a period of time of between about 1 hour and about 2 hours, preferably for about 75 minutes. The reaction is quenched by the addition of an aqueous solution, and the reaction mixture is allowed to warm to ambient temperature. The compound of formula (K) is then isolated from the reaction mixture by standard isolation techniques, such as filtration and purification by silica gel column chromatography.

A mixture of a compound of formula (K) and a compound of formula (L) in an aprotic solvent, such as tetrahydrofuran, in the presence of a stablizing ligand, such as triphenylarsine, is then treated with a coupling reaction catalyst, such as bis(acetonitrile) palladium (II) chloride in the presence of base, such as aqueous sodium carbonate. The resulting reaction mixture is stirred at ambient temperature for a period of time between about 1 hour and about 2 hours, preferably for about 90 minutes. The compound of formula (Ia) is then isolated from the reaction mixture by standard isolation techniques, such as organic extraction, filtration, concentration and purification by silica gel column chromatography.

2. Preparation of Compounds of Formula (Ib)

Compounds of formula (Ib) are compounds of formula (I) as set forth above in the Summary of the Invention and are prepared as described below in Reaction Scheme 2 wherein n is 1 to 4; $R^1$, $R^2$, $R^3$ and $R^7$ are as described above in the Summary of the Invention; X is halo and each $R^8$ is independently alkyl or aralkyl:

REACTION SCHEME 2

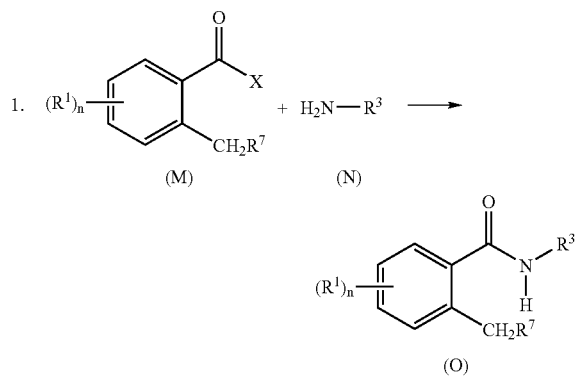

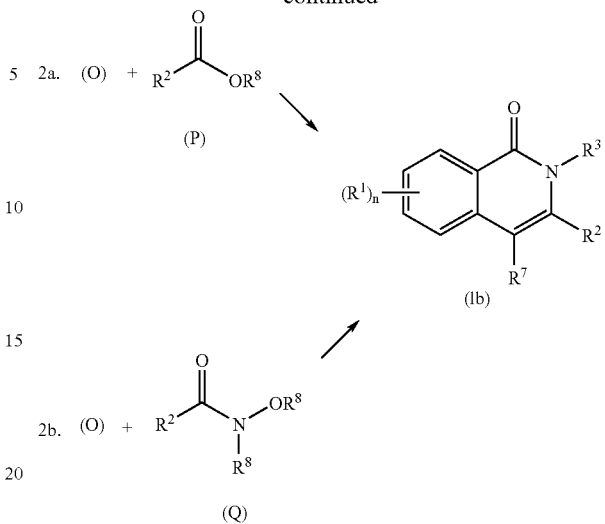

Compounds of formulae (M), (N), (P), and (Q) are commercially available, or may be prepared by methods known to one skilled in the art or by methods disclosed herein.

In general, compounds of formula (Ib) are prepared by first dissolving a compound of formula (N) in an aprotic solvent, such as methylene chloride and cooling the resulting solution to a temperature of between about 0° C. and about 5° C., preferably at about 0° C. To this cooled solution, a slightly excess molar amount of a compound of formula (M) is added. The resulting reaction mixture is then allowed to warm to ambient temperature and stirred for a period of between about 12 hours and about 16 hours, preferably for about 14 hours. The compound of formula (O) is then isolated from the reaction mixture by standard isolation techniques, such as organic extraction, filtration, concentration and recrystallization.

An excess molar lithium diisopropylamide solution is then prepared using standard techniques (e.g., treatment of diisopropylamine in a polar solvent, such as tetrahydrofuran with n-butyllithium). To this solution is added a compound of formula (0) in a polar solvent, such as tetrahydrofuran. The resulting reaction mixture is then stirred at a temperature of between about 0° C. and about 5° C. for a period of time of between about 30 minutes and about 60 minutes, preferably for about 55 minutes, to form a dilithiated intermediate. A compound of formula (P) in an aprotic polar solvent, such as tetrahydrofuran, is then added to the reaction mixture. The resulting reaction mixture is stirred at a temperature of between about 0° C. and about 5° C., preferably at about 0° C., for a period of time of between about 30 minutes and about 1 hours, preferably for about 1 hour. The condensation reaction is quenched by the addition of a strong acid, such as hydrochloric acid. The resulting mixture is then heated to reflux temperature with vigorous stirring for a period of time of between about 60 minutes and about 80 minutes, preferably for about 75 minutes to promote the desired cyclization. The reaction mixture is allowed to cool to ambient temperature. The reaction mixture is then neutralized and the compound of formula (Ib) is isolated from the reaction mixture by standard isolation techniques, such as evaporation of solvents, organic extraction, filtration, concentration and column chromatagraphy.

Alternatively, to the excess molar lithium diisopropylamide solution a compound of formula (O) in an aprotic solivent, such as tetrahydrofuran, is added. The resulting reaction mixture is then stirred at a temperature of between about 0° C. and about 5° C. for a period of time of between about 30 minutes and about 2 hours, preferably for about 75 minutes, to form a dilithiated intermediate. A slight excess molar amount of a compound of formula (Q) in an aprotic solvent, such as tetrahydrofuran, is then added to the reaction mixture. The resulting reaction mixture is allowed to warm to ambient temperature over a period of time of between about 1 hour and about 2 hours, preferably for about 100 minutes. The reaction mixture is quenched by the addition of acid, preferably hydrochloric acid. The resulting reaction mixture is then heated to reflux with vigorous stirring for a period of time of between about 30 minutes and about 2 hours, preferably for about an hour. The reaction mixture is allowed to warm to ambient temperature and basified. The compound of formula (Ib) is then isolated from the reaction mixture by standard isolation techniques, such as organic extraction, filtration, concentration and purification by silica gel column chromatography.

3. Preparation of Compounds of Formula (Ic)

Compounds of formula (Ic) are compounds of formula (I) as set forth above in the Summary of the Invention and are prepared as described below in Reaction Scheme 3 wherein n is 1 to 4; m is 1 to 5; $R^{2}a$ is alkynyl optionally substituted with $-Si(R^4)_3$, hydroxyalkyl, aryl, cycloalkyl; each $R^3a$ is independently selected from the group consisting of alkyl, aryl, aralkyl, cyano, nitro, halo, haloalkyl, cycloalkyl, heterocyclyl, $-R^6-OR^4$, $-R^6-N(R^4)_2$, $-R^6-C(O)OR^4$, $-R^6-C(O)N(R^4)_2$, $-R^6-N(R^4)C(O)R^4$, $-R^6-N(R^4)C(O)OR^5$, $-R^6-S(O)_tR^4$ (where t is 0 to 2), and $-R^6-S(O)_pN(R^4)_2$ (where p is 1 or 2); and $R^1$ and $R^6$ are as described above in the Summary of the Invention:

REACTION SCHEME 3

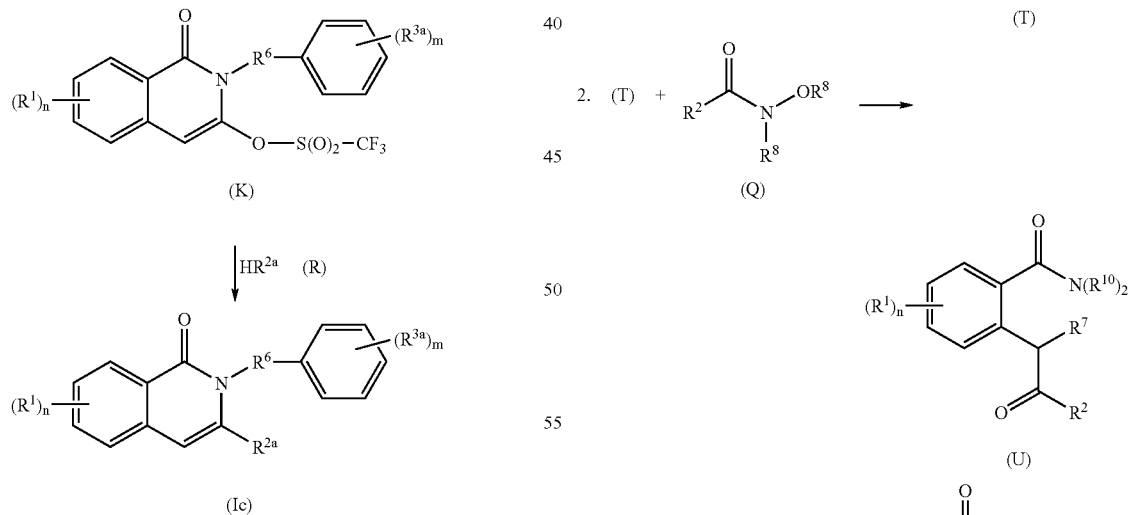

Compounds of formula (K) are prepared as described above in Reaction Scheme 1. Compounds of formula (R) are commercially available or can be prepared by methods known to one of ordinary skill in the art.

In general, compounds of formula (Ic) are prepared by first treating a solution of a compound of formula (K) in an aprotic solvent, such as tetrahydrofuran, with a base, such as triethylamine. The resulting mixture is then degassed for a period of time of between about 10 minutes and 30 minutes, preferably for about 20 minutes. The resulting degassed solution is then treated with an excess molar amount of a compound of formula (R), in the presence of one or more catalysts (such as tetrakistriphenylphosphine Pd (0) and copper iodide) The resulting reaction mixture was stirred at ambient temperature for a period of between about 12 hours and 20 hours, preferably for about 16 hours. The compound of formula (Ic) is then isolated from the reaction mixture by standard isolation techniques, such as filtration, concentration and purificiation by silica gel column chromatography.

4. Preparation of Compounds of Formula (Id)

Compounds of formula (Id) are compounds of formula (I) as set forth above in the Summary of the Invention and are prepared as described below in Reaction Scheme 4 wherein n is 1 to 4; $R^1$, $R^2$, $R^3$ and $R^7$ are as described above in the Summary of the Invention; each $R^8$ is independently alkyl or aralkyl and $R^{10}$ is hydrogen, alkyl, aryl or aralkyl:

REACTION SCHEME 4

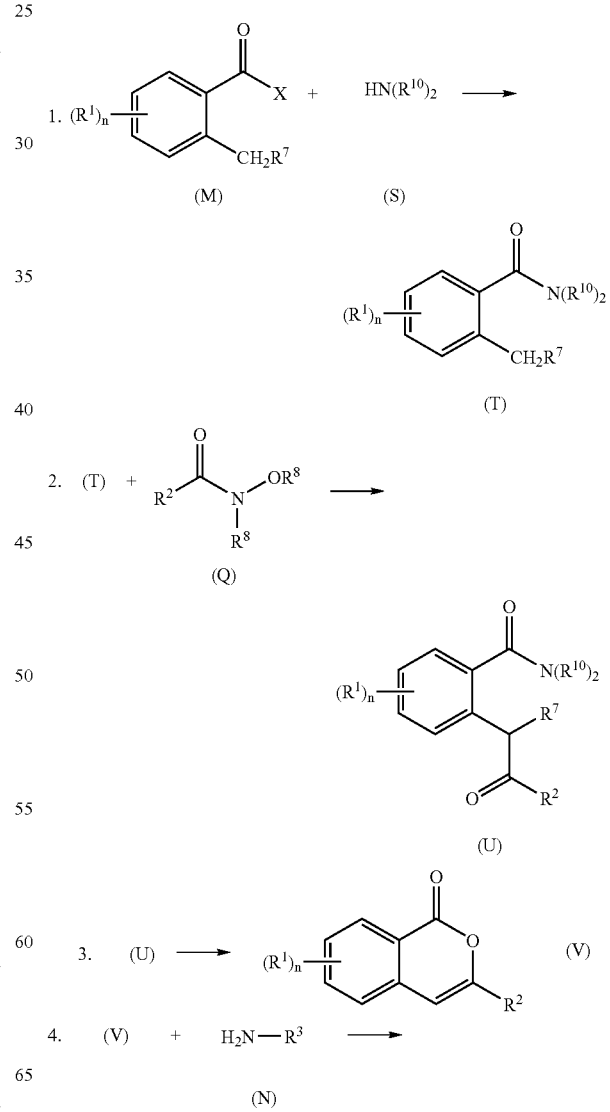

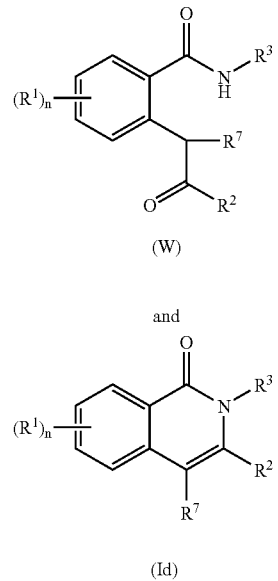

(W)

and (Id)

Compounds of formulae (M), (N), (S), (Q) are commercially available, or may be prepared by methods known to one skilled in the art or by methods disclosed herein.

In general, compounds of formula (Id) are prepared by first dissolving a compound of formula (S) in an aprotic solvent, such as methylene chloride and cooling the resulting solution to a temperature of between about 0° C. and about 5° C., preferably at about 0° C. To this cooled solution, a slightly excess molar amount of a compound of formula (M) is added. The resulting reaction mixture is then allowed to warm to ambient temperature and stirred for a period of between about 12 hours and about 16 hours, preferably for about 14 hours. The compound of formula (T) is then isolated from the reaction mixture by standard isolation techniques, such as organic extraction, filtration, concentration and purification by silica gel column chromatography or recrystallization.

An excess molar lithium diisopropylamide solution is then prepared using standard techniques (e.g., treatment of diisopropylamine in a polar solvent, such as tetrahydrofuran with n-butyllithium). To this solution is added a compound of formula (T) in a polar solvent, such as tetrahydrofuran. The resulting reaction mixture is then stirred at a temperature of between about −80° C. and about −60° C. for a period of time of between about 5 minutes and about 15 minutes, preferably for about 10 minutes, to form a lithiated intermediate. A compound of formula (Q) in an aprotic polar solvent, such as tetrahydrofuran, is then added to the reaction mixture. The resulting reaction mixture is stirred at a temperature of between about −80° C. and about −60° C., preferably at about −78° C., for a period of time of between about 10 minutes and about 1 hours, preferably for about 15 minutes. The condensation reaction is quenched by the addition of a weak acid, such as saturated aqueous ammonium chloride and the compound of formula (U) is isolated from the reaction mixture by standard isolation techniques, such as evaporation of solvents, organic extraction, filtration, concentration and column chromotagraphy.

Alternatively, to the excess molar lithium diisopropylamide solution a mixture of the compounds of formula (T) and (Q) in an aprotic solivent, such as tetrahydrofuran, is added. The resulting reaction mixture is then stirred at a temperature of between about −80° C. and about −60° C. for a period of time of between about 10 minutes and about 1 hours, preferably for about 15 minutes. The condensation reaction is quenched by the addition of a weak acid, such as saturated aqueous ammonium chloride and the compound of formula (U) is isolated from the reaction mixture by standard isolation techniques, such as evaporation of solvents, organic extraction, filtration, concentration and column chromatography.

In a manner similar to that described in *Chem. Pharm. Bull.* (1993), p. 1188, the compound of formula (U) is then taken up in an appropriate solvent such as acetic acid or propionic acid, preferably propionic acid, and heated to a temperature of between 130° C. and 150° C. for between 16 hours and 96 hours. The reaction mixture is then cooled to ambient temperature and the product of formula (V) can be isolated from the reaction mixture by standard isolation techniques, such as evaporation of solvents, organic extraction, filtration, concentration and column chromatography or recrystallization from an appropriate solvent.

To a mixture of a compound of formula (N) and a compound of formula (V) in an appropriate solvent, such as toluene, is added a solution of methyl aluminoxane in toluene. The resulting reaction mixture is then heated to between 100° C. and 120° C., preferably 115° C., for between 12 and 24 hours, preferably 16 hours. The reaction mixture is then allowed to cool to ambient temperature, and is quenched by the addition of acid, preferably hydrochloric acid. Compounds of formulae (W), and (1d) can then be isolated from the reaction mixture by standard isolation techniques, such as evaporation of solvents, organic extraction, filtration, concentration and column chromatography.

Alternatively, a compound of formula (W), which can be prepared from compounds of formula (V) and (N) in a manner similar to that described above or in a manner similar to that described in *SynLett* (1997) p. 277, is dissolved in an appropriate solvent, such as 1,4-dioxane or toluene, preferably 1,4-dioxane. Less than one molar equivalent of p-toluenesulfonic acid monohydrate is added to the solution. The reaction mixture is then heated to reflux for between 12 hours and 24 hours, preferably 16 hours. The resulting reaction mixture is then allowed to cool to ambient temperature, and is then quenched by the addition of a molar excess of an organic base such as triethylamine. The compound of formula (1d) is then isolated from the reaction mixture by standard isolation techniques, such as organic extraction, filtration, concentration and purification by silica gel column chromatography or recrystallization.

5. Preparation of Compounds of Formula (Ie)

Compounds of formula (Ie) are compounds of formula (I) as set forth above in the Summary of the Invention and are prepared as described below in Reaction Scheme 5 wherein n is 1 to 4; $R^{2b}$ is aryl or heteroaryl substituted by at least one halo substituent; $R^1$, $R^3$ and $R^7$ are each as described above in the Summary of the Invention, each $R^9$ is hydrogen, alkyl or —$OR^{10}$ where $R^{10}$ is hydrogen, alkyl, aryl or aralkyl; and $R^{11}$ is aryl or heteroaryl, each being optionally substituted by one or more substituents selected from the group consisting of alkyl, cyano, nitro, halo, haloalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(R^4)(S(O)_tR^4)$ (where t is 0 to 2), —$R^6$—$N[(S(O)_tR^4)]_2$ (where t is 0 to 2), —$R^6$—$S(O)_tR^4$ (where t is 0 to 2), and —$R^6$—$S(O)_pN(R^4)_2$ (where p is 1 or 2):

REACTION SCHEME 5

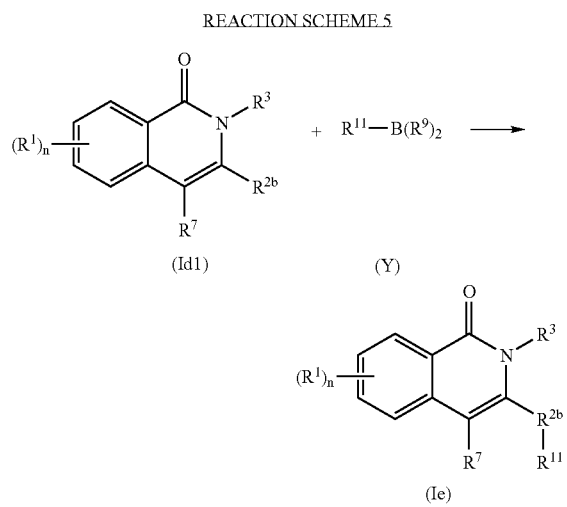

Compounds of formula (Id1) are compounds of formula (Id) and are as prepared as described herein and above in Reaction Scheme 4. Compounds of formula (Y) are commercially available, or may be prepared by methods known to one skilled in the art or by methods disclosed herein.

In general, compounds of formula (Ie) are prepared by first treating a solution of a compound of formula (Id1) in an aprotic solvent, such as tetrahydrofuran, with a base, such as aqueous potassium carbonate. The resulting mixture is then degassed for a period of time of between about 10 minutes and 30 minutes, preferably for about 20 minutes. The resulting degassed solution is then treated with an excess molar amount of a compound of formula (Y), in the presence of one or more catalysts (such as dichloro[1,1'-bis(diphenylphosphino)ferrocene]palladium (II) dichloromethane adduct). The resulting reaction mixture is stirred at 60° C. for a period of between about 12 hours and 20 hours, preferably for about 16 hours. The compound of formula (Ie) is then isolated from the reaction mixture by standard isolation techniques, such as filtration, concentration and purificiation by silica gel column chromatography.

Alternatively, compounds of formula (Id1) wherein $R^{2b}$ is an aryl or heteroaryl group substituted by at least one hydroxy group can be treated with the appropriate triflating agent under standard conditions to produce intermediate compounds of formula (Id1) wherein $R^{2b}$ is an aryl or heteroaryl group substituted by at least one —O—S(O)$_2$—CF$_3$ group, which can then be treated with the appropriate compound of formula (Y) under similar conditions as described above to produce compounds of formula (Ie).

All compounds of the invention as prepared above which exist in free base or acid form may be converted to their pharmaceutically acceptable salts by treatment with the appropriate inorganic or organic base or acid. Salts of the compounds prepared above may be converted to their free base or acid form by standard techniques. It is understood that all pharmaceutically acceptable derivatives of the compound of the invention, such as polymorphs, amorphous forms, anhydrates, hydrates, solvates and salts, are intended to be within the scope of the invention.

The following specific Preparations (for intermediates) and Examples (for compounds, pharmaceutical compositions and methods of use of the invention) are provided as a guide to assist in the practice of the invention, and are not intended as a limitation on the scope of the invention.

Preparation 1

Compounds of Formula (C)

A. A suspension of 2-chloro-6-methyl-benzoic acid (7.82 g, 45.8 mmol) in thionyl chloride (20.0 mL, 275 mmol), was immersed in an oil bath held at 85° C., and refluxed for 16 hours. The resulting pale brown solution was concentrated under reduced pressure to afford the acid chloride as a pale brown oil. This material was carried on to the ester formation without purification. The acid chloride (45.8 mmol from previous step) was dissolved in dichloromethane (20 mL) and the mixture cooled in an ice bath. Methanol (10 mL, 247 mmol) was added and the ice bath was then removed. HPLC of the reaction mixture 45 minutes after removal of the ice bath showed a 4:1 mixture of starting acid:product ester. The reaction mixture was then treated with triethylamine (15 mL, 108 mmol) dropwise over several minutes. The triethylamine addition was exothermic and led to the production of a lot of smoke in the reaction flask. After stirring overnight at ambient temperature HPLC indicated complete conversion to product. The reaction mixture was poured into a mixture of ether (200 mL) and saturated aqueous sodium hydrogen carbonate solution (100 mL). The layers were separated and the basic aqueous layer was extracted with ether (3×50 mL). The organic layers were combined and washed with brine, then dried (Na$_2$SO$_4$), filtered, and concentrated under reduced pressure to afford a yellow oil. The material was purified by flash chromatography eluting with a gradient from 0% to 10% ethyl acetate/hexane to afford 2-chloro-6-methylbenzoic acid methyl ester (7.38 g, 87% yield) as a clear colorless liquid: $^1$H-NMR (400 MHz, CDCl$_3$): δ7.24-7.19 (2H, m), 7.14-7.08 (1H, m), 3.95 (3H, s), 2.32 (3H, s) ppm.

B. Alternatively, to a suspension of 3-chloro-2-methylbenzoic acid (6.8 g, 40 mmol) in methanol (40 mL) was added trimethyl orthoformate (4.4 mL, 40 mmol). HCl gas was then bubbled through the suspension for 20 minutes. The resulting solution was then heated in a 60° C. oil bath. After stirring at 60° C. for 16 hours, the solution was allowed to cool to ambient temperature and concentrated under reduced pressure to afford a thick yellow paste. The semi-solid was melted under reduced pressure using a heat gun, and then cooled to afford 3-chloro-2-methylbenzoic acid methyl ester (7.1 g, 95% yield) as a yellow crystalline solid: $^1$H-NMR (400 MHz, CDCl$_3$): δ 7.70 (1H, d, J=7.8 Hz), 7.51 (1H, d, J=7.8 Hz), 7.17 (1H, t, J=7.8 Hz), 3.91 (s, 3H), 2.60 (s, 3H) ppm.

C. In a similar manner, other compounds of formula (C) were prepared.

Preparation 2

Compounds of Formula (D)

A. To a suspension of 3-chloro-2-methylbenzoic acid methyl ester (5.62 g, 30.4 mmol), and N-bromosuccinimide (5.94 g, 33.4 mmol) in carbon tetrachloride (200 mL) was added benzoyl peroxide (800 mg, 3.30 mmol). The resulting suspension was immersed in an oil bath held at 85° C., and illuminated with a 300W halogen worklight. After stirring for 16 hours with heat and illumination the reaction mixture was allowed to cool to ambient temperature, filtered to remove the insoluble succinimide, and concentrated under reduced pressure to afford 2-bromomethyl-3-chlorobenzoic acid methyl ester as a yellow semi-solid. This crude material was carried on to the next step without purification.

B. In a similar manner, other compounds of formula (D) were prepared.

Preparation 3

Compounds of Formula (E)

A. To a solution of crude 2-bromomethyl-3-chlorobenzoic acid methyl ester (30.4 mmol) in DMF (60 mL), was added finely powdered sodium cyanide (2.22 g, 45 mmol). The reaction mixture turned brown rapidly, and became warm. The dark suspension was then immersed in an oil bath held at 55° C. The reaction mixture was allowed to stir at 55° C. for 1.5 hours, at which time heating was discontinued, and the reaction was allowed to cool to ambient temperature. After stirring at ambient temperature for 16 hours, the reaction was diluted with ether (300 mL) and water (200 mL). The layers were separated, the aqueous was extracted with ether (3×75 mL), and the combined organic extracts were washed with water (3×50 mL). The organic layer was then washed with brine (100 mL), dried over $Na_2SO_4$, filtered, and concentrated under reduced pressure to afford a yellow oil. The crude oil was purified by flash chromatography eluting with a gradient from 0% to 16% ethyl acetate/hexane to afford 3-chloro-2-cyanomethylbenzoic acid methyl ester (3.9 g, 65% yield over two steps) as a white solid: $^1$H-NMR (400 MHz, $CDCl_3$): δ 7.96 (1H, dd, J=8.1 Hz, 1.3 Hz), 7.65 (1H, dd, J=8.1, 1.3), 7.4 (1H, t, J=7.9Hz), 4.35 (2H, s), 3.97 (3H, s) ppm.

B. In a similar manner, other compounds of formula (E) were prepared.

Preparation 4

Compounds of Formula (F)

A. A suspension of 3-chloro-2-cyanomethyl-benzoic acid methyl ester (4.12 g, 21.1 mmol) in 10% (w/v) aqueous sodium hydroxide solution (30 mL) was allowed to stir for 16 hour at ambient temperature. The reaction suspension was then heated to reflux. After 2.5 hours at reflux the reaction suspension had become a pale yellow solution. The reaction solution was cooled in an ice bath and carefully acidified by dropwise addition of concentrated HCl. The resulting slurry was saturated by addition of solid NaCl, and extracted with ethyl acetate (3×100 mL). The organic extracts were dried $Na_2SO_4$, filtered and concentrated under reduced pressure to afford 2-carboxymethyl-3-chlorobenzoic acid (4.22 g, 93% yield) as a white solid: $^1$H-NMR (400 MHz, $CDCl_3$): δ 8.06 (1H, dd, J=7.8, 1.3 Hz), 7.66 (1H, dd, J=7.8, 1.3 Hz), 7.35 (1H, app t, J=7.8 Hz), 4.38 (2H, s) ppm.

B. In a similar manner, other compounds of formula (F) were prepared.

Preparation 5

Compounds of Formula (H)

A. A mixture of 2-carboxymethyl-3-chlorobenzoic acid (1.91 g, 8.9 mmol) and 2,4-dimethylbenzylamine (1.35 mL, 9.6 mmol) was placed in a vented vial and heated in an oil bath maintained at 180° C. After heating for 64 hours the reaction was allowed to cool to ambient temperature, then taken up in a mixture of $CH_2Cl_2$, acetone, and methanol. The solution was mixed with silica gel and then concentrated under reduced pressure to afford a free flowing solid. This solid was loaded onto the top of a silica gel column and eluted with a gradient from 0% to 14% ethyl acetate/hexane to afford 5-chloro-2-(2,4-dimethylbenzyl)-4H-isoquinoline-1,3-dione (2.03 g, 73% yield) as a yellow solid: $^1$H-NMR (400 MHz, $CDCl_3$): δ 8.17 (1H, dd, J=7.8, 1.3 Hz), 7.65 (1H, dd, J=7.8, 1.3 Hz), 7.42 (1H, app. t, J=7.8 Hz), 6.98 (1H, br s), 6.96-6.92 (1H, m), 6.91-6.87 (1H, m), 5.16 (2H, s), 4.09 (2H, s), 2.44 (3H, s), 2.26 (3H, s) ppm.

B. In a similar manner, other compounds of formula (H) were prepared.

Preparation 6

Compounds of Formula (K)

A. To a solution of lithium hexamethyldisilazide (2.0 mL of a 1M solution in THF) diluted with THF (4 mL) and immersed in a −78° C. cooling bath was added 8-chloro-2-(2,4-dimethylbenzyl)-4H-isoquinoline-1,3-dione (416 mg, 1.33 mmol) as a solution in THF (4 mL) dropwise over ten minutes. The dione containing vial and syringe were then rinsed with THF (2 mL), and the rinse was added to the hexamethyldisilazide solution to insure complete transfer. After stirring for 30 min at −78° C. a pale yellow suspension had formed. The 2-(5-chloropyridyl) bis-trifluoromethanesulfonimide (790 mg, 2.0 mmol), as a solution in THF (5.0 mL) was then added to the enolate suspension dropwise over 20 minutes at −78° C. After stirring for 75 minutes at −78° C., the reaction mixture was quenched by the addition of wet THF, allowed to warm to ambient temperature, and concentrated under reduced pressure to remove the THF. The resulting residue was dissolved in ethyl acetate and filtered through a short plug of silica (25 g of silica) which was then eluted thoroughly with ethyl acetate. The pale green filtrate was concentrated in vacuo and then purified by silica gel column chromatography eluting with a gradient from 0% to 10% ethyl acetate/hexane. The main product peak was collected to afford trifluoromethanesulfonic acid 8-chloro-2-(2,4-dimethylbenzyl)-1-oxo-1,2-dihydroisoquinolin-3-yl ester (332 mg, 56% yield) as a white crystalline solid: $^1$H-NMR (400 MHz, Acetone $d_6$): δ7.69 (1H, dd J=7.8, 1.3 Hz), 7.60 (1H, app. t, J=7.8 Hz), 7.51 (1H, dd, J=7.8, 1.3 Hz), 6.92 (1H, br s), 6.78 (1H, brd, J=7.6Hz), 6.73 (1H, s), 6.51 (1H, d, J=7.8Hz), 5.19 (2H, s), 2.26 (3H, s), 2.11 (3H, s) ppm.

B. In a similar manner, other compounds of formula (K) were prepared.

Preparation 7

Compounds of Formula (L)

A. To a solution of 4-bromo-2-chloro-phenylamine (4.2 g, 20 mmol), in dioxane (80 mL) was added triethylamine (10 mL, 72 mmol). The pale yellow solution was sparged with nitrogen. During the nitrogen sparge, 4,4,5,5-tetramethyl-[1,3,2]dioxaborolane (8.5 mL, 59 mmol) was added dropwise over 10 minutes. After 20 minutes the nitrogen sparge was discontinued and dichloro[1,1'-bis(diphenylphosphino)ferrocene)palladium (II) dichloromethane adduct (603 mg, 0.74 mmol) was added. The reaction was then heated to 100° C. in a temperature controlled heating mantle. After stirring for 20 hours at 100° C., HPLC analysis of the reaction showed clean conversion to a product. The reaction was allowed to cool to ambient temperature and diluted with Et$_2$O (250 mL) and H$_2$O (100 mL). The resulting brown biphasic suspension was filtered to remove some solids that had formed. The layers were separated, and the aqueous layer was extracted with Et$_2$O (3×50 mL). The combined organic layers were washed with brine (100 mL), dried over Na$_2$SO$_4$, then filtered and concentrated under reduced pressure to afford a brown oil, which partially solidified after standing at ambient temperature. This crude product was purified by silica gel column chromatography eluting with a gradient from 0% to 20% ethyl acetate/hexane on silica. The product peak was collected to afford 2-chloro-4-(4,4,5,5-tetramethyl-[1,3,2]dioxaborolan-2-yl)-phenylamine (2.6 g, 50% yield) as an off-white solid. $^1$H-NMR (400 MHz, CDCl$_3$): δ 7.69 (1H, d, J=1.3 Hz), 7.49 (1H, dd, J=8.1, 1.3 Hz), 6.72 (1H, d, J=8.1 Hz), 4.25 (2H, br s), 1.31 (12H, s).

B. In a similar manner, other compounds of formula (L) are prepared.

Preparation 8

Compounds of Formula (M)

A. A 250 mL round bottomed flask equipped with a magnetic stirring bar was charged with 2-chloro-6-methyl-benzoic acid (21.7 g, 127 mmol), and α,α-dichloromethyl methyl ether (29.0 mL, 327 mmol). The resulting brown suspension was immersed in an oil bath heated to 80° C. with stirring. Gas evolution was vigorous as the dark mixture was heated. After 1½ hours at 80° C. the gas evolution had subsided. After 3 hours at 80° C. heating was discontinued and the reaction was allowed to cool to ambient temperature. After stirring at ambient temperature for 64 hours, the reaction flask was placed in a heating mantle and fitted with a short-path distillation apparatus. The mantle temperature was brought up to ~140° C. and the excess α,α-dichloromethyl methyl ether was allowed to distill off. The dark fluid remaining in the distillation pot was concentrated on the rotary evaporator to remove any remaining traces of α,α-dichloromethyl methyl ether. The resulting crude 2-chloro-6-methyl-benzoyl chloride was used in the subsequent amide formation without further purification.

B. In a similar manner, other compounds of formula (M) are prepared.

Preparation 9

Compounds of Formula (O)

A. A solution of 4-methylbenzylamine (2.0 mL, 15.7 mmol), and triethylamine (4.4 mL, 31.6 mmol) in CH$_2$Cl$_2$ (50 mL) was cooled in an ice bath and treated dropwise with 2-methylbenzoyl chloride (2.5 mL, 19.2 mmol). After the end of the addition the ice bath was removed and the reaction mixture was allowed to warm to ambient temperature. After stirring at ambient temperature for 14 hours the resulting white suspension was diluted with CH$_2$Cl$_2$ (100 mL), and quenched by the addition of water (20 mL) and saturated aqueous sodium bicarbonate (20 mL). The aqueous layer was extracted with CH$_2$Cl$_2$ (3×30 mL), and the combined organics were dried over Na$_2$SO$_4$, filtered and concentrated to afford a white solid. The crude solid was recrystallized from ethyl acetate/hexane to afford 2-methyl-N-(4-methylbenzyl)benzamide (3.18 g, 85% yield) as a white crystalline solid; $^1$H-NMR (400 MHz, CDCl$_3$): δ 7.36 (1H, dd, J=7.6, 1.3 Hz), 7.32-7.14 (7H, m), 5.98 (1H, br s), 4.59 (2H, d, J=5.6 Hz), 2.47 (3H, s), 2.35 (3H, s) ppm.

B. In a similar manner, other compounds of formula (O) were prepared.

Preparation 10

Compounds of Formula (Q)

A. To a solution of 4-bromothiophene-2-carbaldehyde (9.1 g, 48 mmol) in acetone (150 mL) at 0° C. was added Jones' reagent (20 mL of a 2.6 M solution [prepared from CrO$_3$ (26.7 g, 270 mmol) dissolved in H$_2$O (40 mL), and H$_2$SO$_4$ (23 mL)], 52 mmol). After stirring for 30 minutes at 0° C., the ice bath was removed and the reaction was allowed to warm to ambient temperature. After 3 hours stirring at ambient temperature, the reaction was quenched by the addition of 2-propanol. After stirring for 64 hours at ambient temperature, the reaction mixture was diluted with Et$_2$O and filtered through a pad of Florisil. The pad was thoroughly washed with EtOAc, and the filtrate was concentrated under reduced pressure to afford a brown paste. This crude material was dissolved in hot aqueous ethanol, treated with decolorizing carbon and filtered while still hot. Upon cooling an oil separated and formed a suspension. This suspension was treated with solid NaOH (4 g, 100 mmol) and boiled briefly to dissolve the solids. The resulting basic aqueous solution was allowed to cool, and was extracted with Et$_2$O (75 mL). The Et$_2$O extract was discarded. The basic aqueous solution was then acidified by the dropwise addition of concentrated HCl. The acidic aqueous phase was extracted with EtOAc (4×60 mL). The combined EtOAc extracts were washed with brine, and dried over Na$_2$SO$_4$ for 16 hours. The mixture was filtered and concentrated under reduced pressure to afford 4-bromothiophene-2-carboxylic acid as a pale brown solid, which was carried on to the next step without further purification.

$^1$H-NMR (400 MHz, Acetone-d$_6$): δ 7.87 (1H, d, J=1.5 Hz), 7.72 (1H, d, J=1.5 Hz).

B. A suspension of 4-bromothiophene-2-carboxylic acid (47.0 mmol crude, from previous step) in α,α-dichloromethyl methyl ether (13.0 mL, 150 mmol) was slowly heated to reflux. As the reaction mixture was heated a pale brown solution formed, and gas evolution was evident. After stirring at a gentle reflux for 5 hours, the reaction solution was allowed to cool and was then concentrated under reduced pressure to afford 4-bromothiophene-2-carbonyl chloride as a brown liquid. This liquid was dissolved in CH$_2$Cl$_2$ (150 mL) and the reaction flask was cooled in an ice bath. The cold reaction solution was treated with a small amount of 4-(N,N-dimethylamino)pyridine, N,O-dimethylhydroxylamine hydrochloride (5.5 g, 56 mmol), and finally N,N-diisopropylethylamine (14 mL, 80 mmol). After stirring for 10 minutes, the ice bath was removed and the reaction mixture was allowed to warm to ambient temperature. After stirring for 16 hours, the pale brown reaction solution was quenched by the addition of ice-cold H$_2$O, and diluted with CH$_2$Cl$_2$ (500 mL). The layers were separated, and the organic layer was washed with 1 N HCl (100 mL), H$_2$O (50 mL), and saturated aqueous NaHCO$_3$ (50 mL). The organic layer was dried over Na$_2$SO$_4$, filtered and concentrated under reduced pressure to afford a brown liquid. The crude product was purified by silica gel column chromatography eluting with a gradient from 0% to 30% ethyl acetate/hexane on silica. The product peak was collected to afford 4-bromothiophene-2-carboxylic acid methoxymethylamide as a yellow oil. (9.9 g, 83% yield over three steps). $^1$H-NMR (400 MHz, CDCl$_3$): δ 7.83 (1H, d, J=1.5 Hz), 7.45 (1H, d, J=1.5 Hz), 3.78 (3H, s), 3.37 (3H, s).

C. A 500 mL three-necked round-bottom flask fitted with an overhead mechanical stirrer, and reflux condenser was charged with 4,5-dibromofuran-2-carboxylic acid (34.3 g, 127 mmol), $H_2O$ (100 mL), and HOAc (25 mL). The third neck of the flask was stoppered and the suspension was heated to reflux with a temperature controlled heating mantle held at 125-130° C. Zn dust (15.0 g, 229 mmol) (previously ground in a mortar and pestle to break up lumps) was added portionwise over 50 minutes. Subsequent portions are added after most of the previously added portion has disappeared. After the first portions of the Zn were added, all of the 4,5-dibromofuran-2-carboxylic acid dissolved to give a pale brown solution. Near the end of the Zn addition a white solid began to appear in the reaction flask. Ten minutes after the conclusion of the zinc addition a thick white slurry had formed. HPLC analysis of the reaction slurry after 15 minutes indicated nearly complete consumption of the starting 4,5-dibromofuran-2-carboxylic acid and conversion to the desired product. After 40 minutes, heating was discontinued, and the white slurry was allowed to cool to ambient temperature. After cooling to ambient temperature the reaction slurry was diluted with cold $H_2O$ (100 mL), cooled in an ice bath, and then filtered. The solids were rinsed with cold $H_2O$, dried on the filter, and the resulting damp solids were dissolved in warm acetone (1.6 L). The resulting solution was filtered to remove residual zinc dust, and then concentrated under reduced pressure to afford a white solid. The resulting solid was broken up with a spatula and pumped down under high vacuum to afford an off-white powder. $^1H$ NMR analysis of the material (DMSO-$d_6$) showed it to be quite pure but to contain $H_2O$. The solids were suspended in toluene (~1 L) and heated to reflux in a flask fitted with a condenser and a Dean-Stark trap. The suspension was heated at reflux for ~1 hour at which time less than 1 mL of $H_2O$ had collected in the trap. The suspension was cooled, and concentrated under reduced pressure to afford 4-bromo furan-2-carboxylic acid as a-white powdery solid. $^1$H-NMR (400 MHz, DMSO$d_6$): δ 7.96 (1H, d, J=0.8 Hz), 7.04 (1H, d, J=0.8 Hz).

D. The crude 4-bromofuran-2-carboxylic acid was placed in a 250 mL round bottom flask equipped with a magnetic stirring bar and a reflux condenser, and the flask was alternately evacuated and filled with nitrogen several times. To the stirred solid was carefully added α,α-dichloromethyl methyl ether (50 mL, 563 mmol). The addition was accompanied by vigorous gas evolution and was very exothermic, bringing the temperature of the resulting brown frothy mixture nearly to reflux. The gas evolution was allowed to subside, then the brown mixture was slowly heated to reflux using a heating mantle. The thick, partially solidified reaction mixture was then diluted with additional α,α-dichloromethyl methyl ether (20 mL, 225 mmol) to afford a dark brown solution containing some large black solid chunks. After heating at reflux for 135 minutes, the reaction was allowed to cool to ambient temperature, and then concentrated under reduced pressure. The resulting dark brown semi-solid was held under high vacuum to remove the last traces of solvents. While being held under vacuum at ambient temperature, some large colorless prisms appeared on the upper walls of the flask. The crude 4-bromofuran-2-carbonyl chloride was obtained as a dark brown semi-solid, and was used in the next step without purification.

E. A 1 L round bottom flask was charged with N,O-dimethylhydroxylamine hydrochloride (16.9 g, 173 mmol), 4-(N,N-dimethylamino)pyridine (~100 mg, catalytic) and $CH_2Cl_2$ (250 mL). This suspension was cooled in an ice bath. The 4-bromofuran-2-carbonyl chloride (127 mmol crude) was dissolved in $CH_2Cl_2$ (250 mL) containing N,N-diisopropylethylamine (70 mL, 400 mmol). The resulting dark mixture was cooled in an ice bath and then added via cannula to the cold N,O-dimethylhydroxylamine hydrochloride suspension. The acid chloride was not completely soluble, and was treated with further portions of $CH_2Cl_2$ (2×50 mL) in an attempt to solubilize the remaining material. These additional washes were added via cannula to the reaction mixture. There were still residual solids remaining in the acid chloride containing flask. A portion of the reaction solution was transferred via cannula to the acid chloride containing flask and was successful in solubilizing the remaining solids in the flask. This solution was transferred back to the reaction flask, and then the acid chloride flask was rinsed with additional $CH_2Cl_2$ (50 mL) which was added via cannula to the reaction flask to insure complete transfer. After the completion of the addition, the ice bath was removed and the dark reaction solution was allowed to warm to ambient temperature. After stirring at ambient temperature for 16 hours, TLC analysis showed the desired product to be present by comparison with authentic product. The dark reaction mixture was quenched by the addition of ice-cold $H_2O$ (300 mL) and dilution with additional $CH_2Cl_2$ (500 mL). A large quantity of off-white solids appeared after the biphasic mixture was transferred to a 2 L separatory funnel. Portions of 1 N HCl were added with occasional shaking in order to dissolve the solids. The layers were separated and the aqueous was extracted with $CH_2Cl_2$ (1×100 mL). The combined $CH_2Cl_2$ extracts were washed with 1 N HCl (100 mL), $H_2O$ (100 mL), then saturated aqueous $NaHCO_3$ (100 mL). The dark organic solution was dried over $Na_2SO_4$, filtered, and concentrated under reduced pressure to afford a dark brown solid. The solid was taken up in a minimum of $CH_2Cl_2$ and loaded onto a Biotage Flash 65 silica gel cartridge pre-conditioned with hexanes. Two-hundred milliliter fractions were collected as the column was eluted with 1 L portions of 10% followed by 15%, 20%, 25%, and finally 30% EtOAc/hexanes. There were closely eluting byproducts that eluted just before, and just after the desired product. Pure product containing fractions from the column were combined and concentrated to afford 4-bromofuran-2-carboxylic acid methoxymethylamide as an off-white solid (13.1 g, 44% yield over three steps). Impure product containing fractions were combined, concentrated, and re-chromatographed as before. Additional pure 4-bromofuran-2-carboxylic acid methoxymethylamide was obtained as an off-white solid (4.75 g, 16% yield over three steps). Some impure product fractions were obtained also. The total isolated yield for the three steps was 60%. $^1$H-NMR (400 MHz, CDCl$_3$): δ 7.60 (1H, d, J=0.8 Hz), 7.14 (1H, d, J=0.8 Hz), 3.77 (3H, s), 3.35 (3H, s).

E. In a similar manner as described above, other compounds of formula (Q) are prepared.

Preparation 11

Compounds of Formula (T)

A. A solution of N,N-diisopropylethylamine (26 mL, 150 mmol), diethylamine (20 mL, 190 mmol), and 4-(N,N-dimethylamino)pyridine (~50 mg, catalytic) in 300 mL $CH_2Cl_2$ was prepared in a 1 L round bottom flask equipped with a magnetic stirring-bar. The resulting solution was cooled in an ice bath and treated with 2-chloro-6-methylbenzoyl chloride. The flask and syringe that contained the acid chloride were then rinsed with additional $CH_2Cl_2$ (30 mL) which was also added to the reaction flask. After 10 minutes the ice bath was removed and the dark reaction mixture was allowed to warm to ambient temperature. After standing at ambient temperature for 16 hours, the reaction mixture was quenched by the addition of $H_2O$ (100 mL), and $CH_2Cl_2$ (1 L), and transferred to a separatory funnel. The layers were separated and the organic layer was washed with 1N HCl (aq.) (100 mL), $H_2O$ (100 mL), and finally saturated aqueous $NaHCO_3$ solution (100 mL). The organics were then dried over $Na_2SO_4$, filtered, and the filtrate concentrated under reduced pressure to afford a dark brown liquid. The crude product was purified by silica gel column chromatography eluting with a gradient from 0% to 30% ethyl acetate/hexane on silica. The product peak was collected to afford 2-chloro-N,N-diethyl-6-methyl-benzamide (24.6 g, 86% yield over two steps) as a brownish-yellow waxy solid. $^1$H-NMR (400 MHz, $CDCl_3$): δ 7.23-7.15 (2H, m), 7.12-7.08 (1H, m), 3.69-3.55 (2H, m), 3.14 (2H, q, J=7.3 Hz), 2.29 (s, 3H), 1.28 (3H, t, J=7.3 Hz), 1.09 (3H, t, J=7.3 Hz).

B. In a similar manner, other compounds of formula (T) are prepared.

Preparation 12

Compounds of Formula (U)

A. To a solution of diisopropylamine (3.8 mL, 27 mmol) in THF (85 mL) in a –10° C. bath was added a solution of butyllithium (17.0 mL of a 1.4 M solution in hexane, 23.8 mmol). After stirring at –10° C. for 10 minutes, the cooling bath was further cooled to –78° C. The resulting solution of LDA was then treated with a mixture of N,N-diethyl-5-fluoro-2-methyl-benzamide (3.48 g, 16.6 mmol) and 4-benzyloxy-N-methoxy-N-methylbenzamide (4.51 g, 16.6 mmol) as a solution in THF (25 mL) by cannula addition over ~8 minutes. The flask and cannula containing the benzamide mixture solution was then rinsed with additional THF (10 mL) which was added to the reaction to insure complete transfer. TLC analysis of the deep purple reaction solution after stirring for 15 minutes at –78° C. showed one main product spot. After stirring for 30 minutes at –78° C. the reaction was quenched by the addition of saturated aqueous $NH_4Cl$ (50 mL). The cooling bath was removed and the suspension was allowed to slowly warm to ambient temperature. After warming to ambient temperature, $H_2O$ was added to dissolve the solids that had formed, the reaction was diluted with $Et_2O$ (400 mL), and transferred to a separatory funnel. The resulting layers were separated, and the aqueous layer was extracted with $Et_2O$ (3×75 mL). The organic layers were combined, washed with saturated aqueous sodium chloride (100 mL), dried over $Na_2SO_4$, filtered and concentrated under reduced pressure to afford a pale yellow oil. The crude oil was purified by silica gel column chromatography eluting with a gradient from 0% to 30% EtOAc/hexane. Product-containing fractions from the column were combined and concentrated to afford 2-[2-(4-benzyloxyphenyl)-2-oxo-ethyl]-N,N-diethyl-5-fluoro-benzamide (4.74 g, 68% yield) as a pale yellow oil. $^1$H NMR analysis showed some impurities present.

$^1$H-NMR (400 MHz, $CDCl_3$): δ 7.99-7.95 (2H, m), 7.44-7.30 (5H, m), 7.21 (1H, dd, J=5.3, 8.6 Hz), 7.06-6.97 (3H, m), 6.94 (1H, dd, J=2.8, 8.6 Hz), 5.11 (2H, s), 4.3 (2H, broad hump), 3.41 (1H, broad hump), 3.14 (1H, broad hump), 1.06 (3H, t, J=7.1 Hz), 1.01 (3H, t, J=7.1 Hz).

B. In a similar manner, other compounds of formula (U) were prepared.

Preparation 13

Compounds of Formula (V)

A. In a 10 mL round bottomed flask equipped with a magnetic stir bar 2-[2-(4-benzyloxyphenyl)-2-oxo-ethyl]-6-chloro-N,N-diethylbenzamide (340 mg, 0.78 mmol) was treated with propionic acid (1.5 mL). The resulting mixture was stirred and heated to reflux in a 165° C. oil bath. As the reaction heated, the 2-[2-(4-benzyloxyphenyl)-2-oxo-thyl]-6-chloro-N,N-diethylbenzamide was dissolved in the propionic acid to afford a pale brown solution. After stirring at reflux for 88 hours, the reaction was analyzed by TLC, which showed no starting material remaining. The reaction was allowed to cool to ambient temperature during which time a mass of pale brown crystals were deposited on the walls of the reaction flask. The reaction mixture was diluted with ethyl acetate to dissolve the solids, and the resulting solution was washed with saturated aqueous $NaHCO_3$ solution. The basic aqueous solution was then extracted with EtOAc (3×20 mL). The combined organic extracts were washed with brine, dried over $Na_2SO_4$, filtered and concentrated under reduced pressure to afford an off-white solid. This material was quite clean by $^1$H NMR analysis and was further purified by recrystallization from EtOAc to afford 3-(4-benzyloxyphenyl)-8-chloro-isochromen-1-one (206 mg, 73% yield) as pale yellow crystals.

$^1$H-NMR (400 MHz, $CDCl_3$): δ 7.84-7.79 (2H, m), 7.54 (1H, t, J=7.8 Hz), 7.4-7.32 (7H, m), 7.07-7.03 (2H, m), 6.77 (1H, m), 5.13 (2H, m).

B. In a similar manner, other compounds of formula (V) were prepared.

EXAMPLE 1

Compounds of Formula (IA)

A. A mixture of trifluoromethanesulfonic acid 8-chloro-2-(2,4-dimethylbenzyl)-1-oxo-1,2-dihydroisoquinolin-3-yl ester (61.9 mg, 0.14 mmol), 4-phenoxyphenylboronic acid (45.9 mg, 0.21 mmol), and triphenylarsine (17.6 mg, 57.5 µmol) in THF (0.7 mL) under a nitrogen atmosphere was treated with bis-(acetonitrile) palladium (II) chloride (4.6 mg, 17.7 µmol) and aqueous sodium carbonate solution (0.7 mL of a 2 M solution) with vigorous stirring at ambient temperature. After 90 minutes stirring at ambient temperature, TLC analysis showed only a trace of starting trifluoromethanesulfonic acid 8-chloro-2-(2,4-dimethylbenzyl)-1-oxo-1,2-dihydroisoquinolin-3-yl ester remaining. The reaction was diluted with ether (20 mL), and water (10 mL). The basic aqueous layer was extracted with ether (3×10 mL). The combined organic extracts were washed with brine, dried over $Na_2SO_4$, filtered, and conc. to afford a yellow semi-solid. The material was purified by silica gel column chromatography eluting with a gradient from 0% to 10% ethyl acetate/hexane. The main peak was collected to afford 8-chloro-2-(2,4-dimethylbenzyl)-3-(4-phenoxyphenyl)-2H-isoquinolin-1-one (41 mg, 63% yield) as a brittle white foam contaminated with a small amount (<10%) of an impurity: $^1$H-NMR (400 MHz, $CDCl_3$): δ 7.51-7.49 (2H, m), 7.41-7.34 (3H, m), 7.18-7.11 (3H, m), 7.04-7.00 (2H, m), 6.94-6.84 (5H, m), 6.68 (1H, d, J=7.8 Hz), 6.42 (1H, s), 5.09 (2H, s), 2.24 (3H, s), 2.00 (3H, s) ppm.

B. In a similar manner, the following compounds of formula (I) were prepared:

2-biphenyl-4-ylmethyl-3-m-tolyl-2H-isoquinolin-1-one; $^1$H-NMR (400 MHz, $CDCl_3$): δ 8.5 (1H, d, J=8.4 Hz), 7.67

(1H, ddd, J=7.1, 7.1, 1.3 Hz), 7.55-7.48 (4H, m), 7.45-7.38 (4H, m), 7.35-7.28 (1H, m), 7.25-7.19 (2H, m), 7.06 (1H, d, J=7.1 Hz), 7.02-6.96 (3H, m), 6.46 (1H, s), 5.26 (2H, s), 2.29 (3H, s) ppm;

2-(2,4-dimethylbenzyl)-3-m-tolyl-2H-isoquinolin-1-one; $^1$H-NMR (400 MHz, CDCl$_3$): δ 8.49 (1H, d, J=7.8 Hz), 7.66 (1H, ddd, J=7.3, 7.3, 1.3 Hz), 7.54-7.47 (2H, m), 7.19-7.15 (2H, m), 7.02-6.95 (1H, m), 6.89 (1H, s), 6.83-6.88 (2H, m), 6.69 (1H, d, J=7.6 Hz), 6.46 (1H, s), 5.09 (2H, s), 2.23 (6H, d, J=4.0 Hz), 1.89 (3H, s) ppm;

2-benzyl-3-m-tolyl-2H-isoquinolin-1-one; $^1$H-NMR (400 MHz, CDCl$_3$): δ 8.49 (1H, d, J=8.1 Hz), 7.65 (1H, ddd, J=7.6, 7.6, 1.3 Hz), 7.53-7.47 (2H, m), 7.28-7.14 (5H, m), 7.05-6.99 (1H, m), 6.95-6.88 (3H, m), 6.44 (1H, s), 5.23 (2H, s), 2.27 (3H, s) ppm;

2-benzyl-3-thiophen-2-yl-2H-isoquinolin-1-one; $^1$H-NMR (400 MHz, CDCl$_3$): δ 8.47 (1H, d, J=8.1), 7.67 (1H, ddd, J=7.6, 7.6, 1.3 Hz), 7.56-7.49 (2H, m), 7.36 (1H, dd, J=5.3, 1.3 Hz), 7.28-7.16 (3H, m), 7.03-6.96 (3H, m), 6.91 (1H, dd, J=3.5, 1.0 Hz), 6.68 (1H, s), 5.36 (2H, s) ppm;

2-benzyl-3-furan-3-yl-2H-isoquinolin-1-one; $^1$H-NMR (400 MHz, CDCl$_3$): δ 8.46 (1H, d, J=8.1 Hz), 7.66 (1H, ddd, J=7.6, 7.6, 1.3 Hz), 7.54-7.47 (2H, m), 7.41 (1H, t, J=1.5 Hz), 7.4-7.38 (2H, m), 7.29-7.17 (3H, m), 7.04 (2H, d, J=7.1 Hz), 6.56 (1H, s), 6.30-6.26 (1H, m), 5.34 (2H, s) ppm;

2-(2,4-dimethylbenzyl)-3-thiophen-3-yl-2H-isoquinolin-1-one; $^1$H-NMR (400 MHz, CDCl$_3$): δ 8.48 (1H, d, J=8.1 Hz), 7.67 (1H, ddd, J=7.6, 7.6, 1.3 Hz), 7.57-7.47 (2H, m), 7.29-7.24 (1H, m), 7.19-7.15 (1H, m), 6.92 (1H,s), 6.9-6.85 (2H, m), 6.69 (1H, d, J=7.8 Hz), 6.58 (1H, s), 5.11 (2H, s), 2.26 (3H, s), 2.06 (3H, s) ppm;

2-(2,4-dimethylbenzyl)-3-furan-2-yl-2H-isoquinolin-1-one; $^1$H-NMR (400 MHz, CDCl$_3$): δ 8.45 (1H, d, J=8.1 Hz), 7.68 (1H, ddd, J=7.6, 7.6, 1.5 Hz), 7.57 (1H, d, J=7.8 Hz), 7.51 (1H, ddd, J=7.6, 7.6, 1.0 Hz), 6.96 (1H, s), 6.88-6.81 (2H, m), 6.66 (1H, d, J=7.8 Hz), 6.35-6.39 (1H, m), 6.33-6.29 (1H, m), 5.30 (2H, s), 2.25 (6H, s) ppm;

2-benzyl-3-(4-hydroxy-3,5-dimethylphenyl)-2H-isoquinolin-1-one; $^1$H-NMR (400 MHz, CDCl$_3$): δ 8.48 (1H, d, J=8.6 Hz), 7.65 (1H, ddd, J=7.1, 7.1, 1.0 Hz), 7.53-7.45 (2H, m), 7.23-7.15 (3H, m), 6.98-6.91 (2H, m), 6.76 (2H, s), 6.42 (1H, s), 5.22 (2H, s), 4.75 (1H, s), 2.17 (6H, s) ppm;

N-[4-(2-benzyl-1-oxo-1,2-dihydroisoquinolin-3-yl)phenyl]acetamide; $^1$H-NMR (400 MHz, CDCl$_3$): δ 8.48 (1H, d, J=8.6 Hz), 7.66 (1H, ddd, J=7.1, 7.1, 1.3 Hz), 7.55-7.44 (4H, m), 7.20-7.12 (5H, m), 6.95-6.89 (2H, m), 6.43 (1H, s), 5.25 (2H, s), 2.2 (3H, s) ppm;

2-(2,4-dimethylbenzyl)-3-(4-hydroxy-3,5-dimethylphenyl)-2H-isoquinolin-1-one; $^1$H-NMR (400 MHz, CDCl$_3$): δ 8.48 (1H, d, J=7.8 Hz), 7.69-7.62 (1H, m), 7.53-7.45 (2H, m), 6.89-6.84 (2H, m), 6.74-6.69 (3H, m), 6.44 (1H, s), 5.09 (2H, s), 4.75 (1H, s), 2.25 (3H, s), 2.12 (6H, s), 1.93 (3H, s) ppm;

3-(4-aminophenyl)-2-(2,4-dimethylbenzyl)-2H-isoquinolin-1-one; $^1$H-NMR (400 MHz, CDCl$_3$): δ 8.46 (1H, d, J=8.1 Hz), 7.65 (1H, ddd, J=7.6, 7.6, 1.0 Hz), 7.54-7.44 (2H, m), 6.97 (2H, d, J=8.1 Hz), 6.89-6.82 (2H, m), 6.66 (1H, d, J=7.6 Hz), 6.57 (2H, d, J=8.3 Hz), 6.47 (1H, s), 5.12 (2H, s), 2.24 (3H, s), 2.02 (3H, s) ppm;

2-(2,4-dimethylbenzyl)-3-(4-methoxyphenyl)-2H-isoquinolin-1-one; $^1$H-NMR (400 MHz, CDCl$_3$): δ 8.48 (1H, d, J=8.1 Hz), 7.67 (1H, ddd, J=7.6, 7.6, 1.3 Hz), 7.56-7.47 (2H, m), 7.15-7.08 (2H, m), 6.89-6.77 (4H, m), 6.66 (1H, d, J=8.1 Hz), 6.48 (1H, s), 5.10 (2H, s), 3.81 (3H, s), 2.25 (3H, s), 1.97 (3H, s) ppm;

2-benzyl-3-(4-hydroxyphenyl)-2H-isoquinolin-1-one; $^1$H-NMR (400 MHz, CDCl$_3$): δ 8.48 (1H, d, J=8.6 Hz), 7.66 (1H, ddd, J=7.4, 7.4, 1.3 Hz), 7.54-7.46 (2H, m), 7.21-7.14 (3H, m), 7.06 (2H, d, J=8.3 Hz), 6.95-6.9 (2H, m), 6.8-6.75 (2H, m), 6.44 (1H, s), 5.25 (2H, s), 5.19 (1H, s) ppm;

2-benzyl-3-(4-methoxyphenyl)-2H-isoquinolin-1-one; $^1$H-NMR (400 MHz, CDCl$_3$): δ 8.48 (1H, d, J=8.3 Hz), 7.68 (1H, ddd, J=7.1, 7.1, 1.3 Hz), 7.55-7.45 (2H, m), 7.22-7.15 (3H, m), 7.15-7.09 (2H, m), 6.95-6.90 (2H, m), 6.89 -6.83 (2H, m), 6.50 (1H, s), 5.27 (2H, s), 3.84 (3H, s) ppm;

2-benzyl-3-thiophen-3-yl-2H-isoquinolin-1-one; $^1$H-NMR (400 MHz, CDCl$_3$): δ 8.48 (1H, d, J=8.3 Hz), 7.70-7.60 (1H, m), 7.55-7.48 (2H, m), 7.45-7.40 (1H, m), 7.34-7.30 (1H, m), 7.25-7.16 (3H, m), 7.00-6.92 (3H, m), 6.55 (1H, s), 5.28 (2H, s) ppm;

2-(2,4-dimethylbenzyl)-3-(4-hydroxyphenyl)-2H-isoquinolin-1-one; $^1$H-NMR (400 MHz, CDCl$_3$): δ 8.48 (1H, d, J=8.1 Hz), 7.67 (1H, ddd, J=7.6, 7.6, 1.0 Hz), 7.54-7.47 (2H, m), 7.07-7.02 (2H, m), 6.87-6.83 (2H, m), 6.75-6.71 (2H, m), 6.65 (1H, d, J=8.6 Hz), 6.47 (1H, s), 5.10 (3H, s), 2.24 (3H, s), 1.97 (3H, s) ppm;

2-(2,4-dimethylbenzyl)-3-(4-hydroxy-3-methoxyphenyl)-2H-isoquinolin-1-one; $^1$H-NMR (400 MHz, CDCl$_3$): δ 8.5 (1H, d, J=8.1 Hz), 7.68 (1H, ddd, J=7.3, 7.3, 1.5 Hz), 7.56-7.48 (2H, m), 6.92-6.85 (3H, m), 6.84-6.79 (1H, m), 6.75 (1H, d, J=7.6 Hz), 6.49 (1H, s), 6.46 (1H, d, J=1.8 Hz), 5.63 (1H, s), 5.07 (2H, s), 3.41 (3H, s), 2.24 (3H, s), 1.94 (3H, s) ppm;

2-(2,4-dimethylbenzyl)-3-(3,5-dimethylphenyl)-2H-isoquinolin-1-one; $^1$H-NMR (400 MHz, CDCl$_3$): δ 8.49 (1H, d, J=8.1 Hz), 7.66 (1H, ddd, J=7.6, 7.6, 1.3 Hz), 7.53-7.46 (2H, m), 6.98 (1H, s), 6.89-6.83 (2H, m), 6.74-6.69 (3H, m), 6.45 (1H, s), 5.08 (2H, s), 2.24 (3H, s), 2.20 (3H, s), 1.88 (3H, s) ppm;

3-(3,5-bis-trifluoromethylphenyl)-2-(2,4-dimethylbenzyl)-2H-isoquinolin-1-one; $^1$H-NMR (400 MHz, CDCl$_3$): δ 8.55 (1H, d, J=7.6 Hz), 7.84 (1H, s), 7.72 (1H, ddd, J=7.6, 7.6, 1.3 Hz), 7.59 (1H, ddd, J=7.6, 7.6, 1.3 Hz), 7.54 (1H, d, J=7.8 Hz), 7.50 (2H, s), 6.86-6.79 (2H, m), 6.59 (1H, d, J=7.8 Hz), 6.46 (1H, s), 5.13 (2H, s), 2.23 (3H, s), 1.76 (3H, s) ppm;

2-(2,4-dimethylbenzyl)-3-thiophen-2-yl-2H-isoquinolin-1-one; $^1$H-NMR (400 MHz, CDCl$_3$): δ 8.47 (1H, d, J=8.1 Hz), 7.68 (1H, ddd, J=7.3, 7.3, 1.3 Hz), 7.57-7.49 (2H, m), 7.32 (1H, dd, J=5.1, 1.0 Hz), 6.97-6.91 (2H, m), 6.91-6.84 (2H, m), 6.72 (1H, s), 6.68 (1H, d, J=7.8 Hz), 5.20 (2H, s), 2.27 (3H, s), 2.10 (3H, s) ppm;

2-(2,4-dimethylbenzyl)-3-phenyl-2H-isoquinolin-1-one; $^1$H-NMR (400 MHz, CDCl$_3$): δ 8.49 (1H, d, J=8.1 Hz), 7.67 (1H, ddd, J=7.3, 7.3, 1.3 Hz), 7.55-7.48 (2H, m), 7.40-7.27 (3H, m), 7.20-7.15 (2H, m), 6.87-6.83 (2H, m), 6.67 (1H, d, J=8.3 Hz), 6.48 (2H, s), 5.10 (2H, s), 2.24 (3H, s), 1.91 (3H, s) ppm;

4-[2-(2,4-dimethylbenzyl)-1-oxo-1,2-dihydroisoquinolin-3-yl]benzoic acid methyl ester; $^1$H-NMR (400 MHz, CDCl$_3$): δ 8.50 (1H, d, J=8.3 Hz), 7.96 (2H, d, J=8.34 Hz), 7.69 (1H, ddd, J=7.1, 7.1, 1.3 Hz), 7.57-7.50 (2H, m), 7.30-7.24 (1H, m), 6.88-6.83 (2H, m), 6.64 (1H, d, J=8.3 Hz), 6.47 (1H, s), 5.08 (2H, s), 3.93 (3H, s), 2.24 (3H, s), 1.89 (3H, s) ppm;

2-(2,4-dimethylbenzyl)-3-(4-methoxy-3-trifluoromethylphenyl)-2H-isoquinolin-1-one; $^1$H-NMR (400 MHz, CDCl$_3$): δ 8.5 (1H, d, J=7.8 Hz), 7.68 (1H, ddd, J=7.3, 7.3, 1.3 Hz), 7.56-7.50 (2H, m), 7.34-7.28 (2H, m), 6.92-6.83 (3H, m), 6.67-6.62 (1H, m), 6.44 (1H, s), 5.09 (2H, s), 3.91 (3H, s), 2.25 (3H, s), 1.90 (3H, s) ppm;

2-(2,4-dimethylbenzyl)-3-[3-methyl-4-(tetrahydropyran-2-yloxy)phenyl]-2H-isoquinolin-1-one; $^1$H-NMR (400 MHz, CDCl$_3$): δ 8.47 (1H, d, J=7.8 Hz), 7.65 (1H, ddd, J=7.6, 7.6, 1.3 Hz), 7.53-7.45 (2H, m), 6.97 (2H, d, J=1.3 Hz), 6.89-6.83 (3H, m), 6.69 (1H, d, J=8.6 Hz), 6.46 (1H, s), 5.43 (1H, t, J=3.0 Hz), 5.10 (2H, dd, J=17.2, 26.8 Hz), 3.91-3.81 (1H, m), 3.65-3.55 (1H, m), 2.25 (3H, s), 2.13 (3H, s), 2.07-1.97 (1H, m), 1.95 (3H, s), 1.93-1.83 (2H, m), 1.59-1.75 (3H, m);

N-{4-[2-(2,4-dimethylbenzyl)-1-oxo-1,2-dihydroisoquinolin-3-yl]phenyl}-acetamide; $^1$H-NMR (400 MHz, CDCl$_3$): δ 8.31 (1H, d, J=8.1 Hz), 7.60 (1H, ddd, J=7.3, 7.3, 1.3 Hz), 7.50-7.33 (4H, m), 7.17 (1H, s), 7.09 (2H, d, J=8.6 Hz), 6.81 (1H, s), 6.77 (1H, d, J=7.8 Hz), 6.53 (1H, d, J=7.6 Hz), 6.40 (1H, s), 4.98 (2H, s), 2.16 (3H, s), 2.06 (3H, s), 1.90 (3H, s) ppm;

4-[2-(2,4-dimethylbenzyl)-1-oxo-1,2-dihydroisoquinolin-3-yl]benzonitrile; $^1$H-NMR (400 MHz, CDCl$_3$): δ 8.51 (1H, d, J=8.1), 7.71 (1H, ddd, J=7.6, 7.6, 1.5 Hz), 7.60-7.52 (4H, m), 7.25-7.3 (2H, m), 6.88-6.82 (2H, m), 6.61 (1H, d, J=8.3 Hz), 6.45 (1H, s), 5.07 (2H, s), 2.25 (3H, s), 1.89 (3H, s) ppm;

2-(2,4-dimethylbenzyl)-3-(4-hydroxy-3-methylphenyl)-2H-isoquinolin-1-one; $^1$H-NMR (400 MHz, CDCl$_3$): δ 8.48 (1H, d, J=8.1 Hz), 7.66 (1H, ddd, J=7.6, 7.6, 1.3 Hz), 7.54-7.45 (2H, m), 6.92-6.83 (4H, m), 6.67 (2H, t, J=8.6 Hz), 6.45 (1H, s), 5.09 (2H, s), 4.83 (1H, s), 2.25 (3H, s), 2.12 (3H, s), 1.95 (3H, s) ppm;

2-(2,4-dimethylbenzyl)-3-(3-trifluoromethylphenyl)-2H-isoquinolin-1-one; $^1$H-NMR (400 MHz, CDCl$_3$): δ 8.52 (1H, d, J=8.1 Hz), 7.70 (1H, ddd, J=7.6, 7.6, 1.3 Hz), 7.62 (1H, d, J=7.6 Hz), 7.58-7.51 (2H, m), 7.45-7.30 (3H, m), 6.88-6.80 (2H, m), 6.63 (1H, d, J=7.6 Hz), 6.46 (1H, s), 5.10 (2H, s), 2.24 (3H, s), 1.82 (3H, s) ppm;

2-(4-methylbenzyl)-3-(3-trifluoromethylphenyl)-2H-isoquinolin-1-one; $^1$H-NMR (400 MHz, CDCl$_3$): δ 8.55-8.49 (1H, m), 7.74-7.63 (2H, m), 7.60-7.30 (4H, m), 7.00-6.93 (2H, m), 6.75-6.87 (2H, m), 6.45-6.40 (1H, m), 5.27-5.12 (2H, m), 2.30-2.24 (3H, m) ppm;

2-benzyl-3-(3-trifluoromethylphenyl)-2H-isoquinolin-1-one; $^1$H-NMR (400 MHz, CDCl$_3$): δ 8.52 (1H, d, J=8.6 Hz), 7.73-7.63 (2H, m), 7.59-7.50 (2H, m), 7.46 (1H, t, J=7.6 Hz), 7.40-7.34 (2H, m), 7.20-7.14 (3H, m), 6.86-6.80 (1H, m), 6.44 (2H, s) ppm;

3-benzo[b]thiophen-2-yl-2-(4-methylbenzyl)-2H-isoquinolin-1-one; $^1$H-NMR (400 MHz, CDCl$_3$): δ 8.48 (1H, d, J=8.3 Hz), 7.86-7.79 (1H, m), 7.76-7.65 (2H, m), 7.57-7.50 (2H, m), 7.43-7.35 (2H, m), 7.16 (1H, s), 7.02 (2H, d, J=7.8 Hz), 6.93 (2H, d, J=8.1 Hz), 6.75 (1H, s), 5.37 (2H, s), 2.29 (3H, s) ppm;

2-(4-methylbenzyl)-3-(4-phenoxyphenyl)-2H-isoquinolin-1-one; $^1$H-NMR (400 MHz, CDCl$_3$): δ 8.48 (1H, d, J=8.6 Hz), 7.70-7.62 (1H, m), 7.55-7.46 (2H, m), 7.43-7.23 (2H, m), 7.21-7.13 (3H, m), 7.10-7.04 (3H, m), 7.03-6.91 (3H, m), 6.86-6.80 (2H, m), 6.45 (1H, s), 5.23 (2H, s), 2.26 (3H, s) ppm;

3-benzofuran-2-yl-2-(4-methylbenzyl)-2H-isoquinolin-1-one; $^1$H-NMR (400 MHz, CDCl$_3$): δ 8.49 (1H, d, J=8.1 Hz), 7.69 (1H, ddd, J=7.6, 7.6, 1.3 Hz), 7.60-7.48 (4H, m), 7.40-7.24 (3H, m), 6.98 (3H, s), 6.91 (1H, s), 6.81 (1H, s), 5.46 (2H, s), 2.26 (3H, s) ppm;

3-(4-bromophenyl)-2-(2,4-dimethylbenzyl)-2H-isoquinolin-1-one; $^1$H-NMR (400 MHz, CDCl$_3$): δ 8.49 (1H, d, J=7.8 Hz), 7.68 (1H, ddd, J=7.1, 7.1, 1.3 Hz), 7.57-7.49 (2H, m), 7.42 (2H, d, J=8.3 Hz), 7.05 (2H, d, J=8.3 Hz), 6.90-6.82 (2H, m), 6.67-6.61 (1H, m), 6.45 (1H, s), 5.07 (2H, s), 2.25 (3H, s), 1.95 (3H, s) ppm;

2-(2,4-dimethylbenzyl)-3-(4-phenoxyphenyl)-2H-isoquinolin-1-one; $^1$H-NMR (400 MHz, CDCl$_3$): δ 8.48 (1H, d, J=7.8 Hz), 7.67 (1H, ddd, J=7.3, 7.3, 1.3 Hz), 7.56-7.48 (2H, m), 7.40-7.32 (2H, m), 7.19-7.10 (3H, m), 7.06-7.00 (2H, m), 6.93-6.82 (4H, m), 6.66 (1H, d, J=7.6 Hz), 6.49 (1H, s), 5.13 (2H, s), 2.24 (3H, s), 1.99 (3H, s) ppm;

3-benzofuran-2-yl-2-(2,4-dimethylbenzyl)-2H-isoquinolin-1-one; $^1$H-NMR (400 MHz, CDCl$_3$): δ 8.49 (1H, d, J=8.3 Hz), 7.71 (1H, ddd, J=7.3, 7.3, 1.3 Hz), 7.62 (1H, d, J=7.8 Hz), 7.59-7.49 (2H, m), 7.45 (1H, d, J=8.1 Hz), 7.33 (2H, ddd, J=7.8, 7.8, 1.0 Hz), 7.02 (1H, s), 6.94 (1H, s), 6.84 (1H, d, J=7.8 Hz), 6.71 (2H, d, J=8.3 Hz), 5.40 (2H, s), 2.25 (3H, s), 2.20 (3H, s) ppm;

3-benzo[b]thiophen-2-yl-2-(2,4-dimethylbenzyl)-2H-isoquinolin-1-one; $^1$H-NMR (400 MHz, CDCl$_3$): δ 8.49 (1H, d, J=8.1 Hz), 7.83-7.76 (1H, m), 7.74-7.65 (2H, m), 7.62-7.50 (2H, m), 7.40-7.35 (2H, m), 7.10 (1H, s), 6.95-6.87 (2H, m), 6.80 (1H, s), 6.72 (1H, d, J=7.8 Hz), 5.27 (2H, s), 2.28 (3H, s), 2.06 (3H, s) ppm;

2-(2,4-dimethylbenzyl)-3-(4-methylsulfanylphenyl)-2H-isoquinolin-1-one; H-mR (400 MHz, CDCl$_3$): δ 8.48 (1H, d, J=7.8 Hz), 7.67 (1H, ddd, J=7.3, 7.3, 1.3 Hz), 7.55-7.48 (2H, m), 7.18-7.08 (4H, m), 6.89-6.83 (2H, m), 6.66 (1H, d, J=7.6 Hz), 6.47 (1H, s), 5.09 (2H, s), 2.49 (3H, s), 2.25 (3H, s), 1.97 (3H, s) ppm;

2-(4-methyl-benzyl)-3-(4-methylsulfanylphenyl)-2H-isoquinolin-1-one; $^1$H-NMR (400 MHz, CDCl$_3$): δ 8.47 (1H, d, J=8.6), 7.65 (1H, ddd, J=7.6, 7.6, 1.3 Hz), 7.53-7.46 (2H, m), 7.23-7.18 (2H, m), 7.16-7.12 (2H, m), 6.99 (2H, d, J=8.1 Hz), 6.83 (2H, d, J=7.8 Hz), 6.42 (1H, s), 5.20 (2H, s), 2.52 (3H, s), 2.27 (3H, s) ppm;

3-(4-bromophenyl)-2-(4-methylbenzyl)-2H-isoquinolin-1-one; $^1$H-NMR (400 MHz, CDCl$_3$): δ 8.49 (1H, d, J=7.8 Hz), 7.66 (1H, ddd, J=7.6, 7.6, 1.3 Hz), 7.55-7.44 (4H, m), 7.08 (2H, d, J=8.3 Hz), 6.99 (2H, d, J=7.8 Hz), 6.80 (2H, d, J=8.1 Hz), 6.41 (1H, s), 5.18 (2H, s), 2.27 (3H, s) ppm;

2-(2,4-dimethylbenzyl)-3-(3-methyl-4-phenoxyphenyl)-2H-isoquinolin-1-one; $^1$H-NMR (400 MHz, CDCl$_3$): δ 8.50 (1H, d, J=8.1 Hz), 7.68 (1H, ddd, J=7.6, 7.6, 1.5 Hz), 7.55-7.48 (2H, m), 7.37-7.30 (2H, m), 7.13-7.06 (1H, m), 7.00-6.89 (4H, m), 6.89-6.83 (2H, m), 6.76 (1H, d, J=8.1 Hz), 6.69 (1H, d, J=8.3 Hz), 6.49 (1H, s), 5.14 (2H, s), 2.24 (3H, s), 2.13 (3H, s), 1.97 (3H, s) ppm;

2-benzyl-3-(4-phenoxyphenyl)-2H-isoquinolin-1-one; $^1$H-NMR (400 MHz, CDCl$_3$): δ 8.49 (1H, d, J=8.3 Hz), 7.67 (1H, ddd, J=7.6, 7.6, 1.5 Hz), 7.54-7.48 (2H, m), 7.42-7.35 (2H, m), 7.22-7.12 (6H, m), 7.08-7.04 (2H, m), 6.96-6.91 (4H, m), 6.46 (1H, s), 5.28 (2H, s) ppm;

5-chloro-2-(2,4-dimethylbenzyl)-3-(4-phenoxyphenyl)-2H-isoquinolin-1-one; $^1$H-NMR (400 MHz, CDCl$_3$): δ 8.41 (1H, d, J=8.1 Hz), 7.73 (1H, dd, J=7.6, 1.0 Hz), 7.45-7.34 (3H, m), 7.19-7.12 (3H, m), 7.06-7.01 (2H, m), 6.96-6.80 (6H, m), 6.64 (1H, d, J=7.8 Hz), 5.13 (2H, s), 2.24 (3H, s), 2.00 (3H, s) ppm;

5-chloro-2-(4-methylbenzyl)-3-(4-phenoxyphenyl)-2H-isoquinolin-1-one; $^1$H-NMR (400 MHz, CDCl$_3$): δ 8.40 (1H, d, J=8.3 Hz), 7.74-7.69 (1H, m), 7.44-7.35 (3H, m), 7.23-7.14 (3H, m), 7.10-7.05 (2H, m), 7.02-6.94 (2H, m), 6.85-6.78 (3H, m), 5.23 (2H, s), 2.27 (3H, s) ppm;

5-chloro-2-(2,4-dimethylbenzyl)-3-m-tolyl-2H-isoquinolin-1-one; $^1$H-NMR (400 MHz, CDCl$_3$): δ 8.42 (1H, d, J=8.3 Hz), 7.77-7.72 (1H, m), 7.43 (1H, t, J=7.8 Hz), 7.20 (2H, d, J=4.8 Hz), 7.04-6.98 (1 H, m), 6.92 (1H, s), 6.89-6.84 (3H, m), 6.65 (1H, d, J=8.3 Hz), 5.10 (2H, s), 1.90 (3H, s) ppm;

5-chloro-2-(4-methylbenzyl)-3-m-tolyl-2H-isoquinolin-1-one; $^1$H-NMR (400 MHz, CDCl$_3$): δ 8.41 (1H, d, J=8.1 Hz), 7.71 (1H, dd, J=7.6, 1.3 Hz), 7.40 (1H, t, J=7.8 Hz), 7.29-7.23 (2H, m), 7.09-7.03 (1H, m), 7.01-6.96 (3H, m), 6.80 (3H, d, J=7.8 Hz), 5.18 (2H, s), 2.31 (3H, s), 2.27 (3H, s) ppm;

5-chloro-2-(2,4-dimethylbenzyl)-3-phenyl-2H-isoquinolin-1-one; $^1$H-NMR (400 MHz, CDCl$_3$): δ 8.42 (1H, d, J=8.1 Hz), 7.73 (1H, dd, J=7.6, 1.2 Hz), 7.45-7.36 (2H, m), 7.34-7.28 (2H, m), 7.22-7.17 (2H, m), 6.89-6.81 (3H, m), 6.65 (1H, d, J=8.3 Hz), 5.09 (2H, s), 2.25 (3H, s), 1.91 (3H, s) ppm;

5-chloro-2-(4-methylbenzyl)-3-phenyl-2H-isoquinolin-1-one; $^1$H-NMR (400 MHz, CDCl$_3$): δ 8.41 (1H, d, J=8.3 Hz), 7.76-7.69 (1H, m), 7.60-7.51 (1H, m), 7.47-7.30 (6H, m), 6.98 (2H, d, J=8.1 Hz), 6.82-6.76 (3H, m), 5.20 (2H, s), 2.27 (3H, s) ppm;

2-(2,4-dimethylbenzyl)-5-fluoro-3-(4-phenoxyphenyl)-2H-isoquinolin-1-one; $^1$H-NMR (400 MHz, CDCl$_3$): δ 8.26 (1H, d, J=7.8 Hz), 7.48-7.27 (4H, m), 7.19-7.10 (3H, m), 7.07-7.00 (2H, m), 6.77-6.78 (7H, m), 6.70 (1H, s), 6.65 (1H, d, J=7.8 Hz), 5.13 (2H, s), 2.24 (3H, s), 2.00 (3H, s) ppm;

2-benzyl-5-fluoro-3-(4-phenoxyphenyl)-2H-isoquinolin-1-one; $^1$H-NMR (400 MHz, CDCl$_3$): δ 8.27 (1H, d, J=7.8 Hz), 7.47-7.32 (4H, m), 7.21-7.12 (6H, m), 7.09-7.04 (2H, m), 6.97-6.91 (4H, m), 6.66 (1H, s), 5.28 (2H, s) ppm;

2-(2,4-dimethylbenzyl)-5-fluoro-3-phenyl-2H-isoquinolin-1-one; $^1$H-NMR (400 MHz, CDCl$_3$): δ 8.27 (1H, d, J=7.6 Hz), 7.48-7.27 (5H, m), 7.21-7.16 (2H, m), 6.89-6.83 (2H, m), 6.69 (1H, s), 6.66 (1H, d, J=8.1 Hz), 5.10 (2H, s), 2.25 (3H, s), 1.91 (3H, s) ppm;

8-chloro-2-(2,4-dimethylbenzyl)-3-phenyl-2H-isoquinolin-1-one; $^1$H-NMR (400 MHz, CDCl$_3$): δ 7.52-7.47 (2H, m), 7.43-7.33 (2H, m), 7.32-7.24 (2H, m), 7.20-7.15 (2H, m), 6.89-6.81 (2H, m), 6.68 (1H, d, J=8.1 Hz), 6.41 (1H, s), 5.06 (2H, s), 2.24 (3H, s), 1.91 (3H, s) ppm;

8-chloro-2-(2,4-dimethylbenzyl)-3-m-tolyl-2H-isoquinolin-1-one; $^1$H-NMR (400 MHz, CDCl$_3$): δ 7.51-7.47 (2H, m), 7.41-7.36 (1H, m), 7.19-7.15 (2H, m), 7.00-6.96 (1H, m), 6.91-6.82 (3H, m), 6.71 (1H, d, J=7.8 Hz), 6.39 (1H, s), 5.05 (2H, s), 2.24 (6H, d, J=3.5 Hz), 1.89 (3H, s) ppm;

2-benzyl-8-chloro-3-(4-phenoxyphenyl)-2H-isoquinolin-1-one; H-NMR (400 MHz, CDCl$_3$): δ 7.51-7.47 (2H, m), 7.42-7.34 (3H, m), 7.22-7.10 (6H, m), 7.05 (2H, d, J=7.8 Hz), 6.97-6.90 (4H, m), 6.39 (1H, s), 5.24 (2H, s) ppm;

2-benzyl-8-chloro-3-m-tolyl-2H-isoquinolin-1-one; $^1$H-NMR (400 MHz, CDCl$_3$): δ 7.51-7.47 (2H, m), 7.38-7.34 (1H, m), 7.24-7.15 (5H, m), 7.03-6.99 (1H, m), 6.95-6.90 (3H, m), 6.37 (1H, s), 5.19 (2H, s), 2.28 (3H, s) ppm; and 2-benzyl-8-chloro-3-phenyl-2H-isoquinolin-1-one; $^1$H-NMR (400 MHz, CDCl$_3$): δ 7.51-7.48 (2H, m), 7.42-7.30 (4H, m), 7.22-7.14 (5H, m), 6.94-6.89 (2H, m), 6.38 (1H, s), 5.22 (2H, s) ppm.

C. In a similar manner, other compounds of formula (I) are prepared.

EXAMPLE 2

Compounds of Formula (IB)

A. To a solution of diisopropylamine (1.2 mL, 8.56 mmol) in THF (15 mL) at 0° C. was added n-butyllithium (5.2 mL of a 1.6 M solution in hexane, 8.32 mmol). After stirring at 0° C. for 10 minutes the resulting lithium diisopropylamide solution was treated with a solution of 2-methyl-N-(4-methylbenzyl)benzamide (616 mg, 2.57 mmol) in THF (20 mL) over 15 min. The resulting deep brown-red solution was stirred at 0° C. for 55 minutes at which time it was treated with a solution of 3-methylbenzoic acid methyl ester (0.39 mL, 2.76 mmol) in THF (20 mL) over 20 minutes. After an additional 1 hour at 0° C. the reaction was quenched by the addition of 3N HCl (25 mL). The biphasic mixture was then heated to reflux with vigorous stirring. After 75 minutes at reflux the reaction mixture was allowed to cool to ambient temperature overnight. After cooling overnight, the reaction was concentrated to remove most of the THF. The resulting residue was diluted with ether (100 mL), and water (50 mL), and then basified by careful addition of solid Na$_2$CO$_3$. The basic aqueous was extracted with ether (3×40 mL), combined organics were washed with brine (50 mL), dried over Na$_2$CO$_3$, filtered, and concentrated to afford a yellow oil. The crude product was purified by silica gel column chromatography on a Jones Flashmaster instrument eluting with a gradient from 0% to 6% ethyl acetate/hexane on a 50 g silica column. The product peak was collected to afford 2-(4-methylbenzyl)-3-m-tolyl-2H-isoquinolin-1-one (408 mg, 47% yield) as a yellow oil that slowly solidified to a waxy solid:

$^1$H-NMR (400 MHz, CDCl$_3$): δ 8.49 (1H, d, J=8.6 Hz), 7.67-7.62 (1H, m), 7.51-7.46 (2H, m), 7.25-7.19 (2H, m), 7.05-7.01 (1H, m) 7.00-6.95 (3H, m), 6.81 (2H, d, J=8.1 Hz), 6.43 1H, s), 5.19 (2H, br s), 2.29 (3H, s), 2.26 (3H, s) ppm.

B. In a similar manner, the following compounds of formula (Ib) were prepared:

2-benzyl-8-methyl-3-m-tolyl-2H-isoquinolin-1-one; $^1$H-NMR (400 MHz, CDCl$_3$): δ 7.48 (1H, t, J=7.6 Hz), 7.31 (1H, d, J=8.1 Hz), 7.25-7.15 (5H, m), 7.04-6.99 (1H, m), 6.96-6.90 (3H, m), 6.37 (1H, s), 5.17 (2H, s), 2.97 (3H, s), 2.27 (3H, s) ppm;

8-methyl-2-(4-methylbenzyl)-3-m-tolyl-2H-isoquinolin-1-one; $^1$H-NMR (400 MHz, CDCl$_3$): δ 7.47 (1H, t, J=7.6 Hz), 7.30 (1H, d, J=7.6 Hz), 7.25-7.16 (4H, m), 7.06-6.95 (4H, m), 6.82 (2H, d, J=8.1 Hz), 6.35 (1H, s), 5.13 (2H, s), 2.96 (3H, s), 2.28 (6H, d, J=6.1 Hz) ppm;

2-(2,4-dimethylbenzyl)-8-methyl-3-m-tolyl-2H-isoquinolin-1-one; $^1$H-NMR (400 MHz, CDCl$_3$): δ 7.49 (1H, t, J=7.6 Hz), 7.33 (1H, d, J=7.8 Hz), 7.17-7.14 (2H, m), 7.00-6.95 (1H, m), 6.92 (1H, s), 6.89-6.84 (2H, m), 6.70 (1 H, d, J=7.8 Hz), 6.40 (1H, s), 5.03 (2H, s), 2.96 (3H, s), 2.24 (6H, d, J=6.8 Hz), 1.91 (3H, s) ppm;

2-benzyl-8-methyl-3-phenyl-2H-isoquinolin-1-one; $^1$H-NMR (400 MHz, CDCl$_3$): δ 7.51-7.45 (1H, m), 7.41-7.28 (4H, m), 7.25-7.13 (6H, m), 6.94-6.89 (2H, m), 6.38 (1H, s), 5.19 (2H, s), 2.97 (3H, s) ppm;

2-benzyl-8-methyl-3-(4-phenoxyphenyl)-2H-isoquinolin-1-one; $^1$H-NMR (400 MHz, CDCl$_3$): δ 7.49 (1H, t, J=7.8 Hz), 7.40-7.35 (2H, m), 7.34-7.30 (1H, m), 7.25-7.11 (7H, m), 7.07-7.03 (2H, m), 6.97-6.89 (4H, m), 6.39 (1H, s), 5.22 (2H, s), 2.96 (3H, s) ppm;

8-methyl-2-(4-methylbenzyl)-3-phenyl-2H-isoquinolin-1-one; $^1$H-NMR (400 MHz, CDCl$_3$): δ 7.48 (1H, t, J=7.8 Hz), 7.41-7.29 (4H, m), 7.25-7.20 (3H, m), 7.00-6.96 (2H, m), 6.83-6.79 (2H, m), 6.37 (1H, s), 5.15 (2H, s), 2.96 (3H, s), 2.27 (3H, s) ppm;

8-methyl-2-(4-methylbenzyl)-3-(4-phenoxyphenyl)-2H-isoquinolin-1-one; $^1$H-NMR (400 MHz, CDCl$_3$): δ 7.51-7.45 (1H, m), 7.41-7.34 (2H, m), 7.34-7.29 (2H, m), 7.19-7.13 (3H, m), 7.08-7.04 (2H, m), 7.02-6.97 (2H, m), 6.96-6.90 (2H m), 6.86-6.81 (2H, m), 6.38 (1H, s), 5.18 (2H, s), 2.96 (3H, s), 2.27 (3H, s) ppm;

2-(2,4-dimethylbenzyl)-8-methyl-3-phenyl-2H-isoquinolin-1-one; $^1$H-NMR (400 MHz, CDCl$_3$): δ 7.50 (1H, t, J=7.8 Hz), 7.38-7.31 (3H, m), 7.3-7.25 (3H, m), 7.20-7.16 (2H, m), 6.89-6.83 (2H, m), 6.68 (1H, d, J=7.8 Hz), 6.41 (1H, s), 5.03 (2H, s), 2.96 (3H, s), 2.25 (3H, s), 1.93 (3H, s) ppm;

2-(2,4-dimethylbenzyl)-8-methyl-3-(4-phenoxyphenyl)-2H-isoquinolin-1-one; $^1$H-NMR (400 MHz, CDCl$_3$): δ 7.50 (1H, t, J=7.8 Hz), 7.39-7.32 (3H, m), 7.17-7.11 (3H, m), 7.04-6.99 (2H, m), 6.90-6.84 (4H, m), 6.67 (1H, d, J=8.3 Hz), 6.42 (1H, s), 5.07 (2H, s), 2.95 (3H, s), 2.24 (3H, s), 2.01 (3H, s) ppm;

2-(2,4-dimethylbenzyl)-7-methyl-3-phenyl-2H-isoquinolin-1-one; $^1$H-NMR (400 MHz, CDCl$_3$): δ 8.30 (1H, s), 7.53-7.49 (1H, m), 7.46-7.41 (1H, m), 7.38-7.32 (1H, m), 7.31-7.27 (2H, m), 7.19-7.14 (2H, m), 6.86-6.81 (2H, m), 6.68-6.63 (1H, m), 6.45 (1H, s), 5.09 (2H, s), 2.52 (3H, s), 2.24 (3H, s), 1.90 (3H, s) ppm;

2-(2,4-dimethylbenzyl)-7-methyl-3-(4-phenoxyphenyl)-2H-isoquinolin-1-one; $^1$H-NMR (400 MHz, CDCl$_3$): δ 8.29 (1H, s), 7.50 (1H, dd, J=8.1, 1.7 Hz), 7.43 (1H, d, J=8.1 Hz), 7.39-7.34 (2H, m), 7.18-7.09 (3H, m), 7.04-7.00 (2H, m), 6.91-6.81 (4H, m), 6.65 (1H, d, J=7.8 Hz), 6.46 (1H, s), 5.13 (2H, s), 2.52 (3H, s), 2.23 (3H, s), 1.99 (3H, s) ppm;

2-(2,4-dimethylbenzyl)-7-methyl-3-m-tolyl-2H-isoquinolin-1-one; $^1$H-NMR (400 MHz, CDCl$_3$): δ 8.30 (1H, s), 7.50 (1H, dd, J=8.1, 1.77 Hz), 7.43 (1H, d, J=8.1 Hz), 7.18-7.14 (2H, m), 7.00-6.95 (1H, m), 6.88(1H, s), 6.87-6.82 (2H, m), 6.68 (1H, d, J=8.3 Hz), 6.43 (1H, s), 5.08 (2H, s), 2.51 (3H, s), 2.23 (6H, d, J=5.8 Hz), 1.88 (3H, s) ppm;

7-methyl-2-(4-methylbenzyl)-3-phenyl-2H-isoquinolin-1-one; $^1$H-NMR (400 MHz, CDCl$_3$): δ 8.29 (1H, s), 7.51-7.46 (1H, m), 7.43-7.30 (4H, m), 6.96 (2H, d, J=7.8 Hz), 6.79 (2H, d, J=8.1 Hz), 6.41 (1H, s), 5.20 (2H, s), 2.51 (3H, s), 2.26 (3H, s) ppm;

7-methyl-2-(4-methylbenzyl)-3-(4-phenoxyphenyl)-2H-isoquinolin-1-one; $^1$H-NMR (400 MHz, CDCl$_3$): δ 8.29 (1H, s), 7.52-7.46 (1H, m), 7.44-7.35 (3H, m), 7.20-7.13 (3H, m), 7.10-7.04 (2H, m), 6.96 (4H, dd, J=16.2, 17.8 Hz), 6.82 (2H, d, J=7.8 Hz), 6.42 (1H, s), 5.23 (2H, s), 2.51 (3H, s), 2.26 (3H, s) ppm;

7-methyl-2-(4-methylbenzyl)-3-m-tolyl-2H-isoquinolin-1-one; $^1$H-NMR (400 MHz, CDCl$_3$): δ 8.29 (1H, s), 7.48 (1H, dd, J=8.1, 1.8 Hz), 7.40 (1H, d, J=7.8 Hz), 7.25-7.17 (2H, m), 7.05-7.00 (1H, m), 7.00-6.94 (3H, m), 6.80 (2H, d, J=8.1 Hz), 6.40 (1H, s), 5.18 (2H, s) ppm;

7-chloro-2-(2,4-dimethylbenzyl)-3-m-tolyl-2H-isoquinolin-1-one; $^1$H-NMR (400 MHz, CDCl$_3$): δ 8.46 (1H, s), 7.61 (1H, dd, J=8.6, 2.3 Hz), 7.46 (1H, d, J=8.3 Hz), 7.18 (2H, d, J=4.8 Hz), 7.00-6.94 (1H, m), 6.89-6.83 (3H, m), 6.65 (1H, d, J=7.8 Hz), 6.43 (1H, s), 5.07 (2H, s), 2.24 (6H, d, J=6.1 Hz), 1.88 (3H, s) ppm;

2-benzyl-7-methyl-3-(4-phenoxyphenyl)-2H-isoquinolin-1-one; $^1$H-NMR (400 MHz, CDCl3): δ 8.29 (1H, s), 7.49 (1H, m), 7.43-7.35 (3H, m), 7.20-7.11 (6H, m), 7.07-7.06 (2H, m), 6.94-6.90 (4H, m), 6.43 (1H, m), 5.27 (2H, s), 2.51 (3H, s) ppm;

2-benzyl-7-methyl-3-m-tolyl-2H-isoquinolin-1-one; $^1$H-NMR (400 MHz, CDCl$_3$): δ 8.30 (1H, s), 7.50-7.46 (1H, m), 7.42-7.38 (1H, m), 7.25-7.14 (5H, m), 7.03-6.99 (1H, m), 6.94-6.89 (3H, m), 6.41 (1H, m), 5.30 (2H, m), 2.51 (3H, s), 2.27 (3H, s) ppm;

2-benzyl-7-methyl-3-phenyl-2H-isoquinolin-1-one; $^1$H-NMR (400 MHz, CDCl$_3$): δ 8.30 (1H, s), 7.51-7.47 (1H, m), 7.43-7.36 (2H, m), 7.35-7.30 (2H, m), 7.21-7.14 (5H, m), 6.91-6.87 (2H, m), 6.42 (1H, s), 5.25 (2H, s), 2.51 (3H, s) ppm;

2-benzyl-6-methyl-3-(4-phenoxyphenyl)-2H-isoquinolin-1-one; $^1$H-NMR (400 MHz, CDCl$_3$): δ 8.37 (1H, d, J=8.1 Hz), 7.41-7.24 (4H, m), 7.21-7.09 (6H, m), 7.08-7.02 (2H, m), 6.96-6.89 (4H, m), 6.38 (1H, s), 5.26 (2H, m), 2.48 (3H, s) ppm;

2-benzyl-6-methyl-3-m-tolyl-2H-isoquinolin-1-one; $^1$H-NMR (400 MHz, CDCl$_3$): δ 8.37 (1H, d, J=8.3 Hz), 7.34-7.30 (1H, m), 7.29-7.25 (1H, m), 7.25-7.14 (5H, m), 7.02-6.99 (1H, m), 6.84-6.88 (3H, m), 6.36 (1H, s), 5.21 (2H, s), 2.49 (3H, s), 2.27 (3H, s) ppm;

2-benzyl-6-methyl-3-phenyl-2H-isoquinolin-1-one; $^1$H-NMR (400 MHz, CDCl$_3$): δ 8.38 (1H, d, J=8.3 Hz), 7.40-7.25 (5H, m), 7.21-7.14 (5H, m), 6.91-6.87 (2H, m), 6.38 (1H, m), 5.23 (2H, s), 2.49 (3H, s) ppm;

2-(2,4-dimethylbenzyl)-6-methyl-3-(4-phenoxyphenyl)-2H-isoquinolin-1-one; $^1$H-NMR (400 MHz, CDCl$_3$): δ 8.37 (1H, d, J=8.3 Hz), 7.39-7.30 (4H, m), 7.17-7.09 (3H, m), 7.04-7.01 (2H, m), 6.90-6.82 (4H, m), 6.65 (1H, d, J=7.6 Hz), 6.41 (1H, s), 5.12 (2H, s), 2.50 (3H, s), 2.23 (3H, s), 1.99 (3H, s) ppm;

2-(2,4-dimethylbenzyl)-6-methyl-3-phenyl-2H-isoquinolin-1-one; $^1$H-NMR (400 MHz, CDCl$_3$): δ 8.37 (1H, d, J=8.1 Hz), 7.38-7.27 (5H, m), 7.18-7.15 (2H, m), 6.86-6.82 (2H, m), 6.66 (1H, d, J=8.1 Hz), 6.41 (1H, s), 5.08 (2H, s), 2.50 (3H, s), 2.23 (3H, s), 1.90 (3H, s) ppm;

6-methyl-2-(4-methyl-benzyl)-3-(4-phenoxyphenyl)-2H-isoquinolin-1-one; $^1$H-NMR (400 MHz, CDCl$_3$): δ 8.36 (1H, d, J=8.1 Hz), 7.41-7.27 (4H, m), 7.19-7.14 (3H, m), 7.08-7.04 (2H, m), 7.00-6.92 (4H, m), 6.84-6.80 (2H, m), 6.37 (1H, s), 5.21 (2H, s), 2.49 (3H, s), 2.26 (3H, s) ppm;

6-methyl-2-(4-methyl-benzyl)-3-m-tolyl-2H-isoquinolin-1-one; $^1$H-NMR (400 MHz, CDCl$_3$): δ 8.36 (1H, d, J=8.1 Hz), 7.33-7.29 (1H, m), 7.28-7.25 (1H, m), 7.24-7.20 (2H, m), 7.04-6.94 (4H, m), 6.82-6.78 (2H, m), 6.35 (1H, s), 5.16 (2H, s), 2.48 (3H, s), 2.29 (3H, s), 2.26 (3H, s) ppm;

6-methyl-2-(4-methyl-benzyl)-3-phenyl-2H-isoquinolin-1-one; $^1$H-NMR (400 MHz, CDCl$_3$): δ 8.37 (1H, d, J=8.3 Hz), 7.43-7.30 (4H, m), 7.29-7.25 (1H, m), 7.23-7.19 (2H, m), 6.99-6.94 (2H, m), 6.81-6.76 (2H, m), 6.37 (1H, s), 5.18 (2H, s), 2.49 (3H, s), 2.26 (3H, s) ppm;

7-chloro-2-(2,4-dimethylbenzyl)-3-(4-phenoxyphenyl)-2H-isoquinolin-1-one; $^1$H-NMR (400 MHz, CDCl$_3$): δ 8.45 (1H, d, J=2.0 Hz), 7.61 (1H, dd, J=8.3, 2.0 Hz), 7.47 (1H, d, J=8.3 Hz), 7.40-7.34 (2H, m), 7.18-7.09 (3H, m), 7.04-7.0 (2H, m), 6.91-6.83 (4H, m), 6.62 (1H, d, J=8.0 Hz), 6.45 (1H, s), 5.12 (2H, s), 2.24 (3H, s), 1.99 (3H, s) ppm;

7-chloro-2-(2,4-dimethylbenzyl)-3-phenyl-2H-isoquinolin-1-one; $^1$H-NMR (400 MHz, CDCl$_3$): δ 8.46 (1H, d, J=2.3 Hz), 7.61 (1H, dd, J=8.3, 2.3 Hz), 7.47 (1H, d, J=8.3 Hz), 7.40-7.35 (1H, m), 7.32-7.25 (2H, m), 7.18-7.14 (2H, m), 6.87-6.83 (1H, m), 6.63 (1H, d, J=8.0 Hz), 6.45 (1H, s), 5.08 (2H, s), 2.25 (3H, s), 1.90 (3H, s) ppm;

2-(4-methyl-benzyl)-3-phenyl-2H-isoquinolin-1-one; $^1$H-NMR (400 MHz, CDCl$_3$): δ 8.50-8.47 (1H, m), 7.68-7.63 (1H, m), 7.52-7.47 (2H, m), 7.43-7.32 (3H, m), 7.24-7.21 (2H, m), 6.97 (2H, d, J=8.0 Hz), 6.80 (2H, d, J=8.0 Hz), 6.44 (1H, s), 5.20 (2H, br s), 2.26 (3H, s) ppm;

2-benzyl-3-phenyl-2H-isoquinolin-1-one; $^1$H-NMR (400 MHz, CDCl$_3$): δ 8.51-8.48 (1H, m), 7.68-7.63 (1H, m), 7.54-7.48 (2H, m), 7.43-7.37 (1H, m), 7.36-7.30 (2H, m), 7.22-7.14 (5H, m), 6.92-6.88 (2H, m), 6.45 (1H, s), 5.25 (2H, br s) ppm;

2-benzyl-7-chloro-3-(4-phenoxyphenyl)-2H-isoquinolin-1-one; $^1$H-NMR (400 MHz, CDCl$_3$): δ 8.46 (1H, d, J=2.3 Hz), 7.60 (1H, dd, J=8.3, 2.3 Hz), 7.45 (1H, d, J=8.3 Hz), 7.41-7.36 (2H, m), 7.22-7.11 (6H, m), 7.08-7.04 (2H, m), 6.96-6.90 (4H, m), 6.43 (1H, s), 5.26 (2H, br s) ppm;

2-benzyl-6-chloro-3-(4-phenoxyphenyl)-2H-isoquinolin-1-one; $^1$H-NMR (400 MHz, CDCl$_3$): δ 8.41 (1H, d, J=8.6 Hz), 7.48 (1H, d, J=2.0 Hz), 7.44 (1H, dd, J=8.6, 2.0 Hz), 7.41-7.36 (2H, m), 7.22-7.16 (4H, m), 7.15-7.10 (2H, m), 7.08-7.04 (2H, m), 6.96-6.90 (4H, m), 6.36 (1 H, s), 5.25 (2H, br s) ppm;

6-chloro-2-(2,4-dimethylbenzyl)-3-(4-phenoxyphenyl)-2H-isoquinolin-1-one; $^1$H-NMR (400 MHz, CDCl$_3$): δ 8.41

(1H, d, J=8.6 Hz), 7.50 (1H, d, J=2.0 Hz), 7.44 (1H, dd, J=8.6, 2.0 Hz), 7.40-7.35 (2H, m), 7.18-7.13 (1H, m), 7.13-7.09 (2H, m), 7.05-7.00 (2H, m), 6.91-6.83 (4H, m), 6.63 (1H, d, J=7.8 Hz), 6.40 (1H, s), 5.10 (2H, br s), 2.24 (3H, s), 1.99 (3H, s) ppm;

2-benzyl-6,8-dimethyl-3-(4-phenoxyphenyl)-2H-isoquinolin-1-one; $^1$H-NMR (400 MHz, CDCl$_3$): δ 7.40-7.35 (2H, m), 7.22-7.03 (10H, m), 6.95-6.89 (4H, m), 6.31 (1H, s), 5.21 (2H, br s), 2.92 (3H, s), 2.42 (3H, s) ppm;

2-(2,4-dimethylbenzyl)-6,8-dimethyl-3-(4-phenoxyphenyl)-2H-isoquinolin-1-one; $^1$H-NMR (400 MHz, CDCl$_3$): δ 7.38-7.33 (2H, m), 7.17-7.07 (5H, m), 7.03-7.00 (2H, m), 6.89-6.83 (4H, m), 6.66 (1H, d, J=8.3 Hz), 6.35 (1H, s), 5.05 (2H, br s), 2.92 (3H, s), 2.43 (3H, s), 2.24 (3H, s), 2.00 (3H, s) ppm;

3-(4-benzylphenyl)-2-(2,4-dimethylbenzyl)-8-methyl-2H-isoquinolin-1-one; $^1$H-NMR (400 MHz, CDCl$_3$): δ 7.48 (1H, t, J=7.3 Hz), 7.34-7.20 (3H, m), 7.18-7.15 (2H, m), 7.09 (4H, s), 6.85-6.82 (2H, m), 6.66 (1 H, d, J=8.3 Hz), 6.39 (1H, s), 5.03 (2H, br s), 3.97 (2H, s), 2.95 (3H, s), 2.24 (3H, s), 1.92 (3H, s) ppm;

2-benzyl-5-methyl-3-(4-phenoxyphenyl)-2H-isoquinolin-1-one; $^1$H-NMR (400 MHz, CDCl$_3$): δ 8.37 (1H, d, J=7.6 Hz), 7.53-7.47 (1H, m), 7.43-7.35 (3H, m), 7.22-7.11 (6H, m), 7.10-7.02 (2H, m), 6.98-6.89 (4H, m), 6.55 (1H, s), 5.28 (2H, S), 2.51 (3H, s) ppm;

2-benzyl-5,6,7,8-tetramethyl-3-(4-phenoxyphenyl)-2H-isoquinolin-1-one; $^1$H-NMR (400 MHz, CDCl$_3$): δ 7.40-7.35 (2H, m), 7.21-7.11 (6H, m), 7.07-7.03 (2H, m), 6.96-6.90 (4H, m), 6.56 (1 H, s), 5.22 (2H, s), 2.93 (3H, s), 2.42 (3H, s), 2.40 (3H, s), 2.38 (3H, s) ppm;

2-(2,4-dimethylbenzyl)-5-methyl-3-(4-phenoxyphenyl)-2H-isoquinolin-1-one; $^1$H-NMR (400 MHz, CDCl$_3$): δ 8.37 (1H, d, J=7.8 Hz), 7.53-7.49 (1H, m), 7.43-7.34 (3H, m), 7.18-7.11 (3H, m), 7.05-7.01 (2H, m), 6.93-6.82 (4H, m), 6.66 (1H, d, J=7.3 Hz), 6.57 (1H, s), 5.13 (2H, br s), 2.53 (3H, s), 2.24 (3H, s), 1.99 (3H, s) ppm;

2-benzyl-8-methoxy-3-(4-phenoxyphenyl)-2H-isoquinolin-1-one; $^1$H-NMR (400 MHz, CDCl$_3$): δ 7.55 (1H, t, J=8.1), 7.40-7.35 (2H, m), 7.20-6.89 (14H, m), 6.34 (1H, s), 5.23 (2H, s), 4.02 (3H, s) ppm;

2-(2,4-dimethylbenzyl)-8-fluoro-3-(4-phenoxyphenyl)-2H-isoquinolin-1-one; $^1$H-NMR (400 MHz, CDCl$_3$): δ 7.62-7.55 (1H, m), 7.40-7.34 (2H, m), 7.30-7.25 (1H, m), 7.19-7.09 (4H, m), 7.05-7.00 (2H, m), 6.92-6.84 (4H, m), 6.72-6.68 (1H, m), 6.43 (1H, d, J=2.0 Hz), 5.09 (2H, br s), 2.24 (3H, s), 1.99 (3H, s) ppm;

8-chloro-2-(2,4-dichloro-benzyl)-3-(4-phenoxyphenyl)-2H-isoquinolin-1-one; $^1$H-NMR (400 MHz, CDCl$_3$): δ 7.53 (1H, d, J=2.3 Hz), 7.52 (1H, s), 7.44-7.35 (3H, m), 7.29 (1H, d, J=2.3), 7.19-7.12 (2H, m), 7.11-7.02 (4H, m), 6.94-6.87 (3H, m), 6.45 (1H, s), 5.19 (2H, s) ppm;

2-benzyl-8-fluoro-3-(4-phenoxyphenyl)-2H-isoquinolin-1-one; $^1$H-NMR (400 MHz, CDCl$_3$): δ 7.61-7.54 (1H, m), 7.42-7.36 (2H, m), 7.28-7.23 (1H, m), 7.22-7.10 (7H, m), 7.10-7.04 (2H, m), 6.98-6.92 (4H, m), 6.40 (1H, d, J=2.3 Hz), 5.24 (2H, br s) ppm;

2-(2,4-dimethylbenzyl)-3-(4-phenoxyphenyl)-8-trifluoromethyl-2H-isoquinolin-1-one; $^1$H-NMR (400 MHz, CDCl$_3$): δ 7.95-7.90 1H, m), 7.72-7.70 (2H, m), 7.40-7.35 (2H, m), 7.18-7.13 (1H, m), 7.13-7.09 (2H, m), 7.04-7.00 (2H, m), 6.91-6.83 (3H, m), 6.62 (1H, d J=8.6 Hz), 6.48 (1H, s), 5.14 (2H, br s), 2.24 (3H, s), 1.96 (3H, s) ppm;

2-(2,4-dimethylbenzyl)-8-methoxy-3-(4-phenoxyphenyl)-2H-isoquinolin-1-one; $^1$H-NMR (400 MHz, CDCl$_3$): δ 7.56 (1H, t, J=7.8 Hz), 7.39-7.34 (2H, m), 7.17-7.11 (3H, m), 7.07-7.00 (3H, m), 6.93-6.82 (5H, m), 6.72 (1H, d, J=9.0 Hz), 6.37 (1H, s), 5.07 (2H, s), 4.00 (3H, s), 2.23 (3H, s), 1.98 (3H, s) ppm;

8-chloro-2-(2,4-difluorobenzyl)-3-(4-phenoxyphenyl)-2H-isoquinolin-1-one; $^1$H-NMR (400 MHz, CDCl$_3$): δ 7.52-7.50 (2H, m), 7.41-7.36 (3H, m), 7.19-7.14 (1H, m), 7.13-7.10 (2H, m), 7.09-7.03 (3H, m), 6.97-6.93 (2H, m), 6.79-6.73 (1H, m), 6.69-6.63 (1H, m), 6.41 (1H, s), 5.20 (2H, s) ppm;

7,8-dichloro-2-(2,4-dimethylbenzyl)-3-(4-phenoxyphenyl)-2H-isoquinolin-1-one; $^1$H-NMR (400 MHz, CDCl$_3$): δ 7.69 (1H, d, J=8.6 Hz), 7.40-7.33 (3H, m), 7.18-7.10 (3H, m), 7.04-7.00 (2H, m), 6.91-6.84 (4H, m), 6.65 (1H, d, J=8.0 Hz), 6.39 (1H, s), 5.30 (2H, s), 2.24 (3H, s), 2.00 (3H, s), 1.54 (3H, s) ppm;

8-chloro-2-(2,4-difluorobenzyl)-5-methyl-3-(4-phenoxyphenyl)-2H-isoquinolin-1-one; $^1$H-NMR (400 MHz, CDCl$_3$): δ 7.43-7.35 (4H, m), 7.20-7.10 (3H, m), 7.09-7.01 (3H, m), 6.98-6.94 (2H, m), 6.79-6.72 (1H, s), 6.69-6.62 (1H, m), 6.48 (1H, s), 5.21 (2H, s), 2.46 (3H, s) ppm;

6,7-dichloro-2-(2,4-difluorobenzyl)-3-(4-phenoxyphenyl)-2H-isoquinolin-1-one; $^1$H-NMR (400 MHz, CDCl$_3$): δ 8.53 (1H, s), 7.61 (1H, s), 7.42-7.36 (2H, m), 7.22-7.15 (1H, m), 7.13-7.04 (4H, m), 7.00-6.94 (3H, m), 6.78-6.72 (1H, m), 6.70-6.64 (1H, m), 6.34 (1H, s), 5.21 (2H, s) ppm;

8-chloro-2-(2-chloro-4-fluoro-benzyl)-3-(4-phenoxyphenyl)-2H-isoquinolin-1-one; $^1$H-NMR (400 MHz, CDCl$_3$): δ 7.53 (1H, d, J=1.8 Hz), 7.52 (1H, s), 7.43-7.35 (3H, m), 7.19-7.14 (1H, m), 7.10-7.00 (5H, m), 6.95-6.86 (4H, m), 6.44 (1H, s), 5.20 (2H, s) ppm; and 5,6-dichloro-2-(2,4-difluorobenzyl)-3-(4-phenoxyphenyl)-2H-isoquinolin-1-one; $^1$H-NMR (400 MHz, CDCl$_3$): δ 8.32 (1H, d, J=8.6 Hz), 7.56 (1H, d, J=8.6 Hz), 7.42-7.37 (2H, m), 7.22-7.13 (3H, m), 7.09-7.05 (2H, m), 7.01-6.94 (3H, m), 6.84 (1H, s), 6.79-6.72 (1H, m), 6.71-6.65 (1H, m), 5.23 (2H, s) ppm.

C. In a similar manner, other compounds of formula (Ia) are prepared.

EXAMPLE 3

Compounds of Formula (Ib)

A. A 1.53 M solution of n-butyllithium (2.61 mL, 4 mmol) in hexane was added to a solution of diisopropylamine (0.55 mL, 4 mmol) in THF (5 mL) at 0° C. under nitrogen. After 15 minutes, a solution of N-methyl-2-methylbenzamide (149 mg, 1 mmol) in THF (3 mL) was added to the mixture. After another 45 minutes, a solution of 4-(2,2,2-trifluoro-1-hydroxy-1-trifluoromethylethyl)benzoic acid methyl ester (302 mg, 1 mmol) in THF (3 mL) was added to the reaction mixture. The mixture was stirred for 2 hours. Then the solution was stirred at reflux for 45 minutes with 3N HCl aq. (3 mL). The solution was poured into water. The product was extracted with ethyl acetate, washed with water and brine, and dried over Na$_2$SO$_4$. After concentration, the residue was purified by chromatography on silica gel (hexane:ethyl acetate=4:1 to 2:1), to provide 235 mg of solid in 58% yield. The powder was recrystallized from ethyl acetate/hexane to give 153 mg of 2-methyl-3-[4-(2,2,2-trifluoro-1-hydroxy-1-trifluoromethylethyl)phenyl]-2H-isoquinolin-1-one as colorless prisms: mp 265-266° C.; IR (KBr): V$_{max}$ 3207, 1642, 1619, 1594, 1268, 1188, 967 cm$^{-1}$; $^1$H-NMR (400 MHz, CDCl$_3$): δ 8.46 (1H, d, J=8.0 Hz), 7.86 (2H, d, J=8.0 Hz), 7.64 (1H, t, J=8.8 Hz), 7.54-7.50 (4H, m), 6.50 (1H, s), 3.77 (1H, s), 3.44 (3H, s) ppm; FABMS (m/z): 402 ([M+H]$^+$); FABHRMS (m/z): Calcd. for C$_{19}$H$_{13}$F$_6$NO$_2$ ([M+H]+): 402.0928. Found: 402.0942. Anal. calcd. for $C_{19}H_{13}F_6NO_2$: C, 56.87; H, 3.27; N, 3.49. Found: C, 56.81; H, 3.17; N, 3.51.

B. In a similar manner, other compounds of formula (Ib) are prepared.

EXAMPLE 4

Compounds of Formula (Ib)

A. A 1.53 M solution of n-butyllithium (2.61 mL, 4 mmol) in hexane was added to a solution of diisopropylamine (0.55 mL, 4 mmol) in THF (5 mL) at 0° C. under nitrogen. After 15 minutes, a solution of N-(4-methylbenzyl)-2-methylbenzamide (239 mg, 1 mmol) in THF (3 mL) was added to the mixture. After another 45 minutes, a solution of 4-(2,2,2-trifluoro-1-hydroxy-1-trifluoromethylethyl)benzoic acid methyl ester (302 mg, 1 mmol) in THF (3 mL) was added to the reaction mixture. The mixture was stirred for 2 hours. Then the solution was stirred at reflux for 45 minutes with 3N HCl aq. (4 mL). The solution was poured into water. The product was extracted with ethyl acetate, washed with water and brine, and dried over $Na_2SO_4$. After concentration, the residue was purified by chromatography on silica gel (hexane/ethyl acetate=4:1) and HPLC, to provide 154 mg of solid in 27% yield. The powder was recrystallized from ethyl acetate/hexane to give 134 mg of 2-(4-methylbenzyl)-3-[4-(2,2,2-trifluoro-1-hydroxy-1-trifluoromethylethyl)phenyl]-2H-isoquinolin-1-one as colorless prisms; mp 267-268° C.; IR (KBr): $v_{max}$ 3198, 1645, 1619, 1590, 1267, 1214, 1174, 933 cm$^{-1}$; $^1$H-NMR (400 MHz, CDCl$_3$): δ 8.50 (1H, d, J=8.8 Hz), 7.69 (2H, d, J=8.4 Hz), 7.66 (1H, m), 7.55-7.50 (2H, m), 7.26 (2H, d, J=8.4 Hz), 6.92 (2H, d, J=8.0 Hz), 6.67 (2H, d, J=8.0 Hz), 6.46 (1H, s), 5.12 (2H, s), 4.20 (1H, s), 2.25 (3H, s) ppm; FABMS (m/z): 492 ([M+H]+); FAB-HRMS (m/z): Calcd. for $C_{26}H_{19}F_6NNaO_2$ ([M+Na]+): 514.1218. Found: 514.1211. Anal. calcd. for $C_{26}H_{19}F_6NO_2$: C, 63.55; H, 3.90; N, 2.85. Found: C, 63.55; H, 3.95; N, 2.85.

B. In a similar manner, other compounds of formula (Ib) are prepared.

EXAMPLE 5

Compounds of Formula (Ib)

A. To a solution of diisopropylamine (0.2 mL, 1.43 mmol) in THF (3 mL) at 0° C. was added n-butyllithium (0.9 mL of a 1.6 M solution in hexane, 1.44 mmol). After stirring at 0° C. for 10 minutes, the resulting lithium diisopropylamide solution was treated with a solution of N-benzyl-2-methylbenzamide (145 mg, 0.64 mmol) in THF (2 mL). The resulting deep purple solution was stirred at 0° C. for 75 minutes at which time it was treated with a solution of N-methoxy-N-methyl-benzamide (117 mg, 0.71 mmol) in THF (2 mL). After slowly warming to ambient temperature over 100 minutes the reaction was quenched by the addition of 3N HCl (12 mL). The biphasic mixture was then heated to reflux with vigorous stirring. After 1 hour at reflux the reaction mixture was allowed to cool to ambient temperature. After cooling, the reaction was diluted with ether (50 mL), and basified by careful addition of solid $Na_2CO_3$. The basic aqueous was extracted with ether (3×20 mL), combined organics were washed with brine (20 mL), dried over $Na_2SO_4$, filtered, and concentrated under educed pressure to afford a pale orange oil. The crude product was purified by silica gel column chromatography eluting with a gradient from 0% to 20% ethyl acetate/hexane on a 20 g silica column. The product peak was collected to afford 2-benzyl-3-phenyl-2H-isoquinolin-1-one (22 mg, 11% yield) as a clear oil that slowly solidified to a white waxy solid. $^1$H-NMR (400 MHz, CDCl$_3$): δ 8.49 (1H, d J=8.3 Hz), 7.68-7.63 (1H, m), 7.53-7.48 (2H, m), 7.42-7.37 (1H, m), 7.35-7.30 (2H, m), 7.22-7.14 (5H, m), 6.92-6.88 (2H, m), 6.45 (1H, s), 5.25 (2H, s) ppm.

B. In a similar manner, other compounds of formula (Ib) are prepared:

EXAMPLE 6

Compounds of Formula (Ic)

A. To a solution of trifluoromethanesulfonic acid 2-(2,4-dimethylbenzyl)-1-oxo-1,2-dihydro-isoquinolin-3-yl ester (50 mg, 0.12 mmol) in THF (1.5 mL) was added Et$_3$N (83 μL, 0.59 mmol). The resulting mixture was then degassed by bubbling argon through the solution for twenty minutes. The degassed solution was then treated with 2-methyl-but-3-yn-2-ol (23 μL, 0.24 mmol) followed by tetrakistriphenylphosphine Pd(0) (13 mg, 12 μmol) and CuI (~2 mg, ~12 μmol). The resulting suspension was stirred at ambient temperature for 16 hours, then filtered through a short plug of silica gel eluting with ethyl acetate. The filtrate was concentrated under reduced pressure to afford the crude product. The crude product was purified by silica gel column chromatography eluting with a gradient from 0% to 50% ethyl acetate/hexane on a silica column. The product peak was collected to afford 2-(2,4-dimethylbenzyl)-3-(3-hydroxy-3-methylbut-1-ynyl)-2H-isoquinolin-1-one (27 mg, 65% yield) as a white solid. $^1$H-NMR (400 MHz, CDCl$_3$): δ 8.43 (1H, d, J=8.1 Hz), 7.70-7.64 (1H, m), 7.75-7.49 (2H, m), 7.0 (1H, s), 6.89-6.85 (2H, m), 6.65-6.61 (1H, m), 5.42 (2H, s), 2.40 (3H, s), 2.26 (3H, s), 1.40 (6H, s). ppm.

B. In a similar manner, the following compounds of formula (Ic) were prepared:

2-biphenyl-4-ylmethyl-3-trimethylsilanylethynyl-2H-isoquinolin-1-one; $^1$H-NMR (400 MHz, CDCl$_3$): δ 8.43 (1H, d, J=8.1 Hz), 7.64 (1H, ddd, J=7.6, 7.6, 1.0 Hz), 7.57-7.46 (8H, m), 7.44-7.38 (2H, m), 7.32 (1H, m), 6.91 (1H, s), 5.55 (2H, s), 0.25 (9H, s) ppm;

2-(2,4-dimethylbenzyl)-3-(3-hydroxy-3-methylbut-1-ynyl)-2H-isoquinolin-1-one; $^1$H-NMR (400 MHz, CDCl$_3$): δ 8.43 (1H, d, J=8.3 Hz), 7.66 (1H, ddd, J=7.3, 7.3, 1.3 Hz), 7.55-7.48 (2H, m), 7.00 (1H, s), 6.90-6.84 (2H, m), 6.63 (1 H, d, J=7.8 Hz), 5.42 (2H, s), 2.40 (3H, s), 2.26 (3H, s), 1.69 (1H, s), 1.40 (6H, s) ppm;

2-benzyl-3-(3-hydroxy-3-methylbut-1-ynyl)-2H-isoquinolin-1-one; $^1$H-NMR (400 MHz, CDCl$_3$): δ 8.43 (1H, d, J=8.1 Hz), 7.65 (1H, ddd, J=7.6, 7.6, 1.3 Hz), 7.54-7.45 (2H, m), 7.20-7.37 (5H, m), 6.83 (1H, s), 5.51 (2H, s), 1.57-1.51 (6H, m) ppm;

3-(3-hydroxy-3-methylbut-1-ynyl)-2-(4-methylbenzyl)-2H-isoquinolin-1-one; $^1$H-NMR (400 MHz, CDCl$_3$): δ 8.50-8.37 (1H, m), 7.70-7.60 (2H, m), 7.55-7.43 (3H, m), 7.18-7.08 (2H, m), 6.85-6.79 (1H, m), 5.55-5.40 (2H, m), 2.40-2.25 (3H, m), 1.80-1.46 (6H, m) ppm;

2-benzyl-3-trimethylsilanylethynyl-2H-isoquinolin-1-one; $^1$H-NMR (400 MHz, CDCl$_3$): δ 8.19 (1H, d, J=8.1 Hz), 7.54-7.43 (1H, m), 7.40 (1H, ddd, J=7.6, 7.6,1 Hz), 7.30-7.22 (2H, m), 7.20-7.11 (2H, m), 7.90-6.97 (2H, m), 6.66 (1H, s), 5.29 (2H, s), 0.00 (9H, s) ppm;

2-(4-methylbenzyl)-3-trimethylsilanylethynyl-2H-isoquinolin-1-one; $^1$H-NMR (400 MHz, CDCl$_3$): δ 8.41 (1H, d, J=8.6 Hz), 7.62 (1H, ddd, J=7.3, 7.3, 1.5 Hz), 7.55-7.43 (2H, m), 7.40-7.31 (2H, m), 7.09 (2H, d, J=7.9 Hz), 6.88 (1H, s), 5.47 (2H, s), 2.30 (3H, s), 0.25 (9H, s) ppm;

2-(2,4-dimethylbenzyl)-3-phenylethynyl-2H-isoquinolin-1-one; $^1$H-NMR (400 MHz, CDCl$_3$): δ 8.45 (1H, d, J=7.8 Hz), 7.67 (1 H, ddd, J=7.6, 7.6, 1.3 Hz), 7.56-7.48 (2H, m), 7.36-7.27 (5H, m), 7.04-6.97 (2H, m), 6.88 (1H, d, J=7.83 Hz), 6.74 (1H, d, J=7.8 Hz), 5.53 (2H, s), 2.42 (3H, s), 2.26 (3H, s) ppm; and 2-(2,4-dimethylbenzyl)-3-(1-hydroxycyclohexylethynyl)-2H-isoquinolin-1-one; $^1$H-NMR (400 MHz, CDCl$_3$): δ 8.42 (1H, d, J=8.1 Hz), 7.66 (1H, ddd, J=7.6, 7.6, 1.3 Hz), 7.54-7.48 (2H, m), 6.98 (1H, s), 6.89-6.83 (2H, m), 6.60 (1H, d, J=7.8 Hz), 5.43 (2H, s), 2.39 (3H, s), 2.25 (3H, s), 1.85-1.73 (3H, m), 1.63-1.10 (7H, m), 0.91-0.85 (1H, m) ppm.

EXAMPLE 7

Compounds of Formula (W) and (Id)

A. A suspension of 3-(4-benzyloxyphenyl)-8-chloro-isochromen-1-one (1.7 g, 4.7 mmol) and 2,4-difluorobenzylamine (0.75 mL, 6.3 mmol) was prepared in toluene (25 mL) in a 100 mL round-bottomed flask under nitrogen. To the resulting suspension was added a solution of methyl aluminoxane (5.0 mL, of a 1.5 M solution in toluene, 7.5 mmol). Gas evolution was observed as the aluminoxane solution was added. The resulting suspension was then heated to reflux. As the solution came to reflux the solids dissolved to afford a brown solution. After stirring at reflux for 16 hours, an aliquot of the reaction was worked up with aqueous HCl, and analyzed by TLC. There was no visible 8-chloro-3-(4-phenoxyphenyl)-isochromen-1-one, and there were two product spots visible. Heating was discontinued and the reaction was allowed to cool to ambient temperature. The reaction was then quenched by the addition of 1N HCl (aq.) (50 mL), and diluted with EtOAc (100 mL). The layers were separated and the acidic aqueous layer was extracted with EtOAc (3×30 mL). The combined organic layers were washed with H$_2$O (50 mL), saturated aqueous NaHCO$_3$ (30 mL), then brine. The organic layer was dried over Na$_2$SO$_4$, filtered, and concentrated under reduced pressure to afford a white foam. The crude foam was purified by silica gel column chromatography eluting with a gradient from 0% to 30% EtOAc/hexane. Two product peaks were collected from the column: The first peak that eluted was concentrated to afford 3-(4-benzyloxyphenyl)-8-chloro-2-(2,4-difluorobenzyl)-2H-isoquinolin-1-one, a compound of formula (Id), (1.68 g, 73% yield); $^1$H-NMR (400 MHz, CDCl$_3$): δ 7.51-7.48 (2H, m), 7.46-7.33 (6H, m), 7.11-7.07 (2H, m), 7.04-6.96 (1H, m), 6.95-6.91 (2H, m), 6.78-6.71 (1H, m), 6.66-6.59 (1H, m), 6.39 (1H, s), 5.17 (2H, s), 5.10 (2H, s); and the second peak that eluted was concentrated to afford 2-[2-(4-benzyloxyphenyl)-2-oxoethyl]-6-chloro-N-(2,4-difluorobenzyl)benzamide, a compound of formula (W) (533 mg, 22% yield); $^1$H-NMR (400 MHz, CDCl$_3$): δ 7.78 (2H, d, J=8.8 Hz), 7.45-7.30 (5H, m), 7.26-7.14 (3H, m), 7.00-6.93 (3H, m), 6.71 (1H, t, J=6.3 Hz), 6.56-6.49 (1H, m), 6.45-6.37 (1H, m), 5.12 (2H, s), 4.40 (2H, d, J=6.3 Hz), 4.16 (2H, s).

B. Alternatively, 8-chloro-3-(4-phenoxyphenyl)isochromen-1-one (48 mg, 0.14 mmol) and 2,4-difluorobenzylamine (24 µL, 0.20 mmol) were combined in toluene (2.0 mL) in a round-bottomed flask under nitrogen. To the resulting mixture was added a solution of methyl aluminoxane (0.11 mL, of a 1.5 M solution in toluene, 0.16 mmol). The resulting yellow solution was then heated to reflux. TLC of the reaction mixture after 1 hour at reflux showed no 8-chloro-3-(4-phenoxyphenyl)isochromen-1-one remaining. Heating was discontinued and the reaction was allowed to cool to ambient temperature. The reaction was then quenched by the addition of 1N HCl (aq.) (5 mL), and diluted with EtOAc (25 mL). The layers were separated and the acidic aqueous layer was extracted with EtOAc (3×10 mL). The combined organic layers were washed with H$_2$O (10 mL), saturated aqueous NaHCO$_3$ (10 mL), then brine. The organic layer was dried over Na$_2$SO$_4$, filtered, and concentrated under reduced pressure to afford a white solid. The crude solid was purified by silica gel column chromatography by adsorbing the material onto silica gel from a CH$_2$Cl$_2$ solution, loading the resulting solid onto the column and eluting with a gradient from 0% to 20% EtOAc/hexane. The main peak that eluted was collected to afford a compound of formula (W), 2-chloro-N-(2,4-difluorobenzyl)-6-[2-oxo-2-(4-phenoxyphenyl)ethyl]benzamide, (54 mg, 79% yield) as a white solid; $^1$H-NMR (400 MHz, CDCl$_3$): δ 7.87-7.82 (2H, m), 7.46-7.41 (2H, m), 7.35-7.21 (4H, m), 7.14-7.10 (2H, m), 7.05-7.02 (1H, m), 7.01-6.96 (2H, m), 6.66-6.60 (1H, m), 6.53-6.47 (1H, m), 6.43 (1H, t, J=6.1 Hz), 4.49 (2H, d, J=6.1 Hz), 4.25 (2H, s); which could be used in the next step to produce a corresponding compound of formula (Id).

C. To a solution of 2-[2-(4-bromofuran-2-yl)-2-oxoethyl]-6-chloro-N-(2,4-difluorobenzyl)benzamide (2.4 g, 5.1 mmol), prepared in a manner similar to that described above in Paragraph B, in dioxane (30 mL) was added 4-toluenesulfonic acid monohydrate (450 mg, 2.4 mmol). The resulting solution was heated to reflux. After 20 hours at reflux the reaction solution was allowed to cool to ambient temperature, and treated with Et$_3$N (2.0 mL, 14 mmol). The crude product was purified by adsorbing the material onto silica gel from the reaction solution, loading the resulting solid onto the column and eluting with a gradient from 10% to 50% EtOAc in hexane containing 10% CH$_2$Cl$_2$ (to improve the solubility of the product). The broad peak that eluted was collected to afford 3-(4-bromofuran-2-yl)-8-chloro-2-(2,4-difluorobenzyl)-2H-isoquinolin-1-one (1.9 g, 82% yield) as a brown powder. $^1$H-NMR (400 MHz, CDCl$_3$): δ 7.56-7.51 (2H, m), 7.47 (1H, d, J=0.8 Hz), 7.43 (1H, dd, J=6.3, 2.8 Hz), 7.06-6.99 (1H, m), 6.79-6.73 (2H, m), 6.68 (1H, s), 6.49 (1H, d, J=0.8 Hz), 5.32 (2H, s).

D. In a similar manner as described above in Paragraphs B and C, the following compounds of formula (Id) were prepared:

3-(5-bromothiophen-2-yl)-8-chloro-2-(2,4-difluorobenzyl)-2H-isoquinolin-1-one; $^1$H-NMR (400 MHz, CDCl$_3$): δ 7.55-7.52 (2H, m), 7.43-7.39 (1H, m), 7.01-6.94 (2H, m), 6.82-6.72 (2H, m), 6.69 (1H, d, J=4.0 Hz), 6.59 (1H, s), 5.28 (2H, s) ppm;

2-{4-[8-chloro-2-(2,4-difluorobenzyl)-1-oxo-1,2-dihydro-isoquinolin-3-yl]-phenoxy}nicotinonitrile; $^1$H-NMR (400 MHz, CDCl$_3$): δ 8.35 (1H, dd, J=5.0, 2.0 Hz), 8.05 (1H, dd, J=7.8, 2.0 Hz), 7.54-7.51 (2H, m), 7.42-7.38 (1H, m), 7.27-7.24 (2H, m), 7.22-7.18 (2H, m), 7.15 (1H, dd, J=7.8, 5.0 Hz), 7.08-7.00 (1H, m), 6.80-6.74 (1H, m), 6.71-6.65 (1H, m), 6.46 (1H, s), 5.22 (2H, br s) ppm;

8-chloro-2-(2,4-difluorobenzyl)-3-(4-hydroxyphenyl)-2H-isoquinolin-1-one; $^1$H-NMR (400 MHz, CDCl$_3$): δ 9.81 (1H, s), 7.66-7.63 (2H, m), 7.54-7.51 (1H, m), 7.17-7.11 (3H, m), 6.98-6.93 (2H, m), 6.79-6.75 (2H, m), 6.59 (1H, s), 5.08 (2H, m) ppm;

8-chloro-2-(2,4-difluorobenzyl)-3-[4-(pyrazin-2-yloxy)phenyl]-2H-isoquinolin-1-one; $^1$H-NMR (400 MHz, CDCl$_3$): δ 8.47 (1H, d, J=1.3 Hz), 8.33 (1H, d, J=2.5 Hz), 8.15-8.13 (1H, m), 7.55-7.49 (2H, m), 7.42-7.37 (1H, m), 7.25-7.15 (4H, m), 7.09-7.02 (1H, m), 6.80-6.74 (1H, m), 6.70-6.64 (1H, m), 6.45 (1H, s), 5.22 (2H, s) ppm;

2-{4-[2-(2,4-difluorobenzyl)-7-fluoro-1-oxo-1,2-dihydro-isoquinolin-3-yl]-phenoxy}nicotinonitrile; $^1$H-NMR (400 MHz, CDCl$_3$): δ 8.35 (1H, dd, J=5.0, 2.0 Hz), 8.12 (1H, dd, J=9.4, 2.8 Hz), 8.03 (1H, dd, J=7.6, 2.0 Hz), 7.54 (1H, dd, J=8.6, 5.0 Hz), 7.43 (1H, td, J=8.5, 2.8 Hz), 7.27-7.14 (5H, m), 7.01-6.94 (1H, m), 6.78-6.72 (1H, m), 6.72-6.65 (1H, m), 6.52 (1H, s), 5.25 (2H, s) ppm;

2-(2,4-difluorobenzyl)-7-fluoro-3-[4-(pyrazin-2-yloxy)phenyl]-2H-isoquinolin-1-one; $^1$H-NMR (400 MHz, CDCl$_3$): δ 8.48 (1H, d, J=1.5 Hz), 8.33 (1H, d, J=2.5 Hz), 8.16-8.14(1H, dd, J=2.8, 1.5 Hz), 8.12 (1H, dd, J=9.4, 2.8 Hz), 7.53 (1H, dd, J=8.8, 5.0 Hz), 7.43 (1H, td, J=8.3, 2.8 Hz), 7.26-7.15 (4H, m), 7.02-6.95 (1H, m), 6.78-6.73 (1H, m), 6.71-6.64 (1H, m), 6.51 (1H, s), 5.25 (2H, s) ppm;

2-(2,4-difluorobenzyl)-7-fluoro-3-(4-phenoxyphenyl)-2H-isoquinolin-1-one; $^1$H-NMR (400 MHz, CDCl$_3$): δ 8.11 (1H, dd, J=9.4, 2.8 Hz), 7.52 (1H, dd, J=8.6, 5.1 Hz), 7.45-7.36 (3H, m), 7.19-7.14 (1H, m), 7.14-7.09 (2H, m), 7.08-7.03 (2H, m), 7.02-6.93 (3H, m), 6.78-6.72 (1H, m), 6.70-6.64 (1H, m), 6.47 (1H, s), 5.24 (2H, s) ppm;

2-(2,4-difluorobenzyl)-5-fluoro-3-[4-(pyrazin-2-yloxy)phenyl]-2H-isoquinolin-1-one; $^1$H-NMR (400 MHz, CDCl$_3$): δ 8.48 (1H, d, J=1.3 Hz), 8.33 (1H, d, J=2.8 Hz), 8.26 (1H, d, J=8.1 Hz), 8.15 (1H, dd, J=2.8, 1.5 Hz), 7.50-7.43 (1H, m), 7.42-7.34 (1H, m), 7.27-7.24 (2H, m), 7.20-7.16 (2H, m), 7.05-6.96 (1H, m), 6.79 6.65 (3H, m), 5.26 (2H, s) ppm;

2-{4-[2-(2,4-difluorobenzyl)-5-fluoro-1-oxo-1,2-dihydro-isoquinolin-3-yl]-phenoxy}nicotinonitrile; $^1$H-NMR (400 MHz, CDCl$_3$): δ 8.35 (1H, d, J=4.8 Hz), 8.26 (1H, d, J=8.1 Hz), 8.05 (1H, d, J=7.6 Hz), 7.50-7.43 (1H, m), 7.42-7.34 (1H, m), 7.30-7.25 (2H, m), 7.24-7.19 (2H, m), 7.16 (1H, m), 6.98 (1H, q, J=7.6 Hz), 6.79-6.66 (3H, m), 5.26 (2H, s) ppm;

8-chloro-2-cyclohexylmethyl-3-(4-phenoxyphenyl)-2H-isoquinolin-1-one; $^1$H-NMR (400 MHz, CDCl$_3$): δ 7.48-7.44 (2H, m), 7.43-7.37 (2H, m), 7.36-7.29 (3H, m), 7.21-7.15 (1H, m), 7.11-7.05 (4H, m), 6.32 (1H, s), 3.90 (2H, br s), 1.81-1.68 (1H, m), 1.62-1.52 (2H, m), 1.50-1.43 (2H, m), 1.15-0.98 (3H, m), 0.77-0.65 (2H, m) ppm;

8-chloro-2-(2,2-dimethyl-propyl)-3-(4-phenoxyphenyl)-2H-isoquinolin-1-one; $^1$H-NMR (400 MHz, CDCl$_3$): δ 7.48-7.43 (1H, m), 7.42-7.37 (2H, m), 7.36-7.31 (3H, m), 7.20-7.15 (1H, m), 7.10-7.03 (4H, m), 6.30 (1H, s), 4.9-3.3 (2H, broad hump), 1.55 (9H, s) ppm;

8-chloro-3-(4-phenoxyphenyl)-2-pyridin-3-ylmethyl-2H-isoquinolin-1-one-trifluoroacetic acid salt; $^1$H-NMR (400 MHz, CDCl$_3$): δ 8.67 (1H, d, J=5.6 Hz), 8.33 (1H, s), 8.06 (1H, d, J=8.1 Hz), 7.64 (1H, dd, J=8.1, 5.6 Hz), 7.57-7.52 (2H, m), 7.44-7.38 (3H, m), 7.23-7.18 (3H, m), 7.12-7.08 (2H, m), 7.04-6.99 (2H, m), 6.48 (1H, s), 5.32 (2H, br s) ppm;

8-chloro-2-(5-methylfuran-2-ylmethyl)-3-(4-phenoxyphenyl)-2H-isoquinolin-1-one; $^1$H-NMR (400 MHz, CDCl$_3$): δ 7.47-7.44 (2H, m), 7.42-7.37 (2H, m), 7.36-7.32 (3H, m), 7.20-7.15 (1H, m), 7.11-7.07 (2H, m), 7.06-7.02 (2H, m), 6.36 (1H, s), 6.02 (1H, d, J=3.3 Hz), 5.82-5.80 (1H, m), 5.09 (2H, s), 2.17 (3H, s) ppm;

8-chloro-3-(4-phenoxyphenyl)-2-thiophen-2-ylmethyl-2H-isoquinolin-1-one; $^1$H-NMR (400 MHz, CDCl$_3$): δ 7.48-7.46 (2H, m), 7.43-7.38 (2H, m), 7.35-7.34 (1H, m), 7.30-7.27 (2H, m), 7.21-7.16 (1H, m), 7.14-7.08 (3H, m), 7.07-7.04 (2H, m), 6.82 (1H, dd, J=5.0, 3.5 Hz), 6.66 (1H dd, J=3.5, 1.0 Hz), 6.36 (1 H, s), 5.33 (2H, br s) ppm; and 2-(2,4-difluorobenzyl)-5-fluoro-3-(4-phenoxyphenyl)-2H-isoquinolin-1-one; $^1$H-NMR (400 MHz, CDCl$_3$): δ 8.25 (1H, d, J=8.1 Hz), 7.47-7.35 (4H, m), 7.19-7.12 (3H, m), 7.07-7.04 (2H, m), 7.03-6.94 (3H, m), 6.78-6.72 (1 H, m), 6.70-6.64 (2H, m), 5.24 (2H, s) ppm.

E. Trifluoroacetic acid (12 mL) was added to 3-(4-benzyloxyphenyl)-8-chloro-2-(2,4-difluorobenzyl)-2H-isoquinolin-1-one (1.34 g, 2.74 mmol), a compound of formula (Id), with stirring to afford a pale orange-brown solution. After standing at ambient temperature for 6 days there was only a trace of the starting 3-(4-benzyloxyphenyl)-8-chloro-2-(2,4-difluorobenzyl)-2H-isoquinolin-1-one remaining. The reaction solution was concentrated under reduced pressure to afford a brown foam. The crude product was purified by silica gel column chromatography eluting with a gradient from 10% to 40% ethyl acetate/hexane on silica. There was no appreciable separation from the column. Fractions containing both components visible by TLC were concentrated to afford a semi-solid. This material was boiled in hexane/EtOAc and upon cooling deposited a small amount of 8-chloro-2-(2,4-difluorobenzyl)-3-(4-hydroxyphenyl)-2H-isoquinolin-1-one, a compound of formula (Id), (268 mg, 25% yield) as a white powder. $^1$H-NMR (400 MHz, DMSO-d$_6$): δ 9.81 (1H, s), 7.67-7.62 (2H, m), 7.53 (1H, dd J=5.8, 3.3 Hz), 7.17-7.10 (3H, m), 6.98-6.92 (2H, m), 6.79-6.74 (2H, m), 6.59 (1H, s), 5.08 (2H, s).

F. To a solution of 2-(2,4-difluorobenzyl)-7-fluoro-3-(4-hydroxyphenyl)-2H-isoquinolin-1-one (54 mg, 0.14 mmol), a compound of formula (Id), in CH$_2$Cl$_2$ (8 mL) was added phenylboronic acid (35 mg, 0.28 mmol), copper (II) acetate (51 mg, 0.28 mmol), and powdered activated 4 Å molecular sieves (500 mg). The mixture was stirred for 10 minutes then treated with triethylamine (99 μL, 0.71 mmol). The resulting suspension was stirred for 72 hours at ambient temperature. The mixture was then filtered, and the filtrate was concentrated under reduced pressure. The crude product was purified by preparative thin-layer chromatography on silica gel eluting with 25% EtOAc/hexanes to afford 2-(2,4-difluorobenzyl)-7-fluoro-3-(4-phenoxyphenyl)-2H-isoquinolin-1-one, a compound of formula (Id), (29 mg, 45% yield) as a white solid. $^1$H-NMR (400 MHz, CDCl$_3$): δ 8.11 (1H, dd, J=9.4, 2.8 Hz), 7.52 (1H, dd, J=8.6, 5.1 Hz), 7.45-7.36 (3H, m), 7.19-7.14 (1H, m), 7.14-7.09 (2H, m), 7.08-7.03 (2H, m), 7.02-6.93 (3H, m), 6.78-6.72 (1H, m), 6.70-6.64 (1H, m), 6.47 (1H, s), 5.24 (2H, s) ppm.

G. To a solution of 8-chloro-2-(2,4-difluorobenzyl)-3-(4-hydroxyphenyl)-2H-isoquinolin-1-one, a compound of formula (Id), (54 mg, 0.13 mmol) in N,N-dimethylformamide (1.0 mL), was added powdered Cs$_2$CO$_3$ (89 mg, 0.27 mmol), followed by 2-chloronicotinonitrile (33 mg, 0.23 mmol). The resulting suspension was stirred and heated in a 105° C. oil bath. After stirring for 64 h at 105° C., HPLC analysis of the reaction mixture showed no 8-chloro-2-(2,4-difluorobenzyl)-3-(4-hydroxyphenyl)-2H-isoquinolin-1-one, nor 2-chloronicotinonitrile remaining. The reaction was allowed to cool to ambient temperature and was diluted with H$_2$O (15 mL), and Et$_2$O (50 mL). The layers were separated, the organic layer was washed with H$_2$O (10 mL), brine (10 mL), dried over Na$_2$SO$_4$, filtered and concentrated under reduced pressure to afford a yellow liquid. The crude product was purified by silica gel column chromatography by adsorbing the material onto silica gel from a CH$_2$Cl$_2$ solution, loading the resulting solid onto the column and eluting with a gradient from 10% to 40% EtOAc/hexane. The product peak was collected to afford 2-{4-[8-chloro-2-(2,4-difluorobenzyl)-1-oxo-1,2-dihydroisoquinolin-3-yl]phenoxy}nicotinonitrile, a compound of formula (Id), (36 mg, 57% yield) as a white solid. $^1$H-NMR (400 MHz, CDCl$_3$): δ 8.35 (1H, dd, J=5.0, 2.0 Hz), 8.05 (1H, dd, J=7.6, 1.8 Hz), 7.54-7.51 (2H, m), 7.42-7.38 (1 H, m), 7.27-7.24 (2H, m), 7.22-7.18 (2H, m), 7.15 (1H, dd, J=7.6, 5.0 Hz), 7.08-7.00 (1H, m), 6.80-6.74 (1H, m), 6.71-6.65 (1H, m), 6.46 (1H, s), 5.22 (2H, s).

H. In a similar manner, other compounds of formula (Id) are prepared.

EXAMPLE 8

Compounds of Formula (Ie)

A. Potassium carbonate (62 mg, 0.45 mmol), 3-(4-bromofuran-2-yl)-8-chloro-2-(2,4-difluorobenzyl)-2H-isoquinolin-1-one (61 mg, 0.14 mmol), and 2-(3-ethylsulfanyl-5-trifluoromethylphenyl)-4,4,5,5-tetramethyl-[1,3,2]dioxaborolane (59 mg, 0.18 mmol) were combined in a mixture of THF (3 mL), and H$_2$O (1 mL). The resulting biphasic mixture was sparged with nitrogen for 10 minutes. Dichloro[1,1'-bis(diphenylphosphino)ferrocene]palladium (II) dichloromethane adduct (12 mg, 15 μmol) was then added to afford a dark red-brown solution. After stirring at ambient temperature for 16 hours, HPLC analysis of the reaction showed a later eluting peak present as well as a quantity of the starting 3-(4-bromo-furan-2-yl)-8-chloro-2-(2,4-difluorobenzyl)-2H-isoquinolin-1-one remaining. An additional portion of the Pd catalyst was added and the reaction was then heated in an oil bath held at 60° C. After stirring for 150 minutes at 60° C., HPLC analysis showed the starting 3-(4-bromo-furan-2-yl)-8-chloro-2-(2,4-difluorobenzyl)-2H-isoquinolin-1-one to be consumed. The reaction was allowed to cool to ambient temperature, then diluted with Et$_2$O (50 mL), and H$_2$O (20 mL). The layers were separated and the aqueous layer was extracted with Et$_2$O (3×5 mL). The combined ether layers were washed with brine (10 mL), dried over Na$_2$SO$_4$, filtered, and concentrated under educed pressure to afford a brown film. The crude product was purified by silica gel column chromatography by adsorbing the material onto silica gel from a CH$_2$Cl$_2$ solution, loading the resulting solid onto the column and eluting with a gradient from 0% to 12% EtOAc/Hexane. The broad peak that was observed to elute from the column was concentrated under reduced pressure to afford 8-chloro-2-(2,4-difluorobenzyl)-3-[4-(3-ethylsulfanyl-5-trifluoromethylphenyl)furan-2-yl]-2H-isoquinolin-1-one (34 mg, 43% yield) as a clear film. $^1$H-NMR (400 MHz, CDCl$_3$): δ 7.79 (1H, d, J=0.8 Hz), 7.56-7.53 (2H, m), 7.49-7.41 (4H, m), 7.12-7.04 (1H, m), 6.81-6.71 (4H, m), 5.39 (2H, s), 3.02 (2H, q, J=7.3 Hz), 1.37 (3H, t, J=7.3 Hz).

B. In a similar manner, the following compounds of formula (Ie) were prepared:

8-chloro-2-(2,4-difluorobenzyl)-3-[5-(3,4-dimethoxyphenyl)thiophen-2-yl]-2H-isoquinolin-1-one; $^1$H-NMR (400 MHz, CDCl$_3$): δ 7.54-7.52 (2H, m), 7.45-7.41 (1H, m), 7.12 (1H, dd, J=8.3, 2.3 Hz), 7.08 (1H, d, J=3.4 Hz), 7.05-6.98 (2H, m), 6.91-6.86 (2H, m), 6.83-6.71 (2H, m), 6.67 (1H, s), 5.36 (2H, s), 3.94 (3H, s), 3.92 (3H, s) ppm;

3-[5-(3,5-bis-trifluoromethylphenyl)thiophen-2-yl]-8-chloro-2-(2,4-difluorobenzyl)-2H-isoquinolin-1-one; $^1$H-NMR (400 MHz, CDCl$_3$): δ 7.95 (2H, s), 7.82 (1H, s), 7.57-7.54 (2H, m), 7.46-7.42 (1H, m), 7.33 (1H, d, J=3.8 Hz), 7.09-7.02 (1H, m), 6.96-6.93 (1H, d, J=3.8 Hz), 6.85-6.79 (1H, m), 6.78-6.71 (1 H, m), 6.68 (1H, s), 5.34 (2H, s) ppm;

8-chloro-2-(2,4-difluorobenzyl)-3-[5-(4-methanesulfonylphenyl)thiophen-2-yl]-2H-isoquinolin-1-one; $^1$H-NMR (400 MHz, CDCl$_3$): δ 8.00-7.95 (2H, m), 7.75-7.71 (2H, m), 7.57-7.54 (2H, m), 7.46-7.42 (2H, m), 7.33 (1H, d, J=3.8 Hz), 7.08-7.01 (1H, m), 6.95 (1H, d, J=3.8 Hz), 6.84-6.78 (1H, m), 6.77-6.71 (1H, m), 6.68 (1H, s), 5.35 (2H, s), 3.09 (3H, s) ppm;

8-chloro-3-[5-(3-chloro-4-ethoxyphenyl)thiophen-2-yl]-2-(2,4-difluorobenzyl)-2H-isoquinolin-1-one; $^1$H-NMR (400 MHz, CDCl$_3$): δ 7.57 (1H, d, J=2.3 Hz), 7.54-7.52 (2H, m), 7.45-7.40 (1H, m), 7.37 (1H, dd, J=8.6, 2.5 Hz), 7.07 (1H, d, J=3.8 Hz), 7.03-6.98 (1H, m), 6.93 (1H, d, J=8.6 Hz), 6.86 (1H, d, J=3.8 Hz), 6.83-6.71 (2H, m), 6.66 (1H, s), 5.35 (2H, s), 4.15 (2H, q, J=7.1 Hz), 1.49 (3H, t, J=7.1 Hz) ppm;

8-chloro-3-[5-(3-chloro-4-ethoxyphenyl)furan-2-yl]-2-(2,4-difluorobenzyl)-2H-isoquinolin-1-one; $^1$H-NMR (400 MHz, CDCl$_3$): δ 7.55-7.52 (2H, m), 7.49-7.44 (1H, m), 7.28 (1H, d, J=2.3 Hz), 7.16 (1H, dd, J=8.3, 2.3 Hz), 7.06-7.13 (1H, m), 6.87-6.74 (4H, m), 6.61 (1H, d, J=3.5 Hz), 6.56 (1H, d, J=3.5 Hz), 5.34 (2H, s), 4.12 (2H, q, J=7.1 Hz), 1.48 (3H, t, J=7.1 Hz) ppm;

3-[5-(3,5-bis-trifluoromethylphenyl)furan-2-yl]-8-chloro-2-(2,4-difluorobenzyl)-2H-isoquinolin-1-one; $^1$H-NMR (400 MHz, CDCl$_3$): δ 7.78-7.75 (3H, m), 7.58-7.56 (2H, m), 7.50-7.47 (1H, m), 7.17-7.10 (1H, m), 6.89 (1H, d, J=3.3 Hz), 6.87-8.81 (1H, m), 6.79 (1H, s), 6.76-6.68 (2H, m), 5.33 (2H, s) ppm;

8-chloro-2-(2,4-difluorobenzyl)-3-[5-(4-methanesulfonylphenyl)furan-2-yl]-2H-isoquinolin-1-one; $^1$H-NMR (400 MHz, CDCl$_3$): δ 7.90-7.87 (2H, m), 7.58-7.55 (2H, m), 7.51-7.46 (3H, m), 7.14-7.07 (1H, m), 6.88-6.81 (2H, m), 6.81-6.72 (2H, m), 6.66 (1H, d, J=3.5 Hz), 5.37 (2H, s), 3.08 (3H, s) ppm;

8-chloro-3-[4-(3-chloro-4-ethoxyphenyl)thiophen-2-yl]-2-(2,4-difluorobenzyl)-2H-isoquinolin-1-one; $^1$H-NMR (400 MHz, CDCl$_3$): δ 7.55 (1H, s), 7.54 (1H, d, J=2.3 Hz), 7.46 (1H, d, J=2.3 Hz), 7.45-7.40 (1H, m), 7.37 (1H, d, J=1.5 Hz), 7.29-7.25 (1H, m), 7.09 (1H, d, J=1.5 Hz), 7.08-7.02 (1H, m), 6.94-6.89 (1H, m), 6.85-6.78 (1H, m), 6.77-6.71 (1H, m), 6.66 (1H, s), 5.33 (2H, s), 4.14 (2H, q, J=6.8 Hz), 1.49 (3H, t, J=6.8 Hz) ppm;

3-[4-(3,5-bis-trifluoromethylphenyl)thiophen-2-yl]-8-chloro-2-(2,4-difluorobenzyl)-2H-isoquinolin-1-one; $^1$H-NMR (400 MHz, CDCl$_3$): δ 7.85-7.81 (3H, m), 7.63 (1H, d, J=1.5 Hz), 7.59-7.52 (2H, m), 7.46-7.43 (1H, m), 7.15 (1H, d, J=1.5 Hz), 7.14-7.07 (1H, m), 6.88-6.81 (1H, m), 6.78-6.71 (1H, m), 6.68 (1H, s) ppm;

8-chloro-2-(2,4-difluorobenzyl)-3-[4-(4-methanesulfonylphenyl)thiophen-2-yl]-2H-isoquinolin-1-one; $^1$H-NMR (400 MHz, CDCl$_3$): δ 7.99-7.95 (2H, m), 7.66-7.61 (3H, m), 7.58-7.54 (2H, m), 7.45-7.42 (1H, m), 7.22-7.20 (1H, m), 7.11-7.04 (1H, m), 6.86-6.79 (1H, m), 6.75-6.69 (1H, m), 6.67 (1H, s), 5.34 (2H, s), 3.09 (3H, s) ppm;

3-[4-(4-amino-3-trifluoromethylphenyl)thiophen-2-yl]-8-chloro-2-(2,4-difluorobenzyl)-2H-isoquinolin-1-one; $^1$H-NMR (400 MHz, CDCl$_3$): δ 7.55 (1H, s), 7.54 (1H, d, J=2.3 Hz), 7.48-7.46 (1H, m), 7.44-7.41 (1H, m), 7.41-7.37 (1H, m), 7.34 (1H, d, J=1.5 Hz), 7.09-7.02 (2H, m), 6.84-6.78 (1H, m), 6.78-6.70 (2H, m), 6.66 (1H, s), 5.33 (2H, s), 4.25 (2H, s) ppm;

3-[4-(4-amino-3-chloro-phenyl)thiophen-2-yl]-8-chloro-2-(2,4-difluorobenzyl)-2H-isoquinolin-1-one; $^1$H-NMR (400 MHz, CDCl$_3$): δ 7.54 (1H, s), 7.53 (1H, d, J=2.0 Hz), 7.42 (1H, dd, J=5.8, 3.5 Hz), 7.33 (1H, d, J=2.0 Hz), 7.30 (1H, d, J=1.5 Hz), 7.16 (1H, dd, J=8.3, 2.0 Hz), 7.09-7.01 (2H, m), 6.84-6.71 (3H, m), 6.66 (1H, s), 5.33 (2H, s), 4.12 (2H, s) ppm;

8-chloro-2-(2,4-difluorobenzyl)-3-[4-(4-ethoxy-3-trifluoromethylphenyl)thiophen-2-yl]-2H-isoquinolin-1-one;

¹H-NMR (400 MHz, CDCl₃): δ 7.62-7.61 (1H, m), 7.56-7.51 (3H, m), 7.44-7.41 (1H, m), 7.40 (1H, d, J=1.5 Hz), 7.10 (1H, d, J=1.5 Hz), 7.08-7.03 (1H, m), 7.00 (1H, d, J=8.3 Hz), 6.85-6.79 (1H, m), 6.77-6.70 (1H, m), 6.67 (1H, s), 5.33 (2H, s), 4.16 (2H, q, J=7.1 Hz), 1.47 (3H, t, J=7.1 Hz) ppm;

8-chloro-2-(2,4-difluorobenzyl)-3-[5-(4-ethoxy-3-trifluoromethylphenyl)thiophen-2-yl]-2H-isoquinolin-1-one; ¹H-NMR (400 MHz, CDCl₃): δ 7.73 (1H, d, J=2.3 Hz), 7.62 (1H, dd, J=8.8, 2.3 Hz), 7.55-7.51 (2H, m), 7.45-7.40 (1H, m), 7.11 (1H, d, J=3.8 Hz), 7.06-6.99 (2H, m), 6.88 (1H, d, J=3.8 Hz), 6.83-6.71 (2H, m), 6.67 (1H, s), 5.35 (2H, s), 4.16 (2H, q, J=7.1 Hz), 1.47 (3H, t, J=7.1 Hz) ppm;

3-[5-(4-amino-3-trifluoromethylphenyl)thiophen-2-yl]-8-chloro-2-(2,4-difluorobenzyl)-2H-isoquinolin-1-one; ¹H-NMR (400 MHz, CDCl₃): δ 7.61 (1H, d, J=2.0 Hz), 7.54-7.51 (2H, m), 7.46 (1H, dd, J=8.6, 2.0 Hz), 7.44-7.40 (1H, m), 7.05 (1H, d, J=3.8 Hz), 7.04-6.98 (1H, m), 6.86 (1H, d, J=3.8 Hz), 6.82-6.71 (3H, m), 6.66 (1H, s), 5.35 (2H, s), 4.31 (2H, s) ppm;

3-[5-(4-amino-3-chloro-phenyl)thiophen-2-yl]-8-chloro-2-(2,4-difluorobenzyl)-2H-isoquinolin-1-one; ¹H-NMR (400 MHz, CDCl₃): δ 7.54-7.51 (2H, m), 7.46 (1H, d, J=2.0 Hz), 7.44-7.40 (1H, m), 7.24 (1H, d, J=2.0 Hz), 7.04-6.97 (2H, m), 6.84 (1H, d, J=3.8 Hz), 6.82-6.71 (3H, m), 6.66 (1H, s), 5.35 (2H, s), 4.19 (2H, s) ppm;

8-chloro-3-[4-(3-chloro-4-diethylamino-phenyl)thiophen-2-yl]-2-(2,4-difluorobenzyl)-2H-isoquinolin-1-one; ¹H-NMR (400 MHz, CDCl₃): δ 7.55-7.53 (2H, m), 7.43 (1H, d, J=2.0 Hz), 7.41 (1H, dd, J=5.8, 3.5 Hz), 7.39 (1H, d, J=1.5 Hz), 7.29-7.24 (1H, m), 7.11 (1H, d, J=1.5 Hz), 7.09-7.02 (2H, m), 6.85-6.79 (1H, m), 6.78-6.72 (1H, m), 6.66 (1H, s), 5.33 (2H, s), 3.17 (4H, q, J=7.1 Hz), 1.06 (6H, t, J=7.1 Hz) ppm;

8-chloro-3-[4-(3-chloro-4-ethylamino-phenyl)thiophen-2-yl]-2-(2,4-difluorobenzyl)-2H-isoquinolin-1-one; ¹H-NMR (400 MHz, CDCl₃): δ 7.55-7.52 (2H, m), 7.42 (1H, dd, J=5.6, 4.0 Hz), 7.35 (1H, d, J=2.0 Hz), 7.29 (1H, d, J=1.5 Hz), 7.23 (1H, dd, J=8.6, 2.0 Hz), 7.08-7.01 (2H, m), 6.84-6.78 (1H, m), 6.78-6.71 (1H, m), 6.67-6.64 (2H, m), 5.33 (2H, s), 4.31-4.25 (1H, m), 3.28-3.20 (2H, m), 1.33 (3H, t, J=7.1 Hz) ppm;

8-chloro-3-[4-(3-chloro-4-ethoxyphenyl)furan-2-yl]-2-(2,4-difluorobenzyl)-2H-isoquinolin-1-one; ¹H-NMR (400 MHz, CDCl₃): δ 7.66 (1H, s), 7.54 (1H, s), 7.53 (1H, d, J=1.8 Hz), 7.47-7.43 (2H, m), 7.23 (1H, d, 2.3 Hz), 7.10-7.03 (1H, m), 6.93 (1H, d, J=8.6 Hz), 6.80-6.72 (3H, m), 6.69 (1H, s), 5.39 (2H, s), 4.14 (2H, q, J=7.1 Hz), 1.49 (3H, t, J=7.1 Hz) ppm;

3-[4-(3,5-bis-trifluoromethylphenyl)furan-2-yl]-8-chloro-2-(2,4-difluorobenzyl)-2H-isoquinolin-1-one; ¹H-NMR (400 MHz, CDCl₃): δ 7.87 (1H, d, J=0.8 Hz), 7.84 (2H, s), 7.81 (1H, s), 7.57 (1H, s), 7.56 (1H, d, J=3.8 Hz), 7.46 (1H, dd, J=6.6, 2.8 Hz), 7.15-7.07 (1H, m), 6.81-6.71 (4H, m), 5.39 (2H, s) ppm;

8-chloro-2-(2,4-difluorobenzyl)-3-[5-(4-ethylamino-3-trifluoromethylphenyl)thiophen-2-yl]-2H-isoquinolin-1-one; ¹H-NMR (400 MHz, CDCl₃): δ 7.62-7.60 (1H, m), 7.55-7.51 (3H, m), 7.44-7.40 (1H, m), 7.05-6.98 (2H, m), 6.85 (1H, d, J=3.8 Hz), 6.82-6.72 (3H, m), 6.67 (1H, s), 5.36 (2H, s), 4.40 (1H, s), 3.29-3.22 (2H, m), 1.32 (3H, t, J=7.1 Hz) ppm;

8-chloro-3-[5-(3-trifluoromethyl-4-(bis-methanesulfonylamino)-phenyl)thiophen-2-yl]-2-(2,4-difluorobenzyl)-2H-isoquinolin-1-one; ¹H-NMR (400 MHz, CDCl₃): δ 7.95 (1H, d, J=2.0 Hz), 7.77 (1H, dd, J=8.3, 2.3 Hz), 7.56 (1H, s), 7.55 (1H, d, J=2.3 Hz), 7.47 (1H, d, J=8.3 Hz), 7.45-7.42 (1H, m), 7.31 (1H, d, J=4.0 Hz), 7.08-6.99 (1H, m), 6.95 (1H, d, J=3.8 Hz), 6.84-6.71 (2H, m), 6.68 (1H, s), 5.34 (2H, s), 3.51 (6H, s) ppm;

8-chloro-2-(2,4-difluorobenzyl)-3-[4-(4-methanesulfonylphenyl)furan-2-yl]-2H-isoquinolin-1-one; ¹H-NMR (400 MHz, CDCl₃): δ 7.98-7.95 (2H, m), 7.86-7.85 (1H, m), 7.63-7.60 (2H, m), 7.58-7.52 (2H, m), 7.47 -7.44 (1H, m), 7.13-7.05 (1H, m), 6.81-6.71 (4H, m), 5.39 (2H, s), 3.08 (3H, s) ppm;

8-chloro-2-(2,4-difluorobenzyl)-3-[5-(3-ethanesulfonyl-5-trifluoromethylphenyl)thiophen-2-yl]-2H-isoquinolin-1-one; ¹H-NMR (400 MHz, CDCl₃): δ 8.24-8.22 (1H, m), 8.09 (1H, s), 8.02 (1H, s), 7.57 (1H, s), 7.56 (1H, d, J=2.3 Hz), 7.44 (1H, dd, J=5.6, 3.5 Hz), 7.37 (1H, d, J=3.8 Hz), 7.10-7.03 (1H, m), 6.96 (1H, d, J=3.8 Hz), 6.85-6.79 (1H, m), 6.78-6.71 (1H, m), 6.68 (1H, s), 5.34 (2H, s), 3.21 (2H, q, J=7.6 Hz), 1.36 (3H, t, J=7.6 Hz) ppm;

8-chloro-2-(2,4-difluorobenzyl)-3-[4-(3-ethanesulfonyl-5-trifluoromethylphenyl)furan-2-yl]-2H-isoquinolin-1-one; ¹H-NMR (400 MHz, CDCl₃): δ 8.14-8.12 (1H, m), 8.08 (1H, s), 7.93-7.90 (2H, m), 7.57 (1H, s), 7.56 (1H, d, J=3.8 Hz), 7.46 (1H, J=6.6, 2.8 Hz), 7.16-7.09 (1H, m), 6.83 (1H, d, J=0.9 Hz), 6.81-6.72 (3H, m), 5.39 (2H, s), 3.20 (2H, q, J=7.6 Hz), 1.35 (3H, t, J=7.6 Hz) ppm;

3-[4-(4-amino-3-trifluoromethylphenyl)furan-2-yl]-8-chloro-2-(2,4-difluorobenzyl)-2H-isoquinolin-1-one; ¹H-NMR (400 MHz, CDCl₃): δ 7.65 (1H, d, J=1.0 Hz), 7.55-7.51 (2H, m), 7.47-7.43 (2H, m), 7.35 (1H, dd, J=8.3, 1.5 Hz), 7.10-7.03 (1H, m), 6.79-6.72 (4H, m), 6.69 (1H, d, J=1.0 Hz), 5.39 (2H, br s), 4.24 (2H, br s) ppm;

8-chloro-2-(2,4-difluorobenzyl)-3-[5-(3-ethylsulfanyl-5-trifluoromethylphenyl)furan-2-yl]-2H-isoquinolin-1-one; ¹H-NMR (400 MHz, CDCl₃): δ 7.56 (1H, s), 7.55 (1H, d, J=1.0 Hz), 7.48 (1H, q, J=4.0 Hz), 7.45-7.43 (1H, m), 7.39 (2H, d, J=5.6 Hz), 7.15-7.08 (1H, m), 6.86-6.71 (4H, m), 6.64 (1H, d, J=3.5 Hz), 5.34 (2H, s), 2.99 (2H, q, J=7.3 Hz), 1.35 (3H, t, J=7.3 Hz) ppm;

8-chloro-2-(2,4-difluorobenzyl)-3-[5-(3-ethanesulfonyl-5-trifluoromethylphenyl)furan-2-yl]-2H-isoquinolin-1-one; ¹H-NMR (400 MHz, CDCl₃): δ 8.19 (1H, s), 8.03 (1H, s), 7.80 (1H, s), 7.58 (1H, s), 7.56 (1H, d, J=1.5 Hz), 7.53-7.48 (1H, m), 7.17-7.10 (1H, m), 6.94 (1H, d, J=3.5 Hz), 6.87-6.82 (1H, m), 6.80 (1H, s), 6.76-6.69 (1H, m), 6.67 (1H, d, J=3.5 Hz), 5.34 (2H, s), 3.17 (2H, q, J=7.3 Hz), 1.34 (3H, t, J=7.3 Hz) ppm;

8-chloro-2-(2,4-difluorobenzyl)-3-[4-(4-ethylamino-3-trifluoromethylphenyl)furan-2-yl]-2H-isoquinolin-1-one; ¹H-NMR (400 MHz, CDCl₃): δ 7.65 (1H, d, J=1.0 Hz), 7.55-7.52 (2H, m), 7.48-7.39 (3H, m), 7.10-7.03 (1H, m), 6.79-6.72 (4H, m), 6.69 (1H, d J,=1.0 Hz), 5.39 (2H, br s), 4.31 (1H, br m), 3.24 (2H, dq, J=7.1, 4.8 Hz), 1.32 (3H, t, J=7.3 Hz) ppm;

8-chloro-2-(2,4-difluorobenzyl)-3-[5-(6-ethoxy-pyridin-3-yl)-thiophen-2-yl]-2H-isoquinolin-1-one; ¹H-NMR (400 MHz, CDCl₃): δ 8.35 (1H, d, J=2.5 Hz), 7.71 (1H, dd, J=8.6, 2.5 Hz), 7.53 (2H, d, J=4.6 Hz), 7.45-7.40 (1H, m), 7.09 (1H, d, J=3.8 Hz), 7.05-6.98 (1H, m), 6.90 (1H, d, J=3.8 Hz), 6.83-6.72 (3H, m), 6.67 (1H, s), 5.35 (2H, s), 4.39 (2H, q, J=7.3 Hz), 1.42 (3H, t, J=7.3 Hz) ppm;

5-{5-[8-chloro-2-(2,4-difluorobenzyl)-1-oxo-1,2-dihydro-isoquinolin-3-yl]-thiophen-2-yl}-2-ethoxynicotinonitrile; ¹H-NMR (400 MHz, CDCl₃): δ 8.50 (1H, d, J=2.5 Hz), 7.99 (1H, d, J=2.5 Hz), 7.56 (1H, s), 7.54 (1H, d, J=1.8 Hz), 7.43 (1H, dd, J=5.6, 3.8 Hz), 7.13 (1H, d, J=3.8 Hz), 7.07-7.00 (1H, m), 6.92 (1H, d, J=3.5 Hz), 6.84-6.71 (2H, m), 6.66 (1H, s), 5.33 (2H, s), 4.54 (2H, q, J=7.1 Hz), 1.47 (3H, t, J=7.1 Hz) ppm;

8-chloro-2-(2,4-difluorobenzyl)-3-(4'-methanesulfonyl-biphenyl-3-yl)-2H-isoquinolin-1-one; $^1$H-NMR (400 MHz, CDCl$_3$): δ 8.01-7.97 (2H, m), 7.68-7.65 (1H, m), 7.59-7.55 (2H, m), 7.55 (1H, s), 7.53 (1H, d, J=2.0 Hz), 7.50 (1H, t, J=7.8 Hz), 7.43-7.37 (1H, m), 7.35-7.33 (1H, m), 7.30-7.27 (1H, m), 7.15-7.09 (1H, m), 6.83-6.77 (1H, m), 6.61-6.55 (1H, m), 6.46 (1H, s), 5.20 (2H, s), 3.10 (3H, s) ppm; and 8-chloro-2-(2,4-difluorobenzyl)-3-(3'-ethanesulfonyl-5'-trifluoromethyl-biphenyl-3-yl)-2H-isoquinolin-1-one; $^1$H-NMR (400 MHz, CDCl3): δ 8.18-8.15 (2H, m), 7.88 (1H, s), 7.71-7.67 (1H, m), 7.57-7.51 (3H, m), 7.45-7.39 (1H, m), 7.38-7.31 (2H, m), 7.16-7.09 (1H, m), 6.84-6.77 (1H, m), 6.61-6.55 (1H, m), 6.46 (1H, s), 5.20 (2H, s), 3.19 (2H, q, J=7.3 Hz), 1.35 (3H, t, J=7.3 Hz) ppm;

8-chloro-2-(2,4-difluorobenzyl)-3-[3-(6-ethoxypyridin-3-yl)-phenyl]-2H-isoquinolin-1-one; 1 H-NMR (400 MHz, CDCl3): δ 8.25 (1H, m), 7.59-7.51 (4H, m), 7.46-7.38(2H, m), 7.30-7.28(1H, m), 7.20-7.16 (1H, m), 7.12-7.05 (1H, m), 6.82-6.75(2H, m), 6.63-6.57 (1H, m), 6.46 (1H, s), 5.21 (2H, s), 4.40 (2H, q, J=7.3 Hz), 1.42 (3H, t, J=7.3 Hz) ppm;

5-{3-[8-chloro-2-(2,4-difluorobenzyl)-1-oxo-1,2-dihydroisoquinolin-3-yl]-phenyl}-2-ethoxy-nicotinonitrile; 1H-NMR (400 MHz, CDCl3): δ 8.37 (1H, d, J=2.5 Hz), 7.88 (1H, d, J=2.5 Hz), 7.57-7.51 (3H, m), 7.51-7.46 (1H, m), 7.42-7.39 (1H, m), 7.29-7.23 (2H, m), 7.15-7.08 (1H, m), 6.84-6.78 (1H, m), 6.65-6.58 (1H, m), 6.45 (1H, s), 5.19 (2H, s), 4.54 (2H, q, J=7.1 Hz), 1.47 (3H, t, J=7.1 Hz) ppm;

3-(3',5'-bis-trifluoromethylbiphenyl-3-yl)-8-chloro-2-(2,4-difluorobenzyl)-2H-isoquinolin-1-one; 1H-NMR (400 MHz, CDCl3): δ 7.87 (1H, s), 7.80 (2H, s), 7.69-7.66 (1H, m), 7.56-7.51 (3H, m), 7.41 (1H, dd, J=5.8 Hz, J=3.5 Hz), 7.35-7.31 (2H, m), 7.16-7.09 (1H, m), 6.84-6.77 (1H, m), 6.62-6.55 (1H, m), 6.46 (1H, s), 5.19 (2H, s) ppm; and 8-chloro-3-(3'-chloro-4'-ethoxybiphenyl-3-yl)-2-(2,4-difluorobenzyl)-2H-isoquinolin-1-one; 1H-NMR (400 MHz, CDCl3): δ 7.60-7.56 (1H, m), 7.54-7.51 (2H, m), 7.45-7.37 (3H, m), 7.29-7.25 (1H, m), 7.22-7.15 (2H, m), 7.13-7.06 (1H, m), 6.94 (1H, d, J=9.1 Hz), 6.84-6.78 (1H, m), 6.66-6.60 (1H, m), 6.46 (1H, s), 5.20 (2H, s), 4.15 (2H, q, J=7.1 Hz), 1.50 (3H, t, J=7.1 Hz) ppm.

C. To a solution of 8-chloro-2-(2,4-difluorobenzyl)-3-[4-(3-ethylsulfanyl-5-trifluoromethylphenyl)furan-2-yl]-2H-isoquinolin-1-one (33 mg, 57 μmol) in CH$_2$Cl$_2$ (3.0 mL) was added 3-chloro-peroxybenzoic acid (70% pure) (32 mg, 130 μmol) at ambient temperature. After stirring for 90 min at ambient temperature, TLC analysis of the reaction showed one major product spot at lower rf. At this time the reaction was quenched by the addition of aqueous sodium thiosulfate solution, and dilution with additional CH$_2$Cl$_2$ (20 mL), H$_2$O (5 mL), and saturated aqueous NaHCO$_3$ solution (5 mL). The layers were separated, and the aqueous layer was extracted with CH$_2$Cl$_2$ (3×10 mL). The combined CH$_2$Cl$_2$ layers were dried over Na$_2$SO$_4$, filtered, and concentrated under reduced pressure to afford a yellow film. The crude product was purified by silica gel column chromatography by adsorbing the material onto silica gel from a CH$_2$Cl$_2$ solution, loading the resulting solid onto the column and eluting with a gradient from 0% to 32% EtOAc/hexane. The large peak that was observed to elute was collected and concentrated under reduced pressure to afford 8-chloro-2-(2,4-difluorobenzyl)-3-[4-(3-ethanesulfonyl-5-trifluoromethylphenyl)furan-2-yl]-2H-isoquinolin-1-one (22 mg, 62% yield) as a yellow film. $^1$H-NMR (400 MHz, CDCl$_3$): δ 8.13 (1H, m), 8.08 (1H, m), 7.93-7.88 (2H, m), 7.59-7.55 (2H, m), 7.48-7.44 (1H, m), 7.16-7.08 (1H, m), 6.83 (1H, d, J=0.8 Hz), 6.81-6.73 (3H, m), 5.39 (2H, s), 3.2 (2H, q, J=7.3 Hz), 1.35 (3H, t, J=7.3 Hz).

D. To a solution of 3-[5-(4-amino-3-trifluoromethylphenyl)thiophen-2-yl]-8-chloro-2-(2,4-difluorobenzyl)-2H-isoquinolin-1-one (28 mg, 51 μmol) in toluene (1 mL) was added one drop of acetic acid, and a molar excess of acetaldehyde. The mixture was stirred for 20 minutes at ambient temperature and then concentrated under reduced pressure. The residue was taken up in 25% HOAc/MeOH (1 mL), and a molar excess of NaCNBH$_3$ was added. After stirring for 16 hours at ambient temperature there was still starting material present. Additional acetaldehyde was added. After 30 minutes a yellow solid appeared in the reaction. This solid was collected by filtration and was purified by silica gel column chromatography eluting with a gradient from 0% to 20% ethyl acetate/hexane on silica. The product peak was collected to afford 8-chloro-2-(2,4-difluorobenzyl)-3-[5-(4-ethylamino-3-trifluoromethylphenyl)thiophen-2-yl]-2H-isoquinolin-1-one (10 mg, 34% yield) as a yellow solid. $^1$H-NMR (400 MHz, CDCl$_3$): δ 7.62-7.60 (1H, m), 7.55-7.51 (3H, m), 7.44-7.40 (1H, m), 7.05-6.98 (2H, m), 6.85 (1H, d, J=3.8 Hz), 6.82-6.72 (3H, m), 6.67 (1H, s), 5.36 (2H, s), 4.40 (1H, s), 3.29-3.22 (2H, m), 1.32 (3H, t, J=7.1 Hz) ppm.

E. In a similar manner, other compounds of formula (Ie) are prepared.

EXAMPLE 9

This example illustrates the preparation of representative pharmaceutical compositions for oral administration containing a compound of the invention, or a pharmaceutically acceptable salt thereof:

| A. Ingredients | % wt./wt. |
|---|---|
| Compound of the invention | 20.0% |
| Lactose | 79.5% |
| Magnesium stearate | 0.5% |

The above ingredients are mixed and dispensed into hard-shell gelatin capsules containing 100 mg each, one capsule would approximate a total daily dosage.

| B. Ingredients | % wt./wt. |
|---|---|
| Compound of the invention | 20.0% |
| Magnesium stearate | 0.9% |
| Starch | 8.6% |
| Lactose | 69.6% |
| PVP (polyvinylpyrrolidine) | 0.9% |

The above ingredients with the exception of the magnesium stearate are combined and granulated using water as a granulating liquid. The formulation is then dried, mixed with the magnesium stearate and formed into tablets with an appropriate tableting machine.

| C. Ingredients | |
|---|---|
| Compound of the invention | 0.1 g |
| Propylene glycol | 20.0 g |
| Polyethylene glycol 400 | 20.0 g |
| Polysorbate 80 | 1.0 g |
| Water | q.s. 100 mL |

The compound of the invention is dissolved in propylene glycol, polyethylene glycol 400 and polysorbate 80. A sufficient quantity of water is then added with stirring to provide 100 mL of the solution which is filtered and bottled.

| D. Ingredients | % wt./wt. |
|---|---|
| Compound of the invention | 20.0% |
| Peanut Oil | 78.0% |
| Span 60 | 2.0% |

The above ingredients are melted, mixed and filled into soft elastic capsules.

| E. Ingredients | % wt./wt. |
|---|---|
| Compound of the invention | 1.0% |
| Methyl or carboxymethyl cellulose | 2.0% |
| 0.9% saline | q.s. 100 mL |

The compound of the invention is dissolved in the cellulose/saline solution, filtered and bottled for use.

EXAMPLE 10

This example illustrates the preparation of a representative pharmaceutical formulation for parenteral administration containing a compound of the invention, or a pharmaceutically acceptable salt thereof:

| Ingredients | |
|---|---|
| Compound of the invention | 0.02 g |
| Propylene glycol | 20.0 g |
| Polyethylene glycol 400 | 20.0 g |
| Polysorbate 80 | 1.0 g |
| 0.9% Saline solution | q.s. 100 mL |

The compound of the invention is dissolved in propylene glycol, polyethylene glycol 400 and polysorbate 80. A sufficient quantity of 0.9% saline solution is then added with stirring to provide 100 mL of the I.V. solution which is filtered through a 0.2 m membrane filter and packaged under sterile conditions.

EXAMPLE 11

This example illustrates the preparation of a representative pharmaceutical composition in suppository form containing a compound of the invention, or a pharmaceutically acceptable salt thereof:

| Ingredients | % wt./wt. |
|---|---|
| Compound of the invention | 1.0% |
| Polyethylene glycol 1000 | 74.5% |
| Polyethylene glycol 4000 | 24.5% |

The ingredients are melted together and mixed on a steam bath, and poured into molds containing 2.5 g total weight.

EXAMPLE 12

This example illustrates the preparation of a representative pharmaceutical formulation for insufflation containing a compound of the invention, or a pharmaceutically acceptable salt thereof:

| Ingredients | % wt./wt. |
|---|---|
| Micronized compound of the invention | 1.0% |
| Micronized lactose | 99.0% |

The ingredients are milled, mixed, and packaged in an insufflator equipped with a dosing pump.

EXAMPLE 13

This example illustrates the preparation of a representative pharmaceutical formulation in nebulized form containing a compound of the invention, or a pharmaceutically acceptable salt thereof:

| Ingredients | % wt./wt. |
|---|---|
| Compound of the invention | 0.005% |
| Water | 89.995% |
| Ethanol | 10.000% |

The compound of the invention is dissolved in ethanol and blended with water. The formulation is then packaged in a nebulizer equipped with a dosing pump.

EXAMPLE 14

This example illustrates the preparation of a representative pharmaceutical formulation in aerosol form containing a compound of the invention, or a pharmaceutically acceptable salt thereof:

| Ingredients | % wt./wt. |
|---|---|
| Compound of the invention | 0.10% |
| Propellant 11/12 | 98.90% |
| Oleic acid | 1.00% |

The compound of the invention is dispersed in oleic acid and the propellants. The resulting mixture is then poured into an aerosol container fitted with a metering valve.

EXAMPLE 13

FRET Coactivator Assay

The FRET coactivator assay measures the ability of LXR ligands to promote protein-protein interactions between the ligand binding domain (LBD) of LXR and transcriptional coactivator proteins. The assay involves the use a recombinant Glutathione-S-transferase (GST)-nuclear receptor ligand binding domain (LBD) fusion protein and a synthetic biotinylated peptide sequence derived from the receptor interacting domain of a co-activator peptide such as the steroid receptor coactivator 1 (SRC-1). Typically GST-LBD is labeled with a europium chelate (donor) via a europium-tagged anti-GST antibody, and the coactivator peptide is labeled with allophycocyanin via a streptavidin-biotin linkage.

In the presence of an agonist for the nuclear receptor, the peptide is recruited to the GST-LBD bringing europium and allophycocyanin into close proximity to enable energy transfer from the europium chelate to the allophycocyanin. Upon excitation of the complex with light at 340 nm excitation energy absorbed by the europium chelate is transmitted to the allophycocyanin moiety resulting in emission at 665 nm. If the europium chelate is not brought into close proximity to the allophycocyanin moiety there is little or no energy transfer and excitation of the europium chelate results in emission at 615 nm. Thus the intensity of light emitted at 665 nm gives an indication of the strength of the protein-protein interaction.

A. Required Materials

1. Partially purified recombinant protein comprising glutathione-S-transferase fused in frame to the LXR-ligand binding domain (comprising amino acids 188-447 of human LXRα, or amino acids 198-461 of human LXRβ).
2. Biotinylated peptide containing a SRC-1 LXXLL receptor interaction motif (B-SRC-1)
3. Anti-GST antibody conjugated to an Europium chelate (αGST-K) (From Wallac/PE Life Sciences Cat# AD0064)
4. Streptavidin linked allophycocyanin (SA-APC) (From Wallac/PE Life Sciences CAT# AD0059A)
5. 1×FRET Buffer: (20 mM $KH_2PO_4/K_2HPO_4$ pH 7.3, 150 mM NaCl, 2.5 mM CHAPS, 2 mM EDTA, 1 mM DTT (add fresh))
6. 96 well or 384 well black multiwell plates (from LJL)

Stock Solutions 0.5 M $KH_2PO_4/K_2HPO_4$: pH 7.3
5 M NaCl
80 mM (5%) CHAPS
0.5 M EDTA pH 8.0
1 M DTT (keep at −20° C.)

B. Preparation of Screening Reagents

Prepare reaction mixture for the appropriate number of wells by combining the following reagents 5 nM/well GST-hLXR αLBD, 5 nM/well GST-hLXR βLBD, 5 nM/well Anti-GST antibody (Eu), 12 nM/well biotin-SRC-1 peptide, 12 nM/well APC-SA adjust the volume to 10 μL/well with 1×-FRET buffer.

C. Procedure

Add 0.5 μL of a 1 mM stock compound (for approx. 10 μM final concentration) or solvent to each well in a 96 well or 384 well black plate (LJL).

Add 10 μl reaction mixture (prepared above) to each well of the multiwell plate.

Incubate covered or in the dark (the APC is light sensitive) at ambient temperature for 1-4 hours. After this time if reactions are not read they can be stored at 4° C. for several more hours without too much loss of signal.

Read the plate using an LJL Analyst, or similar instrument, using the following conditions:

Channel 1: Excitation is 330 nm and emission is 615. This is for Eu chelate

Channel 2: Excitation is 330 nm and emission is 665. This is for APC

For channel 1: Flashes per well=100; Integration time=1000 μs; interval between flashes=1×10 ms; Delay after flash=200 μs For channel 2: Flashes per well=100; Integration time=100 μs; interval between flashes=1×10 ms; Delay after flashes=65 μs

EXAMPLE 14

Scintillation Proximity Assay (SPA)

The SPA assay measures the radioactive signal generated by the binding of $^3$H-24,25-epoxycholesterol to LXRα or LXRβ. The basis of the assay is the use of SPA beads containing a scintillant, such that when binding to the receptor brings the labeled ligand into proximity with the bead, the energy from the label stimulates the scintillant to emit light. The light is measured using a standard microplate scintillation reader. The ability of a ligand to bind to a receptor can be measured by assessing the degree to which the compound can compete off a radiolabelled ligand with known affinity for the receptor.

A. Required Materials

1. Label: $^3$H-24,25-epoxy-cholesterol (Amersham)
2. LXRα lysate: Baculovirus expressed LXRα/RXR heterodimer with RXR having a 6-HIS tag produced as a crude lysate
3. LXRβ lysate: Baculovirus expressed LXRβ/RXR heterodimer with RXR having a 6-HIS tag produced as a crude lysate
4. SPA beads: Ysi copper His-tag SPA beads (Amersham)
5. Plates: Non-binding surface 96-well plate (Corning)
6. Protein lysate dilution buffer: (20 mM Tris-HCl pH 7.9, 500 mM NaCl, 5 mM Imidazole).
7. 2×SPA Buffer: (40 mM $K_2HPO_4/KH_2PO_4$ pH7.3, 100 mM NaCl, 0.05% Tween 20, 20% Glycerol, 4 mM EDTA)
8. 2×SPA Buffer w/o EDTA: (40 mM $K_2HPO_4/KH_2PO_4$ pH7.3, 100 mM NaCl, 0.05% Tween 20, 20% Glycerol)

B. Stock Solutions 0.5 M $K_2HPO_4/KH_2PO_4$ pH 7.3
0.5 M EDTA pH 8.0
5 M NaCl
10% Tween-20
Glycerol C. Preparation of Protein Lysates Baculovirus expression plasmids for human RXR α (accession No NM_002957), LXR a (accession No U22662), LXR β (accession No U07132) were made by cloning the appropriate full-length cDNAs into the pBacPakhis1 vector (Clontech, CA) following standard procedures. Insertion of the cDNAs into the pBAcPakhis1 vector polylinker created an in frame fusion to the cDNA to an N-terminal poly-His tag present in pBacPakhis1. Correct cloning was confirmed by restriction mapping, and/or sequencing.

Cell lysates were prepared by infecting healthy, Sf9 insect cells at a density of approximately $1.25 \times 10^6$/ml at 27° C., in a total volume of 500 mL per 1 L sized spinner flasks, cultured under standard conditions. To prepare LXRα lysate, insect cells were co-transfected with the LXR α expression cassette at an M.O.I of 0.5 to 0.8 and with the RXR expression cassette at a M.O.I. of approximately 1.6. To prepare LXRβ lysate, insect cells were co-transfected with the LXR β expression cassette at an M.O.I of approximately 1.6 and with the RXR expression cassette at a M.O.I. of approximately 1.6. In both cases cells were incubated for 48 hours at 27° C. with constant shaking prior to harvesting.

After incubation, cells were harvested by centrifugation and pelleted. Cell pellets were resuspended in two volumes of ice-cold freshly prepared extraction buffer (20 mM Tris pH 8.0, 10 mM Imidazole, 400 mM NaCl, containing one EDTA free protease inhibitor tablet (Roche Catalog No: 1836170) per 10 ml of extraction buffer).

Cells were homogenized slowly on ice using a Douncer to achieve 80-90% cell lysis. The homogenate was centrifuged in a pre-chilled rotor (Ti50 or Ti70, or equivalent) at 45,000 rpm for 30 minutes at 4° C. Aliquots of the supernatant were frozen on dry ice and stored frozen at −80° C. until quantification and quality control. Aliquots of the lysates were tested in the SPA assay to ensure lot to lot consistency, and via SDS-PAGE analysis after purification using Ni-NTA Resin (Qiagen) and adjusted for protein concentration and expression level prior to use in screening assays.

D. Preparation of Screening Reagents

[$^3$H] 24,25 Epoxycholesterol (EC) solution: For a single 384-well plate (or 400 wells), 21 µL of [$^3$H] EC (specific activity 76.5 Ci/mmol, concentration 3.2 mCi/mL) was added to 4.4 mL of 2×SPA buffer to provide for a final concentration of 200 nM. For each additional 384-well plate, an additional 19.1 µL of [$^3$H] EC was added to 4.0 mL of additional 2×SPA buffer. The final concentration of [$^3$H] EC in the well was 50 nM.

LXRα lysate (prepared as above) was diluted with protein lysate dilution buffer. 1400 µL of diluted LXRα lysate was prepared per 384-well plate, (or 200 wells) and 1120 µL of diluted LXRα lysate was prepared for each additional 384-well plate.

LXRβ lysate (prepared as above) was diluted with protein lysate dilution buffer. 1400 µL of diluted LXRβ lysate was prepared per 384-well plate, (or 200 wells) and 1120 µL of diluted LXRβ lysate was prepared for each additional 384-well plate.

SPA bead solution: For a 384-well plate (or 400 wells), 3.75 mL of 2×SPA buffer w/o EDTA, 2.25 mL of H$_2$O, and 1.5 mL of Ysi His-tag SPA beads (vortex well before taking) were mixed together. For each additional 384-well plate, an additional 3.5 mL of 2×SPA buffer w/o EDTA, 2.1 mL of H$_2$O, and 1.4 mL of Ysi His-tag SPA beads were mixed together.

E. Procedure

Appropriate dilutions of each compound were prepared and pipetted into the appropriate wells of a multiwell plate.

9.1 µL of [$^3$H] EC was added to each well of column 2-23 of the multiwell plate.

5 µl of diluted LXRα lysate was added to each well of column 2-23 on odd rows of the multiwell plate.

5 µL of diluted LXRβ lysate was added to each well of column 2-23 on even rows of the multiwell plate.

17.5 µL of SPA bead solution was added to each well of column 2-23 of the multiwell plate.

The plates were covered with clear sealer and placed in an incubator at ambient temperature for 1 hour.

After incubation plates were analyzed using a luminescent plate reader (MicroBeta, Wallac) using the program n ABASE 3H_384DPM. The setting for n ABASE 3H_384DPM was:

Counting Mode: DPM
Sample Type: SPA
ParaLux Mode: low background
Count time: 30 sec.

Assays for LXR α and LXR β were performed in the identical manner. The determined Ki represents the average of at least two independent dose response experiments. The binding affinity for each compound may be determined by non-linear regression analysis using the one site competition formula to determine the IC$_{50}$ where:

$$Y = \text{Bottom} + \frac{(\text{Top} - \text{Bottom})}{(1 + 10^{X - \log IC50})}$$

The Ki is than calculated using the Cheng and Prusoff equation where:

Ki=IC$_{50}$/(1+[Concentration of Ligand]/Kd of Ligand)

For this assay, typically the Concentration of Ligand=50 nM and the Kd of EC for the receptor is 200 nM as determined by saturation binding.

The compounds of the invention demonstrated the ability to bind to LXRα and/or LXRβ when tested in this assay.

EXAMPLE 15

Co-Transfection Assay

To measure the ability of compounds to activate or inhibit the transcriptional activity of LXR in a cell based assay, the co-transfection assay was used. It has been shown that LXR functions as a heterodimer with RXR. For the co-transfection assay, expression plasmids for LXR and RXR are introduced via transient transfection into mammalian cells along with a luciferase reporter plasmid that contains one copy of a DNA sequence that is bound by LXR-RXR heterodimers (LXRE; Willy, P. et al. 1995). Treatment of transfected cells with an LXR agonist increases the transcriptional activity of LXR, which is measured by an increase in luciferase activity. Similarly, LXR antagonist activity can be measured by determining the ability of a compound to competitively inhibit the activity of a LXR agonist.

A. Required Materials

1. CV-1 African Green Monkey Kidney Cells
2. Co-transfection expression plasmids, comprising full-length LXR α (pCMX-hLXR α), LXR β (pCMX-hLXR β), or RXR α (pCMX-RXR), reporter plasmid (LXREx1-Tk-Luciferase), and control (pCMX-Galactosidase expression vector) (Willey et al. Genes & Development 9 1033-1045 (1995)).
3. Transfection reagent such as FuGENE6 (Roche).
4. 1×Cell lysis buffer (1% Triton X 100 (JT Baker X200-07), 10% Glycerol (JT Baker M778-07), 5 mM Ditritoreitol (Quantum Bioprobe DTT03; add fresh before lysing), 1 mM EGTA (Ethylene Glycol-bis (B-Amino ethyl ether)-N,N,N',N'-Tetracetic Acid) (Sigma E-4378), 25 mM Tricine (ICN 807420) pH 7.8)

5. 1×Luciferase assay buffer (pH at 7.8) (0.73 mM ATP, 22.3 mM Tricine, 0.11 mM EDTA, 33.3 mM DTT)

6. 1×Luciferrin/CoA (11 mM Luciferin, 3.05 mM Coenzyme A, 10 mM HEPES)

Preparation of Screening Reagents

CV-1 cells were prepared 24 hours prior to the experiment by plating them into T-175 flasks or 500 cm² dishes in order to achieve 70-80% confluency on the day of the transfection. The number of cells to be transfected was determined by the number of plates to be screened. Each 384 well plate requires 1.92×106 cells or 5000 cells per well. DNA Transfection Reagent was prepared by mixing the required plasmid DNAs with a cationic lipid transfection reagent FuGENE6 (Roche) by following the instructions provided with the reagents. Optimal DNA amounts were determined empirically per cell line and size of vessel to be transfected. 10-12 mL of media was added to the DNA Transfection Reagent and this mixture was added to the cells after aspirating media from the T175 cm² flask. Cells were then incubated at least 5 hours at 37° C. to prepare screening cells.

Luciferase assay reagent was prepared by combining before use (per 10 mL):

10 mL 1×Luciferase assay buffer
0.54 mL of 1×Luciferrin/CoA
0.54 mL of 0.2 M Magnesium sulfate Procedure Assay plates were prepared by dispensing 5 μL of compound per well of a 384 well plate to achieve final compound concentration of 10 μM and no more than 1% DMSO. Media was removed from the screening cells, the cells trypsinized, harvested cells by centrifugation, counted, and plated at a density of approximately 5000 cells per well in the 384 well assay plate prepared above in a volume of about 45 μL. Assay plates containing both compounds and screening cells (50 μL in total volume) were incubated for 20 hours at 37° C.

After incubation with compounds, media was removed from the cells and lysis buffer (30 μuL/well) added. After 30 minutes at ambient temperature, luciferase assay buffer (30 μL/well) was added and the assay plates read on a luminometer (PE Biosystems Northstar reader with on-board injectors, or equivalent). Plates were read immediately after addition of luciferase assay buffer.

The LXR/LXRE co-transfection assay can be used to establish the $EC_{50}/IC_{50}$ values for potency and percent activity or inhibition for efficacy. Efficacy defines the activity of a compound relative to a high control ((N-(3-((4-fluorophenyl)-(naphthalene-2-sulfonyl)amino)propyl)-2,2-dimethylpropionamide)) or a low control (DMSO/vehicle). The dose response curves are generated from an 8 point curve with concentrations differing by ½ LOG units. Each point represents the average of 4 wells of data from a 384 well plate.

The data from this assay is fitted to the following equation, from the $EC_{50}$ value may be solved:

$$Y = \text{Bottom} + (\text{Top} - \text{Bottom})/(1 + 10^{((logEC50-X*HillSlope))})$$

The $EC_{50}/IC_{50}$ is therefore defined as the concentration at which an agonist or antagonist elicits a response that is half way between the Top (maximum) and Bottom (baseline) values. The $EC_{50}/IC_{50}$ values represented are the averages of at least 3 independent experiments. The determination of the relative efficacy or % control for an agonist is by comparison to the maximum response achieved by ((N-(3-((4-fluorophenyl)-(naphthalene-2-sulfonyl)-amino)propyl)-2,2-dimethylpropionamide) that is measured individually in each dose response experiment.

For the antagonist assay, a LXR agonist can be added to each well of a 384 well plate to elicit a response. The % inhibition for each antagonist is therefore a measurement of the inhibition of the activity of the agonist. In this example, 100% inhibition would indicate that the activity of a specific concentration of LXR agonist has been reduced to baseline levels, defined as the activity of the assay in the presence of DMSO only.

Compounds of the invention, when tested in this assay, demonstrated the ability to modulate the activity of LXR α and/or LXR β, as illustrated in the following Table:

| Compound Name | Ki(a) | Ki(b) | $EC_{50}$(a) | % Eff(a) | $EC_{50}$(b) | % Eff(b) |
| --- | --- | --- | --- | --- | --- | --- |
| 2-(2,4-dimethylbenzyl)-3-m-tolyl-2H-isoquinolin-1-one | F | G | B | Y | A | Y |
| 2-benzyl-3-m-tolyl-2H-isoquinolin-1-one | E | E | A | Z | A | Y |
| 2-(2,4-dimethylbenzyl)-3-thiophen-3-yl-2H-isoquinolin-1-one | E | F | A | Y | A | Y |
| 2-(2,4-dimethylbenzyl)-3-(3-hydroxy-3-methylbut-1-ynyl)-2H-isoquinolin-1-one | E | E | A | Y | A | Y |
| 2-(2,4-dimethylbenzyl)-3-(4-phenoxyphenyl)-2H-isoquinolin-1-one | G | G | C | X | C | X |
| 8-methyl-2-(4-methylbenzyl)-3-(4-phenoxyphenyl)-2H-isoquinolin-1-one | G | G | C | Y | C | Y |
| 8-chloro-2-(2,4-difluorobenzyl)-3-(4-phenoxyphenyl)-2H-isoquinolin-1-one | G | G | C | X | C | X |
| 8-chloro-2-(2,4-difluorobenzyl)-3-[5-(4-methanesulfonylphenyl)thiophen-2-yl]-2H-isoquinolin-1-one | G | G | C | Y | D | X |

-continued

| Compound Name | Ki(a) | Ki(b) | EC$_{50}$(a) | % Eff(a) | EC$_{50}$(b) | % Eff(b) |
|---|---|---|---|---|---|---|
| 8-chloro-2-(2,4-difluorobenzyl)-3-[4-(pyrazin-2-yloxy)phenyl]-2H-isoquinolin-1-one | G | G | D | X | C | X |
| 8-chloro-3-[4-(3-chloro-4-ethoxyphenyl)thiophen-2-yl]-2-(2,4-difluorobenzyl)-2H-isoquinolin-1-one | E | F | C | Y | C | X |
| 3-[4-(3,5-bis-trifluoromethylphenyl)furan-2-yl]-8-chloro-2-(2,4-difluorobenzyl)-2H-isoquinolin-1-one | F | G | C | Y | C | X |
| 8-chloro-2-cyclohexylmethyl-3-(4-phenoxyphenyl)-2H-isoquinolin-1-one | G | G | C | Y | B | X |
| 8-chloro-3-(4-phenoxyphenyl)-2-thiophen-2-ylmethyl-2H-isoquinolin-1-one | G | G | C | Y | B | X |
| 3-[4-(4-amino-3-trifluoromethylphenyl)furan-2-yl]-8-chloro-2-(2,4-difluorobenzyl)-2H-isoquinolin-1-one | G | G | D | X | C | X |

The Table above provides in vitro data for representative compounds whose synthesis is described in the Examples. Data is provided for LXR α and LXR β receptors. Average EC$_{50}$ values for agonism with respect to LXR α (EC$_{50}$(a)) or LXR β (EC$_{50}$(b)) in the cotransfection assay is provided as follows: A=greater than 0.5 µM, B=greater than 0.15 µM and less than 0.5 µM, C=greater than 0.01 µM and less than 0.15 µM, and D=less than 0.01 µM. Average percent efficacy with respect to LXR α (% Eff(a)), or LXR β (% Eff(b)), relative to control (N-(3-((4-fluoro-phen-yl)-(naphthalene-2-sulfo-nyl)-amino)propyl)-2,2-dimethylpropionamide) in the co-transfection assay is provided as follows: X=greater than 90% efficacy, Y=greater than 40% efficacy and less than 90% efficacy, Z=less than 40% efficacy. Average Ki values with respect to LXR α (Ki(a)), and LXR β (Ki(b), based on data from the SPA assay are provided as follows: E=greater than 0.5 µM, F=greater than 0.15 µM and less than 0.5 µM, G=greater than 0.01 µM and less than 0.15 µM, H=less than 0.01 µM.

EXAMPLE 16

In Vivo Studies

In order to evaluate direct regulation of key target genes by the compounds of the invention, animals are administered a single oral dose of the test compound and tissues collected at six or fifteen hours after dose. Male C57BL/6 mice (n=8) are dosed by oral gavage with vehicle or compound. At six and fifteen hours after the dose, animals are bled via the retro orbital sinus for plasma collection. Animals are then euthanized and tissues, such as liver and intestinal mucosa are collected and snap frozen for further analysis. Plasma is analyzed for a lipid parameters, such as total cholesterol, HDL cholesterol and triglyceride levels. RNA is extracted for frozen tissues and can be analyzed by quantitative real time PCR for regulation of key target genes. To identify specificity of target gene regulation by LXR subtypes, LXR deficient mice (LXRα-/- or LXRβ-/-) and C57BL/6 wild-type controls are used in this same protocol.

Plasma Lipid Evaluation

To compare the effects of compounds on plasma cholesterol and triglycerides, animals are dosed with compound for one week and plasma lipid levels are monitored throughout the study. Male C57BL/6 mice (n=8) are dosed daily by oral gavage with vehicle or compound. Plasma samples are taken on day -1 (in order to group animals), day 1, 3, and 7. Samples are collected three hours after the daily dose. On day 7 of the study, following plasma collection, animals are euthanized and tissues, such as liver and intestinal mucosa are collected and snap frozen for further analysis. Plasma is analyzed for lipid parameters, such as total cholesterol, HDL cholesterol and triglyceride levels. RNA is extracted for frozen tissues and can be analyzed by quantitative real time PCR for regulation of key target genes. To identify specificity of target gene regulation by LXR subtypes, LXR deficient mice (LXRα-/- or LXRβ-/-) and C57BL/6 wild-type controls are used in this same protocol.

Cholesterol Absorption

Evaluation of compounds to inhibit cholesterol absorption is done via measurement of labeled cholesterol in feces. Male A129 mice (n=7) are dosed daily by oral gavage with vehicle or compound for 7 days. On day 7 of the study, animals are administered [$^{14}$C]-cholesterol and [$^{3}$H]-sitostanol by oral gavage. Animals are individually housed on wire racks for the next 24 hours in order to collect feces. Feces are then dried and ground to a fine powder. Labeled cholesterol and sitostanol are extracted from the feces and ratios of the two are counted on a liquid scintillation counter in order to evaluate the amount of cholesterol absorbed by the individual animal.

All of the U.S. patents, U.S. patent application publications, U.S. patent applications, foreign patents, foreign patent applications and non-patent publications referred to in this specification and/or listed in the Application Data Sheet, are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A compound of formula (I);

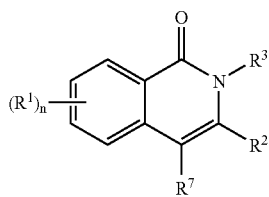

wherein:

n is 1 to 4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, —$R^6$, —$OR^4$—$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$S(O)_tR^4$ (where t is 0 to 2), and —$R^6S(O)_pN(R^4)_2$, (where p is 1 or 2);

$R^2$ is aryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

or $R^2$ is heteroaryl optionally substituted with one or more substituents selected from the group consisting of alkyl, alkenyl, cyano, nitro, halo, haloalkyl, haloalkenyl, optionally substituted aryl, optionally subtituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

$R^3$ is cycloalkylalkyl optionally substituted with one or more substituents selected from the group consisting of alkyl, alkenyl, cyano, nitro, halo, haloalkyl, haloalkenyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

or $R^3$ is aralkyl wherein the aryl group of the aralkyl substituent is substituted with one or more substituents selected from the group consisting of the alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

or $R^3$ is heteroarylalkyl wherein the heteroaryl group of the heteroarylakyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_1R^4$ (where t is 0 to 2), and —$R^6$—$S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted hetercyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ hydrogen or aralkyl;

as a single stereoisomer, a mixture of stereoisomers, or as a racemic mixture of stereoisomers; or as a solvate or polymorph; or as a pharmaceutically acceptable salt thereof;

with the following provisos:

(a) when $R^7$ is hydrogen, n is 1, $R^1$ is chloro, methyl, trifluoromethyl or methoxy, and $R^3$ is methyl, $R^2$ can not be unsubstituted furanyl or thiophenyl optionally substituted by methyl;

(b) when $R^7$ is hydrogen, n is 1 or 2, each $R^1$ is independently halo, trifluoromethyl, an alkyl group of 1 to 3 carbons or —$R^6$—$OR^4$ where $R^6$ is a direct bond and $R^4$ is an alkyl group of 1 to 3 carbons, and $R^3$ is an alkyl group of 1 to 3 carbons, $R^2$ can not be phenyl optionally substituted by halo, an alkyl group of 1 to 3 carbons or —$R^6$—$OR^4$ where $R^6$ is a direct bond and $R^4$ is an alkyl group of 1 to 4 carbons;

(c) when $R^7$ is hydrogen, n is 1, $R^1$ is halo, methyl or methoxy, and $R^3$ is methyl, $R^2$ can not be oxazole;

(d) $R^1$ is other than —$R^6$—$C(O)OR^4$ where $R^6$ is a direct bond and $R^4$ is alkyl of 1 to 3 carbons.

2. A compound of formula (I):

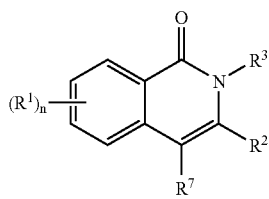

(I)

wherein:

n is 1 to 4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$S(O)_tR^4$ where t is 0 to 2), and —$R^6$—$S(O)_pN(R^4)_2$ (where p is 1 or 2), $R^2$ is heteroaryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)^tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R_6$—$S(O)_pN(R^4)_2$ (where p is 1 or 2);

$R^3$ is cycloalkylalkyl optionally substituted with one or more substituents selected from the group consisting of alkyl, alkenyl, cyano, nitro, halo, haloalkyl, haloalkenyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where p is 0 or 2), —$R^6$—$N(R^4)(S(O)_tR^4)$(where t is 0 to 2), —$R^6$—$S(O)_tR^4$ (where t is 0 to 2), and —$R^6$—$S(O)_pN(R^4)_2$ (where p is 1 or 2);

or $R^3$ is aralkyl wherein the aryl group of the aralkyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R_6$—$S(O)_pN(R^4)_2$ (where p is 1 or 2);

or $R^3$ is heteroarylalkyl wherein the heteroaryl group of the heteroarylakyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), and —$R^6$—$S(O)_tR^4$ (where t is 0 to 2), and —$R^6$—$S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen or aralkyl.

3. The compound of claim 2 wherein:

n is 1 to4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, —$R^6OR^4$, —$OR^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$S(O)_tR^4$ (where t is 0 to 2), and —$R_6$—$S(O)_pN(R^4)_2$ (where p is 1 or 2);

$R^2$ is heteroaryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R_6$—$S(O)_pN(R^4)_2$ (where p is 1 or 2);

$R^3$ is aralkyl wherein the aryl group of the aralkyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen or aralkyl.

4. The compound of claim 3 wherein:

n is 1 to 4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$S(O)_tR^4$ (where t is 0 to 2), and —$R^6$—$S(O)_pN(R^4)_2$ (where p is 1 or 2);

$R^2$ is heteroaryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

$R^3$ is benzyl optionally substituted with one or more substituents selected from the group consisting of alkyl, aryl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

$R^5$ is selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen.

5. The compound of claim 4 wherein:

n is 1 to 4;

each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;

$R^2$ is thiophenyl, benzothiophenyl, furanyl or benzofuranyl, each optionally substituted with one or more substituents selected from the group consisting of alkyl, cyano, nitro, halo, haloalkyl, optionally substituted aryl, optionally substituted aralkyl, optionally substituted heteroaryl, optionally substituted heteroarylalkyl, —$R^6$—$OR^4$, —$R^6$—$N(R^4)_2$, —$R^6$—$C(O)OR^4$, and —$R^6$—$C(O)N(R^4)_2$;

$R^3$ is benzyl optionally substituted with one or more substituents selected from the group consisting of alkyl, aryl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^6$ is a direct bond or a straight or branched alkylene chain; and $R^7$ is hydrogen.

6. The compound of claim 5 wherein:

n is 1 to 4;

each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;

$R^2$ is thiophenyl, benzothiophenyl, furanyl or benzofuranyl, each of which are optionally substituted with one or more substituents independently selected from the group consisting of halo, —$R^6$—$OR^4$, optionally substituted phenyl and optionally substituted pyridinyl;

$R^3$ is benzyl optionally substituted with one or more substituents selected from the group consisting of alkyl, aryl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, haloalkyl, aryl, and aralkyl;

each $R^6$ is a direct bond or a straight or branched alkylene chain; and $R^7$ is hydrogen.

7. The compound of claim 6 wherein:

n is 1 to 4;

each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;

$R^2$ is thiophenyl, benzothiophenyl, furanyl or benzofuranyl, each of which are optionally substituted with one or more substituents independently selected from the group consisting of halo and —$R^6$—$OR^4$;

$R^3$ is benzyl optionally substituted with one or more substituents selected from the group consisting of alkyl, aryl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, haloalkyl, aryl, and aralkyl;

each $R^6$ is a direct bond or a straight or branched alkylene chain; and $R^7$ is hydrogen.

8. The compound of claim 7 selected from the group consisting of the following:

2-benzyl-3-thiophen-2-yl-2H-isoquinolin-1-one;

2-benzyl-3-furan-3-yl-2H-isoquinolin-1-one;

2-(2,4-dimethylbenzyl)-3-thiophen-3-yl-2H-isoquinolin-1-one;

2-(2,4-dimethylbenzyl)-3-furan-2-yl-2H-isoquinolin-1-one;

2-benzyl-3-thiophen-3-yl-2H-isoquinolin-1-one;

2-(2,4-dimethylbenzyl)-3-thiophen-2-yl-2H-isoquinolin-1-one;

3-benzo[b]thiophen-2-yl-2-(4-methylbenzyl)-2H-isoquinolin-1-one;

3-benzofuran-2-yl-2-(4-methylbenzyl)-2H-isoquinolin-1-one;

3-benzofuran-2-yl-2-(2,4-dimethylbenzyl)-2H-isoquinolin-1-one;

3-benzo[b]thiophen-2-yl-2-(2,4-dimethylbenzyl)-2H-isoquinolin-1-one; and 3-(5-bromothiophen-2-yl)-8-chloro-2-(2,4-difluorobenzyl)-2H-isoquinolin-1-one.

9. The compound of claim 6 wherein:

n is 1 to 4;

each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;

$R^2$ is thiophenyl or furanyl, each of which is substituted with phenyl or pyridinyl, where the phenyl and the pyridinyl are each optionally substituted with one or more substituents selected from the group consisting of alkyl, halo, haloalkyl, cyano, nitro, —$R^6$—$OR^4$, —$R^6$—$N(R^4)_2$, —$R^6$—$C(O)OR^4$, —$R^6$—$C(O)N(R^4)_2$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 to 2);

$R^3$ is benzyl optionally substituted with one or more substituents selected from the group consisting of alkyl, aryl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, haloalkyl, aryl, and aralkyl;

each $R^6$ is a direct bond or a straight or branched alkylene chain; and $R^7$ is hydrogen.

10. The compound of claim 9 selected from the group consisting of the following:

8-chloro-2-(2,4-difluorobenzyl)-3-[5-(3,4-dimethoxyphenyl)thiophen-2-yl]-2H-isoquinolin-1-one;

3-[5-(3,5-bis-trifluoromethylphenyl)thiophen-2-yl]-8-chloro-2-(2,4-difluorobenzyl)-2H-isoquinolin-1-one;

8-chloro-2-(2,4-difluorobenzyl)-3-[5-(4-methanesulfonylphenyl)thiophen-2-yl]-2H-isoquinolin-1-one;

8-chloro-3-[5-(3-chloro-4-ethoxyphenyl)thiophen-2-yl]-2-(2,4-difluorobenzyl)-2H-isoquinolin-1-one;

8-chloro-3-[5-(3-chloro-4-ethoxyphenyl)furan-2-yl]-2-(2,4-difluorobenzyl)-2H-isoquinolin-1-one;

3-[5-(3,5-bis-trifluoromethylphenyl)furan-2-yl]-8-chloro-2-(2,4-difluorobenzyl)-2H-isoquinolin-1-one;

8-chloro-2-(2,4-difluorobenzyl)-3-[5-(4-methanesulfonylphenyl)furan-2-yl]-2H-isoquinolin-1-one;

8-chloro-3-[4-(3-chloro-4-ethoxyphenyl)thiophen-2-yl]-2-(2,4-difluorobenzyl)-2H-isoquinolin-1-one;

3-[4-(3,5-bis-trifluoromethylphenyl)thiophen-2-yl]-8-chloro-2-(2,4-difluorobenzyl)-2H-isoquinolin-1-one;

8-chloro-2-(2,4-difluorobenzyl)-3-[4-(4-methanesulfonylphenyl)thiophen-2-yl]-2H-isoquinolin-1-one;

3-[4-(4-amino-3-trifluoromethylphenyl)thiophen-2-yl]-8-chloro-2-(2,4-difluorobenzyl)-2H-isoquinolin-1-one;

3-[4-(4-amino-3-chloro-phenyl)thiophen-2-yl]-8-chloro-2-(2,4-difluorobenzyl)-2H-isoquinolin-1-one;

8-chloro-2-(2,4-difluorobenzyl)-3-[4-(4-ethoxy-3-trifluoromethylphenyl)thiophen-2-yl]-2H-isoquinolin-1-one;

8-chloro-2-(2,4-difluorobenzyl)-3-[5-(4-ethoxy-3-trifluoromethylphenyl)thiophen-2-yl]-2H-isoquinolin-1-one;

3-[5-(4-amino-3-trifluoromethylphenyl)thiophen-2-yl]-8-chloro-2-(2,4-difluorobenzyl)-2H-isoquinolin-1-one;

3-[5-(4-amino-3-chloro-phenyl)thiophen-2-yl]-8-chloro-2-(2,4-difluorobenzyl)-2H-isoquinolin-1-one;

8-chloro-3-[4-(3-chloro-4-diethylamino-phenyl)thiophen-2-yl]-2-(2,4-difluorobenzyl)-2H-isoquinolin-1-one;

8-chloro-3-[4-(3-chloro-4-ethylamino-phenyl)thiophen-2-yl]-2-(2,4-difluorobenzyl)-2H-isoquinolin-1-one;

8-chloro-3-[4-(3-chloro-4-ethoxyphenyl)furan-2-yl]-2-(2,4-difluorobenzyl)-2H-isoquinolin-1-one;

3-[4-(3,5-bis-trifluoromethylphenyl)furan-2-yl]-8-chloro-2-(2,4-difluorobenzyl)-2H-isoquinolin-1-one;

8-chloro-2-(2,4-difluorobenzyl)-3-[5-(4-ethylamino-3-trifluoromethylphenyl)thiophen-2-yl]-2H-isoquinolin-1-one;

8-chloro-3-[5-(3-trifluoromethyl-4-(bis-methanesulfonylamino)-phenyl)thiophen-2-yl]-2-(2,4-difluorobenzyl)-2H-isoquinolin-1-one;

8-chloro-2-(2,4-difluorobenzyl)-3-[4-(4-methanesulfonylphenyl)furan-2-yl]-2H-isoquinolin-1-one;

8-chloro-2-(2,4-difluorobenzyl)-3-[5-(3-ethanesulfonyl-5-trifluoromethylphenyl)thiophen-2-yl]-2H-isoquinolin-1-one;

8-chloro-2-(2,4-difluorobenzyl)-3-[4-(3-ethanesulfonyl-5-trifluoromethylphenyl)furan-2-yl]-2H-isoquinolin-1-one;

3-[4-(4-amino-3-trifluoromethylphenyl)furan-2-yl]-8-chloro-2-(2,4-difluorobenzyl)-2H-isoquinolin-1-one;

8-chloro-2-(2,4-difluorobenzyl)-3-[5-(3-ethylsulfanyl-5-trifluoromethylphenyl)furan-2-yl]-2H-isoquinolin-1-one;

8-chloro-2-(2,4-difluorobenzyl)-3-[5-(3-ethanesulfonyl-5-trifluoromethylphenyl)furan-2-yl]-2H-isoquinolin-1-one;

8-chloro-2-(2,4-difluorobenzyl)-3-[4-(4-ethylamino-3-trifluoromethylphenyl)furan-2-yl]-2H-isoquinolin-1-one;

8-chloro-2-(2,4-difluorobenzyl)-3-[5-(6-ethoxy-pyridin-3-yl)-thiophen-2-yl]-2H-isoquinolin-1-one; and 5-{5-[8-chloro-2-(2,4-difluorobenzyl)-1-oxo-1,2-dihydro-isoquinolin-3-yl]-thiophen-2-yl}-2-ethoxy-nicotinonitrile.

11. The compound of claim 1 wherein:

n is 1 to 4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$S(O)_tR^4$ (where t is 0 to 2), and —$R^6$—$S(O)_pN(R^4)_2$ (where p is 1 or 2);

$R^2$ is aryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R_6$—$S(O)_pN(R^4)_2$ (where p is 1 or 2);

$R^3$ cycloalkylalkyl optionally substituted with one or more substituents selected from the group consisting of alkyl, alkenyl, cyano, nitro, halo, haloalkyl, haloalkenyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

or $R^3$ is aralkyl wherein the aryl group of the aralkyl substituent is substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

or $R^3$ is heteroarylalkyl wherein the heteroaryl group of the heteroarylakyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen or aralkyl.

12. The compound of claim 11 wherein:

n is 1 to 4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$S(O)_tR^4$ (where t is 0 to 2), and —$R^6$—$S(O)_pN(R^4)_2$ (where p is 1 or 2);

$R^2$ is aryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

$R^3$ is aralkyl wherein the aryl group of the aralkyl substituent is substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen or aralkyl.

13. The compound of claim 12 wherein:

n is 1 to 4;

each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;

$R^2$ is phenyl optionally substituted with one or more substituents selected from the group consisting of alkyl, cyano, nitro, halo, haloalkyl, optionally substituted aryl, optionally substituted aralkyl, optionally substituted heteroaryl, optionally substituted heteroarylalkyl, —$R^6$—$OR^4$, —$R^6$—$N(R^4)_2$, —$R6$—$C(O)OR^4$, —$R^6$—$C(O)N(R^4)_2$, and —$R^6$—$N(R^4)C(O)R^4$;

$R^3$ is benzyl substituted with one or more substituents selected from the group consisting of alkyl, aryl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;

each $R^4$ is independently selected from the group consisting of hydrogen, alkyl, alkenyl, haloalkyl, hydroxyalkyl, cycloalkyl, cycloalkylalkyl, aryl, and aralkyl;

each $R^6$ is a direct bond or a straight or branched alkylene chain; and $R^7$ is hydrogen.

14. The compound of claim 13 wherein:

n is 1;

$R^1$ is alkyl or halo;

$R^2$ is phenyl optionally substituted with one or more substituents selected from the group consisting of alkyl, optionally substituted aryl and optionally substituted aralkyl; and $R^3$ is benzyl substituted with one or more substituents selected from the group consisting of alkyl, halo and aryl.

15. A compound selected from the group consisting of the following:

2-biphenyl-4-ylmethyl-3-m-tolyl-2H-isoquinolin-1-one;

2-(2,4-dimethylbenzyl)-3-m-tolyl-2H-isoquinolin-1-one;

2-benzyl-3-m-tolyl-2H-isoquinolin-1-one;

2-(2,4-dimethylbenzyl)-3-(3,5-dimethylphenyl)-2H-isoquinolin-1-one;

2-(2,4-dimethylbenzyl)-3-phenyl-2H-isoquinolin-1-one;

5-chloro-2-(2,4-dimethylbenzyl)-3-m-tolyl-2H-isoquinolin-1-one;

5-chloro-2-(4-methylbenzyl)-3-m-tolyl-2H-isoquinolin-1-one;

5-chloro-2-(2,4-dimethylbenzyl)-3-phenyl-2H-isoquinolin-1-one;

5-chloro-2-(4-methylbenzyl)-3-phenyl-2H-isoquinolin-1-one;
8-chloro-2-(2,4-dimethylbenzyl)-3-phenyl-2H-isoquinolin-1-one;
8-chloro-2-(2,4-dimethylbenzyl)-3-m-tolyl-2H-isoquinolin-1-one;
2-benzyl-8-chloro-3-m-tolyl-2H-isoquinolin-1-one;
2-benzyl-8-chloro-3-phenyl-2H-isoquinolin-1-one;
2-benzyl-8-methyl-3-m-tolyl-2H-isoquinolin-1-one;
8-methyl-2-(4-methylbenzyl)-3-m-tolyl-2H-isoquinolin-1-one;
2-(2,4-dimethylbenzyl)-8-methyl-3-m-tolyl-2H-isoquinolin-1-one;
2-benzyl-8-methyl-3-phenyl-2H-isoquinolin-1-one;
8-methyl-2-(4-methylbenzyl)-3-phenyl-2H-isoquinolin-1-one;
2-(2,4-dimethylbenzyl)-8-methyl-3-phenyl-2H-isoquinolin-1-one;
2-(2,4-dimethylbenzyl)-7-methyl-3-phenyl-2H-isoquinolin-1-one;
2-(2,4-dimethylbenzyl)-7-methyl-3-m-tolyl-2H-isoquinolin-1-one;
7-methyl-2-(4-methylbenzyl)-3-phenyl-2H-isoquinolin-1-one;
7-methyl-2-(4-methylbenzyl)-3-m-tolyl-2H-isoquinolin-1-one; and
7-chloro-2-(2,4-dimethylbenzyl)-3-m-tolyl-2H-isoquinolin-1-one;
2-benzyl-7-methyl-3-m-tolyl-2H-isoquinolin-1-one;
2-benzyl-7-methyl-3-phenyl-2H-isoquinolin-1-one;
2-benzyl-6-methyl-3-m-tolyl-2H-isoquinolin-1-one;
2-benzyl-6-methyl-3-phenyl-2H-isoquinolin-1-one;
2-(2,4-dimethylbenzyl)-6-methyl-3-phenyl-2H-isoquinolin-1-one;
6-methyl-2-(4-methylbenzyl)-3-m-tolyl-2H-isoquinolin-1-one;
6-methyl-2-(4-methylbenzyl)-3-phenyl-2H-isoquinolin-1-one;
7-chloro-2-(2,4-dimethylbenzyl)-3-phenyl-2H-isoquinolin-1-one;
2-(4-methylbenzyl)-3-phenyl-2H-isoquinolin-1-one;
2-benzyl-3-phenyl-2H-isoquinolin-1-one;
3-(4-benzylphenyl)-2-(2,4-dimethylbenzyl)-8-methyl-2H-isoquinolin-1-one;
8-chloro-2-(2,4-difluorobenzyl)-3-(4'-methanesulfonyl-biphenyl-3-yl)-2H-isoquinolin-1-one;
8-chloro-2-(2,4-difluorobenzyl)-3-(3'-ethanesulfonyl-5'-trifluoromethyl-biphenyl-3-yl)-2H-isoquinolin-1-one;
8-chloro-2-(2,4-difluorobenzyl)-3-[3-(6-ethoxypyridin-3-yl)-phenyl]-2H-isoquinolin-1-one;
5-{3-[8-chloro-2-(2,4-difluorobenzyl)-1-oxo-1,2-dihydroisoquinolin-3-yl]-phenyl}-2-ethoxy-nicotinonitrile;
3-(3',5'-bis-trifluoromethylbiphenyl-3-yl)-8-chloro-2-(2,4-difluorobenzyl)-2H-isoquinolin-1-one; and
8-chloro-3-(3'-chloro-4'-ethoxybiphenyl-3-yl)-2-(2,4-difluorobenzyl)-2H-isoquinolin-1-one.

16. The compound of claim 12 wherein:
n is 0 to 4;
each $R^1$ is independently selected from the group consisting of alkyl, halo, haloalkyl, cyano, nitro, —$R^6OR^4$, —$R^6$—N($R^4$)$_2$, —$R^6$—C(O)O$R^4$, and —$R^6$—C(O)N($R^4$)$_2$;
$R^2$ is phenyl optionally substituted with one or more substituents selected from the group consisting of alkyl, —$R^6$—O$R^4$, and —$R^6$—S(O)$_t R^4$ (where t is 0 to 2);
$R^3$ is benzyl substituted with one or more substituents selected from the group consisting of alkyl, aryl, aralkyl, cyano, nitro, halo, haloalkyl, cycloalkyl, heterocyclyl, —$R^6$—O$R^4$, —$R^6$—N($R^4$)$_2$, —$R^6$—C(O)O$R^4$, —$R^6$—C(O)N($R^4$)$_2$, —$R^6$—N($R^4$)C(O)$R^4$, —$R^6$—N($R^4$)C(O)O$R^5$, —$R^6$—S(O)$_t R^4$ (where t is 0 to 2), and —$R^6$—S(O)$_p$N($R^4$)$_2$ (where p is 1 or 2);
each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;
each $R^5$ is independently selected from the group consisting of hydrogen, alkyl, alkenyl, haloalkyl, hydroxyalkyl, cycloalkyl, cycloalkylalkyl, and aralkyl;
each $R^6$ is a direct bond or a straight or branched alkylene chain; and
$R^7$ is hydrogen or aralkyl.

17. The compound of claim 16 wherein:
n is 0 to 4;
each $R^1$ is independently selected from the group consisting of alkyl, halo, haloalkyl, cyano, nitro, —$R^6$—O$R^4$, —$R^6$—N($R^4$)$_2$, —$R^6$—C(O)O$R^4$, and —$R^6$—C(O)N($R^4$)$_2$;
$R^2$ is phenyl optionally substituted with one or more substituents selected from the group consisting of alkyl, —$R^6$—O$R^4$, and —$R^6$—S(O)$_t R^4$ (where t is 0 to 2);
$R^3$ is benzyl substituted with one or more substituents selected from the group consisting of alkyl, halo, and haloalkyl;
each $R^4$ is independently selected from the group consisting of hydrogen, alkyl, optionally substituted aryl, optionally substituted aralkyl, optionally substituted heterocyclyl and optionally substituted heteroaryl;
each $R^6$ is a direct bond; and
$R^7$ is hydrogen or aralkyl.

18. A compound selected from the group consisting of the following:
2-benzyl-3-(4-hydroxy-3,5-dimethylphenyl)-2H-isoquinolin-1-one;
2-(2,4-dimethylbenzyl)-3-(4-hydroxy-3,5-dimethylphenyl)-2H-isoquinolin-1-one;
2-(2,4-dimethylbenzyl)-3-(4-methoxyphenyl)-2H-isoquinolin-1-one;
2-benzyl-3-(4-hydroxyphenyl)-2H-isoquinolin-1-one;
2-(2,4-dimethylbenzyl)-3-(4-hydroxyphenyl)-2H-isoquinolin-1-one;
2-(2,4-dimethylbenzyl)-3-(4-hydroxy-3-methoxyphenyl)-2H-isoquinolin-1-one;
2-(2,4-dimethylbenzyl)-3-[3-methyl-4-(tetrahydropyran-2-yloxy)phenyl]-2H-isoquinolin-1-one;
2-(2,4-dimethylbenzyl)-3-(4-hydroxy-3-methylphenyl)-2H-isoquinolin-1-one;
2-(4-methylbenzyl)-3-(4-phenoxyphenyl)-2H-isoquinolin-1-one;
2-(2,4-dimethylbenzyl)-3-(4-phenoxyphenyl)-2H-isoquinolin-1-one;
2-(2,4-dimethylbenzyl)-3-(4-methylsulfanylphenyl)-2H-isoquinolin-1-one;
2-(4-methyl-benzyl)-3-(4-methylsulfanylphenyl)-2H-isoquinolin-1-one;
2-(2,4-dimethylbenzyl)-3-(3-methyl-4-phenoxyphenyl)-2H-isoquinolin-1-one;
2-benzyl-3-(4-phenoxyphenyl)-2H-isoquinolin-1-one;
5-chloro-2-(2,4-dimethylbenzyl)-3-(4-phenoxyphenyl)-2H-isoquinolin-1-one;
5-chloro-2-(4-methylbenzyl)-3-(4-phenoxyphenyl)-2H-isoquinolin-1-one;

2-(2,4-dimethylbenzyl)-5-fluoro-3-(4-phenoxyphenyl)-2H-isoquinolin-1-one;
2-benzyl-5-fluoro-3-(4-phenoxyphenyl)-2H-isoquinolin-1-one;
8-chloro-2-(2,4-dimethylbenzyl)-3-(4-phenoxyphenyl)-2H-isoquinolin-1-one;
2-benzyl-8-chloro-3-(4-phenoxyphenyl)-2H-isoquinolin-1-one;
2-benzyl-8-methyl-3-(4-phenoxyphenyl)-2H-isoquinolin-1-one;
8-methyl-2-(4-methylbenzyl)-3-(4-phenoxyphenyl)-2H-isoquinolin-1-one;
2-(2,4-dimethylbenzyl)-8-methyl-3-(4-phenoxyphenyl)-2H-isoquinolin-1-one;
2-(2,4-dimethylbenzyl)-7-methyl-3-(4-phenoxyphenyl)-2H-isoquinolin-1-one;
7-methyl-2-(4-methylbenzyl)-3-(4-phenoxyphenyl)-2H-isoquinolin-1-one;
2-benzyl-7-methyl-3-(4-phenoxyphenyl)-2H-isoquinolin-1-one;
2-benzyl-6-methyl-3-(4-phenoxyphenyl)-2H-isoquinolin-1-one;
2-(2,4-dimethylbenzyl)-6-methyl-3-(4-phenoxyphenyl)-2H-isoquinolin-1-one;
6-methyl-2-(4-methylbenzyl)-3-(4-phenoxyphenyl)-2H-isoquinolin-1-one;
7-chloro-2-(2,4-dimethylbenzyl)-3-(4-phenoxyphenyl)-2H-isoquinolin-1-one;
2-benzyl-7-chloro-3-(4-phenoxyphenyl)-2H-isoquinolin-1-one;
2-benzyl-6-chloro-3-(4-phenoxyphenyl)-2H-isoquinolin-1-one;
6-chloro-2-(2,4-dimethylbenzyl)-3-(4-phenoxyphenyl)-2H-isoquinolin-1-one;
2-benzyl-6,8-dimethyl-3-(4-phenoxyphenyl)-2H-isoquinolin-1-one;
2-(2,4-dimethylbenzyl)-6,8-dimethyl-3-(4-phenoxyphenyl)-2H-isoquinolin-1-one;
2-benzyl-5-methyl-3-(4-phenoxyphenyl)-2H-isoquinolin-1-one;
2-benzyl-5,6,7,8-tetramethyl-3-(4-phenoxyphenyl)-2H-isoquinolin-1-one;
2-(2,4-dimethylbenzyl)-5-methyl-3-(4-phenoxyphenyl)-2H-isoquinolin-1-one;
2-benzyl-8-methoxy-3-(4-phenoxyphenyl)-2H-isoquinolin-1-one;
2-(2,4-dimethylbenzyl)-8-fluoro-3-(4-phenoxyphenyl)-2H-isoquinolin-1-one;
8-chloro-2-(2,4-dichloro-benzyl)-3-(4-phenoxyphenyl)-2H-isoquinolin-1-one;
2-benzyl-8-fluoro-3-(4-phenoxyphenyl)-2H-isoquinolin-1-one;
2-(2,4-dimethylbenzyl)-3-(4-phenoxyphenyl)-8-trifluoromethyl-2H-isoquinolin-1-one;
2-(2,4-dimethylbenzyl)-8-methoxy-3-(4-phenoxyphenyl)-2H-isoquinolin-1-one;
8-chloro-2-(2,4-difluorobenzyl)-3-(4-phenoxyphenyl)-2H-isoquinolin-1-one;
7,8-dichloro-2-(2,4-dimethylbenzyl)-3-(4-phenoxyphenyl)-2H-isoquinolin-1-one;
8-chloro-2-(2,4-difluorobenzyl)-5-methyl-3-(4-phenoxyphenyl)-2H-isoquinolin-1-one;
6,7-dichloro-2-(2,4-difluorobenzyl)-3-(4-phenoxyphenyl)-2H-isoquinolin-1-one;
8-chloro-2-(2-chloro-4-fluoro-benzyl)-3-(4-phenoxyphenyl)-2H-isoquinolin-1-one;
5,6-dichloro-2-(2,4-difluorobenzyl)-3-(4-phenoxyphenyl)-2H-isoquinolin-1-one;
2-{4-[8-chloro-2-(2,4-difluorobenzyl)-1-oxo-1,2-dihydro-isoquinolin-3-yl]-phenoxy}-nicotinonitrile;
8-chloro-2-(2,4-difluorobenzyl)-3-(4-hydroxyphenyl)-2H-isoquinolin-1-one;
8-chloro-2-(2,4-difluorobenzyl)-3-[4-(pyrazin-2-yloxy)phenyl]-2H-isoquinolin-1-one;
2-{4-[2-(2,4-difluorobenzyl)-7-fluoro-1-oxo-1,2-dihydro-isoquinolin-3-yl]-phenoxy}-nicotinonitrile;
2-(2,4-difluorobenzyl)-7-fluoro-3-[4-(pyrazin-2-yloxy)phenyl]-2H-isoquinolin-1-one;
2-(2,4-difluorobenzyl)-7-fluoro-3-(4-phenoxyphenyl)-2H-isoquinolin-1-one;
2-(2,4-difluorobenzyl)-5-fluoro-3-[4-(pyrazin-2-yloxy)phenyl]-2H-isoquinolin-1-one;
2-{4-[2-(2,4-difluorobenzyl)-5-fluoro-1-oxo-1,2-dihydro-isoquinolin-3-yl]-phenoxy}-nicotinonitrile; and
2-(2,4-difluorobenzyl)-5-fluoro-3-(4-phenoxyphenyl)-2H-isoquinolin-1-one.

19. The compound of claim 12 wherein:
n is 0 or 1;
$R^1$ is alkyl or halo;
$R^2$ is phenyl optionally substituted with one or more substituents selected from the group consisting of cyano, halo, haloalkyl, $-R^6-OR^4$, $-R^6-N(R^4)_2$, $-R^6-C(O)OR^4$, and $-R^6-N(R^4)C(O)R^4$;
$R^3$ is benzyl substituted with one or more substituents selected from the group consisting of alkyl, aryl, aralkyl, cyano, nitro, halo, haloalkyl, cycloalkyl, heterocyclyl, $-R^6-OR^4$, $-R^6-N(R^4)_2$, $-R^6-C(O)OR^4$, $-R^6-C(O)N(R^4)_2$, $-R^6-N(R^4)C(O)OR^4$, $-R^6-N(R^4)C(O)OR^5$, $-R^6-S(O)_tR^4$ (where t is 0 to 2), and $-R^6-S(O)_pN(R^4)_2$ (where p is 1 or 2);
each $R^4$ is independently selected from the group consisting of hydrogen, alkyl, alkenyl, haloalkyl, hydroxyalkyl, cycloalkyl, cycloalkylalkyl, aryl, and aralkyl;
each $R^5$ is independently selected from the group consisting of hydrogen, alkyl, alkenyl, haloalkyl, hydroxyalkyl, cycloalkyl, cycloalkylalkyl, and aralkyl;
each $R^6$ is a direct bond or a straight or branched alkylene chain; and
$R^7$ is hydrogen or aralkyl.

20. The compound of claim 19 wherein:
n is 0 or 1;
$R^1$ is alkyl or halo;
$R^2$ is phenyl optionally substituted with one or more substituents selected from the group consisting of cyano, halo, haloalkyl, $-R^6-OR^4$, $-R^6-N(R^4)_2$, $-R^6-C(O)OR^4$, and $-R^6-N(R^4)C(O)R^4$;
$R^3$ is benzyl wherein the phenyl group is substituted with one or more alkyl substituents;
each $R^4$ is independently selected from the group consisting of hydrogen, alkyl, aryl, and aralkyl; and
each $R^6$ is a direct bond.

21. A compound selected from the group consisting of the following:
N-[4-(2-benzyl-1-oxo-1,2-dihydroisoquinolin-3-yl)phenyl]acetamide;
3-(4-aminophenyl)-2-(2,4-dimethylbenzyl)-2H-isoquinolin-1-one;
3-(3,5-bis-trifluoromethylphenyl)-2-(2,4-dimethylbenzyl)-2H-isoquinolin-1-one;
4-[2-(2,4-dimethylbenzyl)-1-oxo-1,2-dihydroisoquinolin-3-yl]benzoic acid methyl ester;
2-(2,4-dimethylbenzyl)-3-(4-methoxy-3-trifluoromethylphenyl)-2H-isoquinolin-1-one;

N-{4-[2-(2,4-dimethylbenzyl)-1-oxo-1,2-dihydroiso-
quinolin-3-yl]phenyl}-acetamide;
4-[2-(2,4-dimethylbenzyl)-1-oxo-1,2-dihydroisoquinolin-
3-yl]benzonitrile;
2-(2,4-dimethylbenzyl)-3-(3-trifluoromethylphenyl)-2H-
isoquinolin-1-one;
2-(4-methylbenzyl)-3-(3-trifluoromethylphenyl)-2H-iso-
quinolin-1-one;
2-benzyl-3-(3-trifluoromethylphenyl)-2H-isoquinolin-1-
one;
3-(4-bromophenyl)-2-(2,4-dimethylbenzyl)-2H-isoquino-
lin-1-one; and
3-(4-bromophenyl)-2-(4-methylbenzyl)-2H-isoquinolin-
1-one.

22. A compound of formula (I):

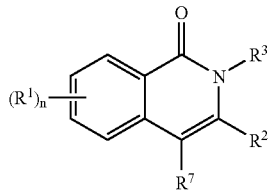

(I)

wherein:
n is 0 to 4;
each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, —$R^6$—$OR^4$, —$R^6$—$N(R^4)_2$, —$R^6$—$C(O)OR^4$, $R^6$—$C(O)N(R^4)_2$, —$R^6$—$N(R^4)C(O)R^4$, —$R^6$—$N(R^4)C(O)OR^5$, —$R^6$—$S(O)_tR^4$ (where t is 0 to 2), and —$R^6$—$S(O)_pN(R^4)_2$ (where p is 1 or 2);
$R^2$ is aryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—C(O)$OR^4$, —$R^6$—C(O)$N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), $R^6$—$S(O)_tR^4$ (where t is 0 to 2), and —$R^6$—$S(O)_pN(R^4)_2$ (where p is 1 or 2);
$R^3$ is alkyl or cycloalkylalkyl optionally substituted with one or more substituents selected from the group consisting of alkyl, alkenyl, cyano, nitro, halo, haloalkyl, haloalkenyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);
or $R^3$ is heteroarylalkyl wherein the heteroaryl group of the heteroarylakyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);
each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;
each $R^5$ is independently selected from the group consisting of hydrogen, alkyl, alkenyl, haloalkyl, hydroxyalkyl, cycloalkyl, cycloalkylalkyl, and aralkyl;
each $R^6$ is a direct bond or a straight or branched alkylene chain; and
$R^7$ is hydrogen or aralkyl.

23. The compound of claim 22 wherein:
n is 0 to 4;
each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;
$R^2$ is phenyl optionally substituted with one or more substituents selected from the group consisting of alkyl, cyano, nitro, halo, haloalkyl, optionally substituted aryl, optionally substituted aralkyl, optionally substituted heteroaryl, optionally substituted heteroarylalkyl, —$R^6$—$OR^4$, —$R^6$—$N(R^4)_2$, —$R^6$—$C(O)OR^4$, and —$R^6$—$C(O)N(R^4)_2$;
$R^3$ is cycloalkylalkyl optionally substituted with one or more substituents selected from the group consisting of alkyl, cyano, nitro, halo, haloalkyl, —$R^6$—$OR^4$, —$R^6$—$N(R^4)_2$, —$R^6$—$C(O)OR^4$, and —$R^6$—$C(O)N(R^4)_2$;
each $R^4$ is independently selected from the group consisting of hydrogen, alkyl, optionally substituted aryl, optionally substituted aralkyl, optionally substituted heterocyclyl and optionally substituted heteroaryl;
each $R^6$ is a direct bond or a straight or branched alkylene chain; and
$R^7$ is hydrogen or aralkyl.

24. The compound of claim 23 selected from the group consisting of the following:
8-chloro-2-cyclohexylmethyl-3-(4-phenoxyphenyl)-2H-
isoquinolin-1-one;

25. The compound of claim 22 wherein:
n is 0 to 4;
each $R^1$ is independently selected from the group consisting of alkyl, halo, haloalkyl, cyano, nitro, —$R^6$—$OR^4$, —$R^6$—$N(R^4)_2$, —$R^6$—$C(O)OR^4$, and —$R^6$—$C(O)N(R^4)_2$;
$R^2$ is phenyl optionally substituted with one or more substituents selected from the group consisting of alkyl, cyano, nitro, halo, haloalkyl, optionally substituted aryl, optionally substituted aralkyl, optionally substituted heteroaryl, optionally substituted heteroarylalkyl, —$R^6$—$OR^4$, —$R^6$—$N(R^4)_2$, —$R^6$—$C(O)OR^4$, and —$R^6$—$C(O)N(R^4)_2$;
or $R^3$ is heteroarylalkyl optionally substituted with one or more substituents selected from the group consisting of alkyl, halo, haloalkyl, —$R^6$—$OR^4$, —$R^6$—$N(R^4)_2$, —$R^6$—$C(O)OR^4$, and —$R^6$—$C(O)N(R^4)_2$;
each $R^4$ is independently selected from the group consisting of hydrogen, alkyl, optionally substituted aryl, optionally substituted aralkyl, optionally substituted heterocyclyl and optionally substituted heteroaryl;

each $R^6$ is a direct bond or a straight or branched alkylene chain; and $R^7$ is hydrogen or aralkyl.

26. The compound of claim 25 selected from the group consisting of:
    8-chloro-3-(4-phenoxyphenyl)-2-pyridin-3-ylmethyl-2H-isoquinolin-1-one-trifluoroacetic acid salt;
    8-chloro-2-(5-methyl-furan-2-ylmethyl)-3-(4-phenoxyphenyl)-2H-isoquinolin-1-one; and
    8-chloro-3-(4-phenoxyphenyl)-2-thiophen-2-ylmethyl-2H-isoquinolin-1-one.

27. A pharmaceutical composition comprising a pharmaceutically acceptable excipient and a compound of formula (I):

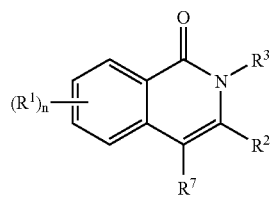

wherein:

n is 0 to 4;

each $R^1$ is independently selected from the group consisting of alkyl, alkenyl, alkynyl, halo, haloalkyl, haloalkenyl, cycloalkyl, cycloalkylalkyl, aryl, aralkyl, heterocyclyl, heterocyclylalkyl, cyano, nitro, —R—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —R—$S(O)_tR^4$ (where t is 0 to 2), —$R^6$—$S(O)_pN(R^4)_2$ (where p is 1 or 2);

$R^2$ is aryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —R—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —R6—$S(O)_pN(R^4)_2$ (where p is 1 to 2);

or $R^2$ is heteroaryl optionally substituted with one or more substituents selected from the group consisting of alkyl, alkenyl, cyano, nitro, halo, haloalkyl, haloalkenyl, optionally substituted aryl, optionally substituted aralkyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$R^6$—$N(R^4)C(O)R^4$, —$R^6$—$N(R^4)C(O)OR^5$, —$R^6$—$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$(where p is 1 or 2);

$R^3$ is cycloalkylalkyl optionally substituted with one or more substituents selected from the group consisting of alkyl, alkenyl, cyano, nitro, halo, haloalkyl, haloalkenyl, —$R^6$—$OR^4$, —$R^6$—$N(R^4)_2$, —$R^6$—$C(O)OR^4$, —$R^6$—$C(O)N(R^4)_2$, —$R^6$—$N(R^4)C(O)R^4$, —$R^6$—$N(R^4)C(O)OR^5$, —$R^6$—$N(S(O)_tR^4)_2$(where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

or $R^3$ is aralkyl wherein the aryl group of the aralkyl substituent is substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —$R^6$—$N(R^4)_2$, —$R^6$—$C(O)OR^4$, —$R^6$—$C(O)N(R^4)_2$, —$R^6$—$R^6$—$N(R^4)C(O)R^4$, —$R^6$—$N(R^4)C(O)OR^5$, —$R^6$—$N(S(O)_tR^4)_2$ (where t is 0 to 2), —R—$N(R^4)(S(O)_tR^4)$ (where t is 0 to 2), —$R^6$—$S(O)_tR^4$ (where t is 0 to 2), and —R6—$S(O)_pN(R^4)_2$ (where p is 1 or 2);

or $R^3$ is heteroarylalkyl wherein the heteroaryl group of the heteroarylakyl substituent is optionally substituted with one or more substituents selected from the group consisting of alkyl, alkenyl, aryl, aralkyl, cyano, nitro, halo, haloalkyl, haloalkenyl, optionally substituted cycloalkyl, optionally substituted cycloalkylalkyl, optionally substituted heterocyclyl, optionally substituted heterocyclylalkyl, optionally substituted heteroaryl, optionally substituted heteroarylalkyl, —$R^6$—$OR^4$, —R—$N(R^4)_2$, —$R^6$—$C(O)OR^4$, —$R^6$—$C(O)N(R^4)_2$, —$R^6$—$N(R^4)C(O)R^4$, —R6—$N(R^4)C(O)OR^5$—$R^6$—$N(S(O)_tR^4)_2$ (where t is 0 to 2), —$R^6$—$N(R^4)(S(O)_tR^4)$ (where t is 0 to 2), —$R^6$—$S(O)_tR^4$ (where t is 0 to 2), and —$R^6$—$S(O)_pN(R^4)_2$ (where p is 1 or 2);

each $R^4$ is independently selected from the group consisting of hydrogen, alkyl, alkenyl, haloalkyl, hydroxyalkyl, optionally substituted cycloalkyl, optionally substituted cycloalkylalkyl, optionally substituted aryl, optionally substituted aralkyl, optionally substituted heterocyclyl and optionally substituted heteroaryl;

each $R^5$ is independently selected from the group consisting of hydrogen, alkyl, alkenyl, haloalkyl, hydroxyalkyl, cycloalkyl, cycloalkylalkyl, and aralkyl;

each $R^6$ is a direct bond or a straight or branched alkylene chain; and $R^7$ is hydrogen or aralkyl;

as a single stereoisomer, a mixture of stereoisomers, or as a racemic mixture of stereoisomers; or as a solvate or polymorph; or as a pharmaceutically acceptable salt thereof;

with the following provisos:

(a) when $R^7$ is hydrogen, n is 1, $R^1$ is chloro, methyl, trifluoromethyl or methoxy, and $R^3$ is methyl, $R^2$ can not be unsubstituted furanyl or thiophenyl optionally substituted by methyl;

(b) when $R^7$ is hydrogen, n is 1 or 2, each $R^1$ is independently halo, trifluoromethyl, an alkyl group of 1 to 3 carbons or —$R^6$—$OR^4$ where $R^6$ is a direct bond and $R^4$ is an alkyl group of 1 to 3 carbons, and $R^3$ is an alkyl group of 1 to 3 carbons, $R^2$ can not be phenyl optionally substituted by halo, an alkyl group of 1 to 3 carbons or —$R^6$—$OR^4$ where $R^6$ is a direct bond and $R^4$ is an alkyl group of 1 to 4 carbons;

(c) when $R^7$ is hydrogen, n is 1, $R^1$ is halo, methyl or methoxy, and $R^3$ is methyl, $R^2$ can not be oxazole;

(d) $R^1$ is other than —$R^6$—$C(O)OR^4$ where $R^6$ is a direct bond and $R^4$ is alkyl of 1 to 3 carbons.

* * * * *